US008637272B2

(12) United States Patent
Akiyama et al.

(10) Patent No.: US 8,637,272 B2
(45) Date of Patent: Jan. 28, 2014

(54) HALOHYDRIN EPOXIDASE

(75) Inventors: Takanori Akiyama, Yokohama (JP); Yu Fujio, Yokohama (JP); Fumiaki Watanabe, Yokohama (JP); Yuya Takikawa, Yokohama (JP); Eiji Sato, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 123 days.

(21) Appl. No.: 12/529,657

(22) PCT Filed: Mar. 7, 2008

(86) PCT No.: PCT/JP2008/054192
§ 371 (c)(1),
(2), (4) Date: Sep. 2, 2009

(87) PCT Pub. No.: WO2008/108466
PCT Pub. Date: Sep. 12, 2008

(65) Prior Publication Data
US 2010/0136617 A1     Jun. 3, 2010

(30) Foreign Application Priority Data
Mar. 7, 2007    (JP) ................. 2007-057854

(51) Int. Cl.
*C12P 21/06*    (2006.01)
*C12N 9/00*     (2006.01)
*C12N 9/88*     (2006.01)
*C12N 1/20*     (2006.01)
*C12N 15/00*    (2006.01)
*C07H 21/04*    (2006.01)

(52) U.S. Cl.
USPC ....... 435/69.1; 435/183; 435/232; 435/252.3; 435/320.1; 536/23.2

(58) Field of Classification Search
None
See application file for complete search history.

(56) References Cited

U.S. PATENT DOCUMENTS

| 4,413,142 | A | 11/1983 | Fiorini et al. |
| 5,166,061 | A | 11/1992 | Nakamura et al. |
| 5,210,031 | A | 5/1993 | Nakamura et al. |
| 2005/0153417 | A1 | 7/2005 | Davis et al. |
| 2005/0272064 | A1 | 12/2005 | Davis et al. |
| 2006/0099700 | A1* | 5/2006 | Davis et al. .................. 435/232 |

FOREIGN PATENT DOCUMENTS

| JP | 57165352 A | 10/1982 |
| JP | 353889 A | 3/1991 |
| JP | 353890 A | 3/1991 |
| JP | 04278089 A | 10/1992 |
| JP | 5317066 A | 12/1993 |
| JP | 10210981 A | 8/1998 |
| JP | 2001025397 A | 1/2001 |
| JP | 2007502123 A | 2/2007 |
| JP | 2007049932 A | 3/2007 |
| WO | 2005017141 A1 | 2/2005 |
| WO | 2006/091470 A2 | 8/2006 |

OTHER PUBLICATIONS

Chica et al. Curr Opin Biotechnol. Aug. 2005; 16(4):378-84.*
Sen et al. Appl Biochem Biotechnol. Dec. 2007;143(3):212-23.*
Mark R. Lewis, Cloning and Nucleotide Sequence of the 1,3-Dichloro-2-Propanol and 3-Chloro-1,2-Propanediol Dehalogenase Gene of Agrobacterium Tumefaciens HK7, A Thesis Presented for the Degree of Masters of Philosophy, School of Pure and Applied Biology, University of Wales Cardiff, United Kingdom, Jun. 1996.
Richard J. Fox, et al., Improving catalytic function by ProSAR-driven enzyme evolution, Nature Biotechnology, Feb. 18, 2007, pp. 338-344, vol. 25, No. 3 (ISSN: 1087-0156).
Johan E.T.van Hylckama Vlieg J. E.T. et al., Halohydrin dehalogenases are structurally and mechanistically related to short-chain dehydrogenases/reductases J. Bacteriol. 2001, 183(17), p. 5058-5066.
Yu et al., "Cloning of Two Halohydrin Hydrogen-Halide-Lyase Genes of Corynebacterium sp. Strain N-1074 and Structural Comparison of the Genes and Gene Products", Biosci. Biotech. Biochem, 58(8), 1451-1457; 1994.
Yonetani et al., "Isolation and Characterization of a 1,3-Dichloro-2-Propanol-Degrading Bacterium", J. of Health Sci., 50(6) 605-612, (2004).
Assis et al., "Biochemical characterization of a haloalcohol dehalogenase from Arthrobacter erithii H10a", Enzyme Microb. Technol., 1998, vol. 22, pp. 568-574, May 15.
Johan E. T. van Hylckama Vlieg et al., "Halohydrin Dehalogenases Are Structurally and Mechanistically Related to Short-Chain Dehydrogenases/Reductases" J. Bacteriology, vol. 183, No. 17; Sep. 2001, p. 5058-5066.
Tang et al., "Improved stability of halohydrin dehalogenase from Agrobacterium radiobacter AD1 by replacement of cysteine residues", Enzyme and microbial technology 30(2002) 251-258.
Jong et al., "Structure and mechanism of a bacterial haloalcohol dehalogenase: a new variation of the short-chain dehydrogenase/reductase fold without an NAD(P)H binding site" EMBO Journal, vol. 22, No. 19, pp. 4933-4944, 2003.

(Continued)

*Primary Examiner* — Christian Fronda
(74) *Attorney, Agent, or Firm* — McDermott Will & Emery LLP

(57) ABSTRACT

The present invention provides an industrially useful improved halohydrin epoxidase, a method for producing the same, and a method for producing an epihalohydrin or 4-halo-3-hydroxybutyronitrile using the same. The improved halohydrin epoxidase of the present invention consists of an amino acid sequence in which a specific amino acid substitution mutation is introduced into an amino acid sequence of a wild-type halohydrin epoxidase comprising predetermined amino acid sequences I and II.

16 Claims, 1 Drawing Sheet

(56) References Cited

OTHER PUBLICATIONS

Lixia Tang et al., "Steady-State Kinetics and Tryptophan Fluorescence Properties of Halohydrin Dehalogenase from Agrobacterium radiobacter. Roles of W139 and W249 in the Active Site and Halide-Induced Conformational Change", Biochemistry 2003, 42, 14057-14065.

Lixia Tang et al., "Improved Catalytic Properties of Halohydrin Dehalogenase by Modification of the Halide-Binding Site", Biochemistry 2005, 44, 6609-6618.

An Office Action mailed Oct. 9, 2012, which issued during the prosecution of Japanese Application No. 2008-517262, which corresponds to the present application.

* cited by examiner

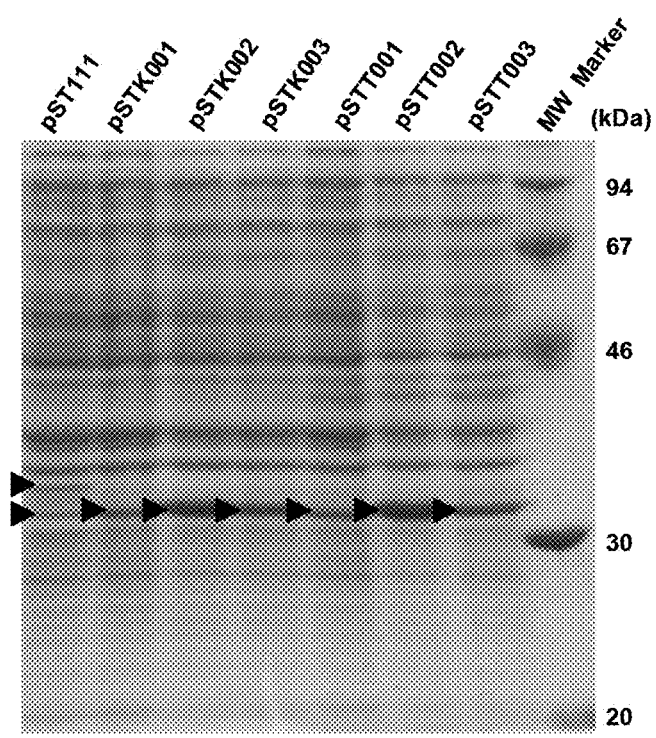

HALOHYDRIN EPOXIDASE

CROSS-REFERENCE TO PRIOR APPLICATION

This is the U.S. National Phase Application under 35 U.S.C. §371 of International Patent Application No. PCT/JP2008/054192 filed Mar. 7, 2008, which claims the benefit of Japanese Patent Application No. 2007-057854 filed Mar. 7, 2007, both of which are incorporated by reference herein. The International Application was published in Japanese on Sep. 12, 2008 as WO 2008/108466 A1 under PCT Article 21(2).

TECHNICAL FIELD

The present invention relates to an improved halohydrin epoxidase, a method for producing the same, etc.

BACKGROUND ART

Halohydrin epoxidase is also called halohydrin hydrogen-halide-lyase, halohydrin dehalogenase or haloalcohol dehalogenase, and is an enzyme having the activity to convert 1,3-dihalo-2-propanol into epihalohydrin and the activity to catalyze a reverse reaction thereof (EC number: 4.5.1.-). It is known that halohydrin epoxidase is roughly classified into 3 groups (Groups A, B and C) based on the amino acid sequence homology, etc. (Non-patent document 1: J. Bacteriology, 183 (17), 5058-5066, 2001). Examples of halohydrin epoxidases classified into Group A include HheA from *Corynebacterium* sp. strain N-1074 (Non-patent document 2: Biosci. Biotechnol. Biochem., 58 (8), 1451-1457, 1994), HheA$_{AD2}$ from *Arthrobacter* sp. strain AD2 (Non-patent document 1), and Deh-PY1 from *Arthrobacter* sp. strain PY1 (Non-patent document 3: J. Health. Sci., 50 (6), 605-612, 2004). Examples of halohydrin epoxidases classified into Group B include HheB from *Corynebacterium* sp. strain N-1074 (Non-patent document 2). HheB$_{GP1}$ from *Mycobacterium* sp. strain GP1 (Non-patent document 1), and DehA from *Arthrobacter erithii* strain H10a (Non-patent document 4: Enz. Microbiol. Technol., 22, 568-574, 1998). Examples of halohydrin epoxidases classified into Group C include HheC from *Agrobacterium radiobacter* strain DH094 (Patent document 1: Japanese Laid-Open Patent Publication No. 10-210981), HheC from *Agrobacterium radiobacter* strain AD1 (Non-patent document), and HalB from *Agrobacterium tumefaciens* (http://www.ncbi.nlm.nih.gov/entrez/viewer.fcgi?db=protein&val=4960076#feature_4960076) (Non-patent document 5: Thesis (1996) University of Wales, Cardiff, United Kingdom).

Epihalohydrin is a useful substance as a raw material for synthesis of various pharmaceutical products and physiologically active substances. For example, it is known that (R)-(−)-4-halo-3-hydroxybutyronitrile, which is obtained by ring-opening cyanation of (R)-epihalohydrin, is useful as a raw material for synthesis of L-carnitine (Patent document 2: Japanese Laid-Open Patent Publication No. 57-165352). It has become clear that at least a part of halohydrin epoxidases have the activity to catalyze a reaction in which epihalohydrin is subjected to ring-opening cyanation in the presence of a cyanogen compound to produce 4-halo-3-hydroxybutyronitrile in addition to the above-described activity to convert 1,3-dihalo-2-propanol into epihalohydrin and the activity to catalyze a reverse reaction thereof. As examples of utilization of the reaction, methods for producing an optically-active 4-halo-3-hydroxybutyronitrile from 1,3-dihalo-2-propanol (Patent document 3: Japanese Laid-Open Patent Publication No. 3-053889; Patent document 4: Japanese Laid-Open Patent Publication No. 2001-25397) and a method for producing an optically-active 4-halo-3-hydroxybutyronitrile from epihalohydrin (Patent document 5: Japanese Laid-Open Patent Publication No. 3-053890) are known.

The halohydrin epoxidase activity per cell of a microorganism separated from nature is not necessarily high enough from the viewpoint of industrial utilization. In order to solve this problem, attempts have been made to improve the halohydrin epoxidase activity per transformant utilizing the genetic engineering technique. For example, it is indicated that optically-active 4-halo-3-hydroxybutyronitrile can be efficiently produced using various transformants obtained by introducing various expression plasmids, which are obtained by cloning a gene encoding halohydrin epoxidase HheB from *Corynebacterium* sp. strain N-1074 (Patent document 6: Japanese Laid-Open Patent Publication No. 4-278089; Patent document 7: Japanese Laid-Open Patent Publication No. 5-317066; and Patent document 8: Japanese Laid-Open Patent Publication No. 2007-049932). Using these transformants, many copies of halohydrin epoxidase gene are retained in a bacterium, thereby significantly improving the halohydrin epoxidase activity per transformant.

Meanwhile, because of the recent progress of the genetic engineering technique, it has become possible to intentionally prepare a mutant in which one or more constituent amino acids of enzyme protein are deleted, added, inserted, or substituted with other amino acids. It is known that such mutants may provide improved performances such as activity, stability, organic solvent resistance, heat resistance, acid resistance, alkali resistance and substrate specificity compared to an enzyme without mutation depending on the type of mutation. The improvement of these performances may effect significant reduction in production cost in industrial production utilizing enzyme reactions through reduction in production cost of enzyme catalyst per activity, stabilization of enzyme catalyst, simplification of reaction process, improvement of reaction yield, etc. Therefore, utilizing many enzymes, useful improved enzymes with various improved performances have been created. It has been reported that mutants of halohydrin epoxidase in which one or more constituent amino acids are deleted, added, inserted or substituted with other amino acids were produced. For example, Patent document 9 (International Publication WO 2005/017141 pamphlet) describes 369 types of mutants of HheC from *Agrobacterium radiobacter* strain AD1 and a mutant of HheB from *Corynebacterium* sp. strain N-1074. Patent document 10 (US Laid-Open Publication No. 2005/0272064) describes 570 types of mutants of HheC from *Agrobacterium radiobacter* strain AD1 and a mutant of HheB from *Corynebacterium* sp. strain N-1074. In addition, Patent document 11 (US Laid-Open Publication No. 2006/0099700) describes 1422 types of mutants of HheC from *Agrobacterium radiobacter* strain AD1 and a mutant of HheB from *Corynebacterium* sp. strain N-1074. It is indicated that the activity in the reaction in which ethyl (R)-4-chloro-3-hydroxybutyrate is converted into ethyl (S)-4-cyano-3-hydroxybutyrate was improved when using several of these mutants. Non-patent document 6 (J. Bacteriol., 183 (17), 5058-5066, 2001) describes Ser132Ala, Ser132Cys, Tyr145Phe, Arg149Lys, Arg149Glu and Arg149Gln, which are mutants of HheC from *Agrobacterium radiobacter* strain AD1. Non-patent document 7 (Enz. Microbiol., Technol. 30, 251-258, 2002) describes C30A, C153S, C229A and C153S/C229A, which are mutants of HheC from *Agrobacterium radiobacter* strain AD1. It is indicated in the document that the stability in the case of the mutants C30A and C153S was improved compared to that in the case of wild-type halohydrin epoxidase.

Non-patent document 8 (EMBO J., 22 (19), 4933-4944, 2003) describes Asp80Asn and Asp80Ala, which are mutants of HheC from *Agrobacterium radiobacter* strain AD1. Non-patent document 9 (Biochemistry, 42 (47), 14057-14065, 2003) describes W139F, W192F, W238F and W249F, which are mutants of HheC from *Agrobacterium radiobacter* strain AD1. Non-patent document 10 (Biochemistry, 44 (17), 6609-6618, 2005) describes N176A, N176D and Y187F, which are mutants of HheC from *Agrobacterium radiobacter* strain AD1. All of these examples relate to mutants of halohydrin epoxidase HheC from *Agrobacterium radiobacter* strain AD1.

Patent document 1: Japanese Laid-Open Patent Publication No. 10-210981
Patent document 2: Japanese Laid-Open Patent Publication No. 57-165352
Patent document 3: Japanese Laid-Open Patent Publication No. 3-053889
Patent document 4: Japanese Laid-Open Patent Publication No. 2001-25397
Patent document 5: Japanese Laid-Open Patent Publication No. 3-053890
Patent document 6: Japanese Laid-Open Patent Publication No. 4-278089
Patent document 7: Japanese Laid-Open Patent Publication No. 5-317066
Patent document 8: Japanese Laid-Open Patent Publication No. 2007-049932
Patent document 9: International Publication WO 2005/017141 pamphlet
Patent document 10: US Laid-Open Publication No. 2005/0272064
Patent document 11: US Laid-Open Publication No. 2006/0099700
Non-patent document 1: J. Bacteriol., 183 (17), 5058-5066, 2001
Non-patent document 2: Biosci. Biotechnol. Biochem., 58 (8), 1451-1457, 1994
Non-patent document 3: J. Health. Sci. 50 (6), 605-612, 2004
Non-patent document 4: Enz. Microbiol. Technol., 22, 568-574, 1998
Non-patent document 5: Thesis (1996) University of Wales, Cardiff, United Kingdom
Non-patent document 6: J. Bacteriol., 183 (17), 5058-5066, 2001
Non-patent document 7: Enz. Microbiol., Technol. 30, 251-258, 2002
Non-patent document 8: EMBO J., 22 (19), 4933-4944, 2003
Non-patent document 9: Biochemistry, 42 (47), 14057-14065, 2003
Non-patent document 10: Biochemistry, 44 (17), 6609-6618, 2005

DISCLOSURE OF THE INVENTION

Problems to be Solved by the Invention

When halohydrin epoxidase is industrially utilized, it is desired to be further developed as an enzyme catalyst. For example, as described above, the halohydrin epoxidase activity per transformant can be increased to some extent by multicopying of the halohydrin epoxidase gene in the transformant. However, from the viewpoint of economic efficiency and practical utility, the activity is desired to be further improved. Therefore, a halohydrin epoxidase, which realizes the improvement of the halohydrin epoxidase activity per transformant, is desired. Further, when the production of an optically-active 4-halo-3-hydroxybutyronitrile is intended, the optical purity of 4-halo-3-hydroxybutyronitrile produced using an already-known halohydrin epoxidase is not necessarily high enough. Therefore, a halohydrin epoxidase having improved stereoselectivity, which enables production of 4-halo-3-hydroxybutyronitrile having a higher optical purity, is desired. Moreover, when 4-halo-3-hydroxybutyronitrile is produced from 1,3-dihalo-2-propanol as a starting material using a halohydrin epoxidase, decrease in the reaction velocity due to inhibition by products (chloride ion and 4-halo-3-hydroxybutyronitrile) may occur. Therefore, a halohydrin epoxidase, which is unlikely to be affected by inhibition by products, is desired. Furthermore, in order to produce 4-halo-3-hydroxybutyronitrile at low cost, in general, it is desirable that the productivity per apparatus is improved by setting a higher concentration of a substrate and/or product (4-halo-3-hydroxybutyronitrile) in a reaction system. However, the concentration of product accumulation of an already-known halohydrin epoxidase is not necessarily high enough. Therefore, a halohydrin epoxidase, which can accumulate a product at a high concentration, is desired.

Therefore, the purpose of the present invention is to provide a halohydrin epoxidase, which can solve the above-described problems, a method for producing the same, and a method for producing an epihalohydrin or 4-halo-3-hydroxybutyronitrile using the same.

Means for Solving the Problems

The present inventors diligently made researches in order to solve the above-described problems. As a result, the present inventors found that an improved halohydrin epoxidase having improved properties such as halohydrin epoxidase activity per transformant, stereoselectivity, resistance to inhibition by products and product accumulation ability can be created by substituting specific amino acid residues with other amino acids in an amino acid sequence of a wild-type halohydrin epoxidase, in particular an amino acid sequence of a wild-type halohydrin epoxidase which is classified into Group B. Thus, the present invention was achieved.

That is, the present invention is as follows:

(1) An improved halohydrin epoxidase consisting of an amino acid sequence in which any one of or a plurality of amino acid mutations selected from (A) to (D) below are introduced into an amino acid sequence of a wild-type halohydrin epoxidase comprising:

the following amino acid sequence I:

$$\text{S-}\alpha_1\text{-}\alpha_2\text{-}\alpha_3\text{-}\alpha_4\text{-}\alpha_5\text{-}\alpha_6\text{-}\alpha_7\text{-}\alpha_8\text{-}\alpha_9\text{-}\alpha_{10}\text{-}\alpha_{11}\text{-}\alpha_{12}\text{-Y-}\alpha_{13}\text{-}\alpha_{14}\text{-A-R-}\alpha_{15} \quad \text{(SEQ ID NO: 74)}$$

(wherein S, Y, A and R represent serine residue, tyrosine residue, alanine residue and arginine residue, respectively, and $\alpha_1$ to $\alpha_{15}$ each independently represent any amino acid residue and $\alpha_1$ to $\alpha_{15}$ may be the same or different); and the following amino acid sequence II:

$$\text{L-}\beta_{16}\text{-R-L-}\beta_{17}\text{-}\beta_{18}\text{-}\beta_{19}\text{-}\beta_{20}\text{-E-}\beta_{21} \quad \text{(SEQ ID NO: 75)}$$

(wherein L, R and E represent leucine residue, arginine residue and glutamic acid residue, respectively, and $\beta_{16}$ to $\beta_{21}$ each independently represent any amino acid residue and $\beta_{16}$ to $\beta_{21}$ may be the same or different):

(A) an amino acid mutation in which an amino acid residue which is one residue closer to the C-terminal end than the start amino acid residue (usually a methionine residue) is substituted with another amino acid;
(B) an amino acid mutation in which α14 residue is substituted with another amino acid;
(C) an amino acid mutation in which α15 residue is substituted with another amino acid; and
(D) an amino acid mutation in which β21 residue is substituted with another amino acid.

(2) An improved halohydrin epoxidase consisting of an amino acid sequence in which any one of or a plurality of amino acid mutations selected from (E) to (H) below are introduced into an amino acid sequence of a wild-type halohydrin epoxidase comprising:
the following amino acid sequence I:

```
                                          (SEQ ID NO: 74)
S-α1-α2-α3-α4-α5-α6-α7-α8-α9-α10-α11-α12-Y-α13-

α14-A-R-α15
```

(wherein S, Y, A and R represent serine residue, tyrosine residue, alanine residue and arginine residue, respectively, and α1 to α15 each independently represent any amino acid residue and α1 to α15 may be the same or different); and the following amino acid sequence II:

```
L-β16-R-L-β17-β18-β19-β20-E-β21      (SEQ ID NO: 75)
```

(wherein L, R and E represent leucine residue, arginine residue and glutamic acid residue, respectively, and β16 to β21 each independently represent any amino acid residue and β16 to β21 may be the same or different):
(E) an amino acid mutation in which an amino acid residue which is one residue closer to the C-terminal end than the start amino acid residue (usually a methionine residue) is substituted with lysine or asparagine;
(F) an amino acid mutation in which α14 residue is substituted with alanine, cysteine or serine;
(G) an amino acid mutation in which α15 residue is substituted with alanine, serine or tryptophan; and
(H) an amino acid mutation in which β21 residue is substituted with glutamine, glutamic acid, histidine, serine, threonine, tyrosine, leucine, isoleucine or methionine.

Regarding the improved halohydrin epoxidases according to items (1) and (2), examples of the wild-type halohydrin epoxidases include those classified into Group B.

Regarding the improved halohydrin epoxidases according to items (1) and (2), examples of the wild-type halohydrin epoxidases include those derived from a bacterium of the genus *Corynebacterium* or a bacterium of the genus *Mycobacterium*.

Regarding the improved halohydrin epoxidases according to items (1) and (2), examples of amino acid sequences of the wild-type halohydrin epoxidases include an amino acid sequence represented by SEQ ID NO: 1 or 2.

Examples of the improved halohydrin epoxidases according to items (1) and (2) include those consisting of an amino acid sequence in which any one of or a plurality of amino acid mutations selected from (i) to (iii) below are introduced into an amino acid sequence of the wild-type halohydrin epoxidase:
(i) an amino acid mutation in which one or several amino acid residues selected from amino acid residues other than the amino acid residue which is one residue closer to the C-terminal end than the start amino acid residue, α14 residue, α15 residue and β21 residue are substituted with other amino acids;
(ii) an amino acid mutation in which one or several amino acid residues selected from amino acid residues other than the amino acid residue which is one residue closer to the C-terminal end than the start amino acid residue, amino acid residues contained in the amino acid sequence I and amino acid residues contained in the amino acid sequence II are deleted; and
(iii) an amino acid mutation in which one or several arbitrary amino acid residues are inserted in a region, which consists of amino acid residues which are two or more residues closer to the C-terminal end than the start amino acid residue, and which excludes a region consisting of the amino acid sequences I and II.

(3) A gene encoding the improved halohydrin epoxidase according to item (1) or (2).
(4) A recombinant vector comprising the gene according to item (3).
(5) A transformant or transductant obtained by introducing the recombinant vector according to item (4) into a host.
(6) A culture obtained by culturing the transformant or transductant according to item (5).
(7) An improved halohydrin epoxidase collected from the culture according to item (6).
(8) A method for producing an improved halohydrin epoxidase, wherein the transformant or transductant according to item (5) is cultured and from a culture obtained, the improved halohydrin epoxidase is collected.
(9) A method for producing an epihalohydrin, wherein the epihalohydrin is produced by bringing the improved halohydrin epoxidase according to item (1), (2) or (7) and/or the culture according to item (6) into contact with 1,3-dihalo-2-propanol.
(10) A method for producing a 4-halo-3-hydroxybutyronitrile, wherein the 4-halo-3-hydroxybutyronitrile is produced by bringing the improved halohydrin epoxidase according to item (1), (2) or (7) and/or the culture according to item (6) into contact with 1,3-dihalo-2-propanol or epihalohydrin in the presence of a cyanogen compound.

Advantageous Effect of the Invention

According to the present invention, improved halohydrin epoxidases having improved properties such as halohydrin epoxidase activity per transformant, stereoselectivity, resistance to inhibition by products and product accumulation ability can be obtained. In addition, utilizing these products, an epihalohydrin or a 4-halo-3-hydroxybutyronitrile can be efficiently produced.

BRIEF DESCRIPTION OF THE DRAWINGS

FIG. 1 shows results of SDS-PSGE analysis of crude enzyme solutions from transformants expressing wild-type halohydrin epoxidase (JM109/pST111, JM109/pSTK001 and JM109/pSTT001) and transformants expressing improved halohydrin epoxidase (JM109/pSTK002, JM109/pSTK003, JM109/pSTT002 and JM109/pSTT003).

BEST MODE FOR CARRYING OUT THE INVENTION

Hereinafter, the embodiment of the present invention will be described. The embodiment is provided only for illustrative purposes, and it is not intended that the present invention be limited only to this embodiment. The present invention can be practiced employing various modes without departing from the gist of the present invention.

Note that the entire specification of Japanese Patent Application No. 2007-057854, to which priority is claimed by the present application, is incorporated herein. In addition, all the publications such as prior art documents, laid-open publications, patents and other patent documents cited herein are incorporated herein by reference.

(I) Halohydrin Epoxidase Activity

As used herein, the "halohydrin epoxidase activity" means the activity to convert 1,3-dihalo-2-propanol into epihalohydrin and the activity to catalyze a reverse reaction thereof. 1,3-dihalo-2-propanol is a compound represented by the following general formula (1):

[Chemical Formula 1]

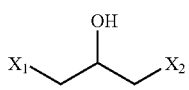

(1)

(wherein $X_1$ and $X_2$ each independently represent a halogen atom and $X_1$ and $X_2$ may be the same or different.)

As the halogen atom, fluorine, chlorine, bromine and iodine are preferred, and chlorine and bromine are particularly preferred. Specific examples thereof include 1,3-difluoro-2-propanol, 1,3-dichloro-2-propanol (hereinafter sometimes referred to as "DCP"), 1,3-dibromo-2-propanol, and 1,3-diiodo-2-propanol, and 1,3-dichloro-2-propanol and 1,3-dibromo-2-propanol are preferred.

Epihalohydrin is a compound represented by the following general formula (2):

[Chemical Formula 2]

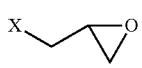

(2)

(wherein X represents a halogen atom.)

As the halogen atom, fluorine, chlorine, bromine and iodine are preferred, and chlorine and bromine are particularly preferred. Specific examples thereof include epifluorohydrin, epichlorohydrin (hereinafter sometimes referred to as "ECH"), epibromohydrin and epiiodohydrin, and epichlorohydrin and epibromohydrin are particularly preferred.

In the present invention, the "halohydrin epoxidase activity" can be obtained by measuring the amount of production of epihalohydrin or chloride ion from 1,3-dihalo-2-propanol per time. Production of epihalohydrin can be quantified, for example, by means of liquid chromatography, gas chromatography or the like. The production amount of chloride ion can be obtained, for example, as follows: alkali solution is added continuously or intermittently so that pH, which decreases along with the production of chloride ion, can be maintained at a specific value; and the production amount of chloride ion is conveniently obtained based on the amount of alkali required per time. The halohydrin epoxidase activity calculated according to this method is sometimes called "dechlorination activity". Further, alternatively, an antibody to the improved halohydrin epoxidase is prepared, and the calculation can be performed by means of immunological techniques such as western blotting and ELISA. When assuming that the halohydrin epoxidase activity is proportional to the expression level in a transformant, the activity can be indirectly obtained, for example, by comparison with a sample having an already-known halohydrin epoxidase activity using SDS-PAGE analysis or the like. SDS-PAGE can be performed using a method known in the art.

At least some halohydrin epoxidases have the activity to catalyze a reaction in which epihalohydrin is subjected to ring-opening cyanation in the presence of a cyanogen compound to produce 4-halo-3-hydroxybutyronitrile in addition to the above-described "halohydrin epoxidase activity". Examples of cyanogen compounds in this case include hydrogen cyanide, potassium cyanide (hereinafter sometimes referred to as "KCN"), sodium cyanide, compounds which generate cyanogen ion (CN—) or hydrogen cyanide when added to a reaction solution such as cyanic acid, acetone cyanhydrin, etc., and solutions thereof. 4-halo-3-hydroxybutyronitrile is a compound represented by the following general formula (3):

[Chemical Formula 3]

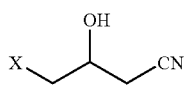

(3)

(wherein X represents a halogen atom.)

As the halogen atom, fluorine, chlorine, bromine and iodine are preferred, and chlorine and bromine are particularly preferred. Specific examples thereof include 4-fluoro-3-hydroxybutyronitrile, 4-chloro-3-hydroxybutyronitrile (hereinafter sometimes referred to as "CHBN"), 4-bromo-3-hydroxybutyronitrile and 4-iodo-3-hydroxybutyronitrile, and 4-chloro-3-hydroxybutyronitrile and 4-bromo-3-hydroxybutyronitrile are preferred.

(II) Halohydrin Epoxidase (II-1) Wild-Type Halohydrin Epoxidase

The improved halohydrin epoxidase of the present invention is an improved one obtained by introducing mutation (amino acid mutation) into a wild-type halohydrin epoxidase (particularly preferably a wild-type halohydrin epoxidase classified into Group B), and its origin is not particularly limited. In this regard, the "wild-type halohydrin epoxidase" refers to halohydrin epoxidases which can be separated from living organisms in nature, and means halohydrin epoxidases retaining naturally-derived properties, wherein in amino acid sequences constituting the enzymes, there is no intentional or unintentional deletion of amino acids or substitution with other amino acids or insertion of other amino acids.

The wild-type halohydrin epoxidase to be used in the present invention consists of an amino acid sequence comprising:

the following amino acid sequence I (19 amino acid residues):

(SEQ ID NO: 74)
S-α1-α2-α3-α4-α5-α6-α7-α8-α9-α10-α11-α12-Y-α13-

α14-A-R-α15

(wherein S, Y, A and R represent serine residue, tyrosine residue, alanine residue and arginine residue, respectively, and α1 to α15 each independently represent any amino acid residue and α1 to α15 may be the same or different); and the following amino acid sequence II (10 amino acid residues):

L-β16-R-L-β17-β18-β19-β20-E-β21    (SEQ ID NO: 75)

(wherein L, R and E represent leucine residue, arginine residue and glutamic acid residue, respectively, and β16 to β21 each independently represent any amino acid residue and β16 to β21 may be the same or different). The question of whether or not a wild-type halohydrin epoxidase consists of an amino acid sequence comprising the amino acid sequences I and II can be studied as follows: substances registered as "halohydrin epoxidase" are searched for using public sequence database (e.g., GenBank database provided by National Center for Biotechnology Information (NCBI) (http://www.ncbi.ncbi.nlm.nih.gov/entrez/query.fcgi?CMD=search&DB=protein)); and whether or not the above-described amino acid sequences I and II are included in amino acid sequences of the relevant substances is studied. According to need, such study can be carried out using a software for analysis of gene information. In addition, publicly-known documents which describe an amino acid sequence of a wild-type halohydrin epoxidase can be referred to. For example, by referring to the alignment information of amino acid sequences of various wild-type halohydrin epoxidases described in J. Bacteriology, 183 (17), 5058-5066, 2001, it can be known whether or not the amino acid sequences I and II are included and at which positions in entire amino acid sequences the amino acid sequences I and II are included. Note that the serine residue, tyrosine residue, arginine residue and alanine residue in the amino acid sequence I and the leucine residue, arginine residue and glutamic acid residue in the amino acid sequence II are highly conserved in amino acid sequences of already-known various wild-type halohydrin epoxidases.

It is known that wild-type halohydrin epoxidases are roughly classified into 3 groups (Group A, Group B and Group C) based on amino-acid sequence homology, etc. (J. Bacteriology, 18 3(17), 5058-5066, 2001). Among them, as the wild-type halohydrin epoxidase to be used in the present invention, those belonging to Group B are particularly preferred.

Examples of halohydrin epoxidases classified into Group A include HheA from *Corynebacterium* sp. strain N-1074 (Biosci. Biotechnol. Biochem., 58 (8), 1451-1457, 1994), HheA$_{AD2}$ from *Arthrobacter* sp. strain AD2 (J. Bacteriology, 183 (17), 5058-5066, 2001), and Deh-PY1 from *Arthrobacter* sp. PY1 (J. Health. Sci., 50 (6), 605-612, 2004).

Examples of halohydrin epoxidases classified into Group B include HheB from *Corynebacterium* sp. strain N-1074 (Biosci. Biotechnol. Biochem., 58 (8), 1451, 1994), HheB$_{GP1}$ from *Mycobacterium* sp. strain GP1 (J. Bacteriology, 183 (17), 5058-5066, 2001), and DehA from *Arthrobacter erithii* strain H10a (Enz. Microbiol. Technol., 22, 568-574, 1998). Examples of halohydrin epoxidases classified into Group C include HheC from *Agrobacterium radiobacter* strain DH094 (Japanese Laid-Open Patent Publication No. 10-210981), HheC from *Agrobacterium radiobacter* strain AD1 (J. Bacteriology, 183 (17), 5058-5066, 2001), and HalB from *Agrobacterium tumefaciens* (Thesis (1996) University of Wales, Cardiff, United Kingdom).

Among the above-described halohydrin epoxidases, those whose amino acid sequence has been revealed have been registered in GenBank database provided by National Center for Biotechnology Information (NCBI) (http://www.ncbi.nlm.nih.gov/entrez/query.fcgi?CMD=search&DB=protein) with the following Accession Numbers.

"Accession No. BAA14361": Amino acid sequence of HheA from *Corynebacterium* sp. strain N-1074

"Accession No. AAK92100": Amino acid sequence of HheA$_{AD2}$ from *Arthrobacter* sp. strain AD2

"Accession No. BAA14362": Amino acid sequence of HheB from *Corynebacterium* sp. strain N-1074

"Accession No. AAK73175": Amino acid sequence of HheB$_{GP1}$ from *Mycobacterium* sp. strain GP1

"Accession No. AAK92099": Amino acid sequence of HheC from *Agrobacterium radiobacter* strain AD1

"Accession No. AAD34609": Amino acid sequence of HalB from *Agrobacterium tumefaciens*

It has been reported that the halohydrin epoxidase HheB from *Corynebacterium* sp. strain N-1074, which is the main example of the present invention, has two types of halohydrin epoxidases, wherein the only difference is the presence or absence of 8 amino acid residues in the vicinity of N-terminal end, because the gene (HheB) has 2 initiation codons (Biosci. Biotechnol. Biochem., 58 (8), 1451-1457, 1994). In the present invention, when the above-described two types of halohydrin epoxidases are distinguished from each other, HheB consisting of the amino acid sequence translated from the first initiation codon (SEQ ID NO: 1) is designated as "HheB($1^{st}$)", and HheB consisting of the amino acid sequence translated from the second initiation codon (SEQ ID NO: 2) is designated as "HheB($2^{nd}$)". Both are wild-type halohydrin epoxidases.

In this regard, in HheB($1^{st}$) consisting of the amino acid sequence represented by SEQ ID NO: 1, the amino acid sequence I corresponds to a sequence consisting of amino acid residues at positions 126 to 144, and the amino acid sequence II corresponds to a sequence consisting of amino acid residues at positions 198 to 207. In HheB($2^{nd}$) consisting of the amino acid sequence represented by SEQ ID NO: 2, the amino acid sequence I corresponds to a sequence consisting of amino acid residues at positions 118 to 136, and the amino acid sequence II corresponds to a sequence consisting of amino acid residues at positions 190 to 199. Further, under the influence of the aforementioned two initiation codons, the amino acid sequence of HheB($2^{nd}$) consists of an amino acid sequence in which 8 amino acid residues in the vicinity of N-terminal end in the amino acid sequence of HheB($1^{st}$) (specifically, amino acid residues at positions 1 to 8 in the amino acid sequence represented by SEQ ID NO: 1) are deleted.

In the explanation in this specification, the main example of the halohydrin epoxidase is HheB, which is a wild-type halohydrin epoxidase from *Corynebacterium* sp. strain N-1074. However, as described above, the origin of the halohydrin epoxidase is not limited. The same explanation can be applied to halohydrin epoxidases other than HheB as long as they consist of an amino acid sequence comprising the aforementioned amino acid sequences I and II. Further, any improved halohydrin epoxidase can be obtained by modifying the position of mutation or the type of amino acid or nucleotide sequence to be mutated indicated by the present invention. In the present invention, "high homology" refers to, for example, homology of 60% or higher, preferably homology of 75% or higher, and particularly preferably homology of 90% or higher.

(II-2) Improved Halohydrin Epoxidase

The "improved halohydrin epoxidase" in the present invention consists of an amino acid sequence in which at least one amino acid substitution mutation is introduced into an amino acid sequence of a wild-type halohydrin epoxidase mainly utilizing the genetic recombination technology, wherein the halohydrin epoxidase activity per transformant, stereoselectivity, resistance to inhibition by products, product accumulation ability, etc. are improved.

The improved halohydrin epoxidase of the present invention includes those whose halohydrin epoxidase activity per transformant is higher than that of wild-type halohydrin epoxidases. In this regard, the essential cause of the improvement of the halohydrin epoxidase activity per transformant may be any matter arising from amino acid substitution mutation. Examples thereof include: improvement of specific activity per enzyme protein per se; improvement of ability to form active conformation; increase of expression level in transformants; improvement of stability of enzyme in transformants; improvement of resistance to substrates; and reduction in sensitivity to inhibition by products.

The "halohydrin epoxidase activity per transformant" means "halohydrin epoxidase activity per unit weight of dried cells of transformants" and is also referred to as "cell specific activity" (as used herein, the dried cell is sometimes referred to as "DC"). The "halohydrin epoxidase activity per soluble protein" means "halohydrin epoxidase activity per unit weight of soluble protein" and is also referred to as "protein specific activity". Further, in the present invention, as a matter of convenience, it is considered that a specific amount of soluble protein can be obtained from a specific amount of transformant, and the "halohydrin epoxidase activity per transformant" ("cell specific activity") is regarded as being proportional to the "halohydrin epoxidase activity per soluble protein" ("protein specific activity"). That is, when the "halohydrin epoxidase activity per soluble protein" ("protein specific activity") is high (low), the "halohydrin epoxidase activity per transformant" ("cell specific activity") is regarded as being high (low). In the present invention, the "liquid activity" means halohydrin epoxidase activity per unit volume of solution. Examples of the solution include a solution containing a product which can be obtained from a "culture" obtained by culturing a transformant that produces a halohydrin epoxidase. Specific examples thereof include culture solution, culture supernatant fluid, suspension containing higher eukaryotic cells or microbial cells, a disintegrated product of higher eukaryotic cells or microbial cells, crude enzyme solution, and products obtained by treatment thereof. By dividing the "liquid activity" by the concentration of cell or soluble protein of the solution, the "halohydrin epoxidase activity per transformant" ("cell specific activity") or the "halohydrin epoxidase activity per soluble protein" ("protein specific activity") can be calculated. As used herein, "activity recovery ratio" means a relative ratio (%) of activity recovered after an operation to given activity before the operation (100%).

The improved halohydrin epoxidase of the present invention includes those having a property in which the optical purity of epihalohydrin or 4-halo-3-hydroxybutyronitrile in the case where the product is produced from a substrate 1,3-dihalo-2-propanol or epihalohydrin is higher than the optical purity of the same product in the case where the product is produced from the same substrate using a wild-type halohydrin epoxidase. That is, the improved halohydrin epoxidase include those having improved stereoselectivity with respect to the substrate 1,3-dihalo-2-propanol and/or epihalohydrin compared to that of the wild-type halohydrin epoxidase. The essential cause of the improvement of stereoselectivity may be any matter arising from amino acid substitution mutation.

As used herein, "optical activity" refers to a state of a substance in which one enantiomer is contained more than the other enantiomer, or a state of a substance consisting of only one of enantiomers. Further, the "optical purity" is regarded as being almost equal to "enantiomer excess (% ee)", and this is defined by the following formula:

Optical purity≈Enantiomer excess=100×(|[R]−[S]|)/ ([R]+[S])(% ee)

In this regard, [R] and [S] represent respective concentrations of enantiomers in a sample. Further, as used herein, "stereoselectivity" refers to a property of halohydrin epoxidase in which a reaction generated by one of enantiomers is preferentially catalyzed at the time of production of a product from a substrate.

Moreover, the improved halohydrin epoxidase of the present invention include those in which resistance to reaction inhibition by chloride ion or 4-halo-3-hydroxybutyronitrile, which is a product produced from 1,3-dihalo-2-propanol or epihalohydrin, is improved compared to that of the wild-type halohydrin epoxidase, i.e., halohydrin epoxidases having improved resistance to inhibition by products. The essential cause of the improvement of the resistance to inhibition by products may be any matter arising from amino acid substitution mutation.

Furthermore, the improved halohydrin epoxidase of the present invention include those having a property in which epihalohydrin or 4-halo-3-hydroxybutyronitrile can be produced and accumulated in high concentration when the product is produced from the substrate 1,3-dihalo-2-propanol or epihalohydrin, i.e., halohydrin epoxidases having improved product accumulation ability. The essential cause of the improvement of product accumulation ability may be any matter arising from amino acid substitution mutation.

Specifically, the "improved halohydrin epoxidase" of the present invention consists of an amino acid sequence in which any one of or a plurality of amino acid mutations selected from (A) to (D) below are introduced into an amino acid sequence of a wild-type halohydrin epoxidase comprising the aforementioned amino acid sequences I and II:
(A) an amino acid mutation in which an amino acid residue which is one residue closer to the C-terminal end than the start amino acid residue is substituted with another amino acid;
(B) an amino acid mutation in which α14 residue in the amino acid sequence I is substituted with another amino acid;
(C) an amino acid mutation in which α15 residue in the amino acid sequence I is substituted with another amino acid; and
(D) an amino acid mutation in which β21 residue in the amino acid sequence II is substituted with another amino acid.

In (A) described above, the "start amino acid residue" means an amino acid residue corresponding to an amino acid encoded by the translation initiation codon in the gene (DNA or mRNA) of a wild-type halohydrin epoxidase, i.e., N-terminal amino acid residue (usually a methionine residue) in an amino acid sequence of a wild-type halohydrin epoxidase after translation.

The amino acid mutations in (A) to (D) above can also be specified by the matter as to what position number of amino acid residue (any of position numbers starting from the start amino acid residue to the C-terminal end) has an amino acid mutation when defining the start amino acid residue (usually a methionine residue), which is at the N-terminal end in the amino acid sequence of the wild-type halohydrin epoxidase, as being at position-1. For example, when a wild-type halohydrin epoxidase is HheB(1$^{st}$) from *Corynebacterium* sp. strain N-1074 consisting of the amino acid sequence represented by SEQ ID NO: 1, the "amino acid residue which is one residue closer to the C-terminal end than the start amino acid residue" in (A), the "α14 residue" in (B), the "α15 residue" in (C) and the "β21 residue" in (D) correspond to (A) amino acid residue at position-2 (alanine residue), (B) amino acid residue at position-141 (threonine residue), (C) amino acid residue at position-144 (phenylalanine residue) and (D) amino acid residue at position-207 (aspartic acid residue), respectively. When a wild-type halohydrin epoxidase is HheB ($2^{nd}$) from *Corynebacterium* sp. strain N-1074 consisting of the amino acid sequence represented by SEQ ID NO: 2, the "amino acid residue which is one residue closer to the C-terminal end than the start amino acid residue" in (A), the "α14 residue" in (B), the "α15 residue" in (C) and the "β21 residue" in (D) correspond to (A) amino acid residue at position-2 (alanine residue), (B) amino acid residue at position-133 (threonine residue), (C) amino acid residue at position-136 (phenylalanine residue) and (D) amino acid residue at position-199 (aspartic acid residue), respectively. However, as described above, HheB($2^{nd}$) is just a protein consisting of an amino acid sequence in which 8 amino acid residues in the vicinity of N-terminal end in the amino acid sequence of HheB($1^{st}$) are deleted. Therefore, the absolute functions of the respective amino acid residues in the amino acid sequence of HheB($1^{st}$) are substantially the same as those of the respective amino acid residues in the amino acid sequence of HheB ($2^{nd}$).

Examples of preferred embodiments of the "improved halohydrin epoxidase" in the present invention include those consisting of an amino acid sequence into which any one of or a plurality of amino acid mutations selected from (E) to (H) below are introduced:

(E) an amino acid mutation in which an amino acid residue which is one residue closer to the C-terminal end than the start amino acid residue (usually a methionine residue) is substituted with another amino acid, i.e., lysine or asparagine;

(F) an amino acid mutation in which α14 residue in the amino acid sequence I is substituted with another amino acid, i.e., alanine, cysteine or serine;

(G) an amino acid mutation in which α15 residue in the amino acid sequence I is substituted with another amino acid, i.e., alanine, serine or tryptophan; and (H) an amino acid mutation in which β21 residue in the amino acid sequence II is substituted with another amino acid, i.e., glutamine, glutamic acid, histidine, serine, threonine, tyrosine, leucine, isoleucine or methionine.

In this regard, the above-described amino acid mutations (E) to (H) are examples of specific embodiments of the aforementioned amino acid mutations (A) to (D) in this order (for details, specific examples of "another amino acid").

Therefore, like the aforementioned cases of (A) to (D), the "amino acid residue which is one residue closer to the C-terminal end than the start amino acid residue" in (E), the "α14 residue" in (F), the "α15 residue" in (G) and the "β21 residue" in (H) can be specified by the matter as to what position number of amino acid (any of position numbers starting from the start amino acid residue to the C-terminal end) corresponds thereto when defining the start amino acid residue (usually a methionine residue), which is at the N-terminal end in the amino acid sequence of the wild-type halohydrin epoxidase, as being at position-1. That is, when a wild-type halohydrin epoxidase is HheB($1^{st}$) from *Corynebacterium* sp. strain N-1074 consisting of the amino acid sequence represented by SEQ ID NO: 1, the embodiments of the above-described amino acid mutations (E) to (H) can be specified as follows:

(E) an amino acid mutation in which the amino acid residue at position-2 (alanine residue) is substituted with lysine or asparagine;

(F) an amino acid mutation in which the amino acid residue at position-141 (threonine residue) is substituted with alanine, cysteine or serine;

(G) an amino acid mutation in which the amino acid residue at position-144 (phenylalanine residue) is substituted with alanine, serine or tryptophan; and (H) an amino acid mutation in which the amino acid residue at position-207 (aspartic acid residue) is substituted with glutamine, glutamic acid, histidine, serine, threonine, tyrosine, leucine, isoleucine or methionine.

When a wild-type halohydrin epoxidase is HheB($2^{nd}$) from *Corynebacterium* sp. strain N-1074 consisting of the amino acid sequence represented by SEQ ID NO: 2, the embodiments of the above-described amino acid mutations (E) to (H) can be specified as follows:

(E) an amino acid mutation in which the amino acid residue at position-2 (alanine residue) is substituted with lysine or asparagine;

(F) an amino acid mutation in which the amino acid residue at position-133 (threonine residue) is substituted with alanine, cysteine or serine;

(G) an amino acid mutation in which the amino acid residue at position-136 (phenylalanine residue) is substituted with alanine or serine; and (H) an amino acid mutation in which the amino acid residue at position-199 (aspartic acid residue) is substituted with glutamine, glutamic acid, histidine, serine, threonine, isoleucine or tyrosine.

When a wild-type halohydrin epoxidase is HheB($1^{st}$) from *Corynebacterium* sp. strain N-1074 having the amino acid sequence represented by SEQ ID NO: 1, examples of more specific and preferred embodiments of the "improved halohydrin epoxidase" in the present invention include improved halohydrin epoxidases having any of the amino acid sequences represented by SEQ ID NOs: 3-15 and 76-79. When a wild-type halohydrin epoxidase is HheB($2^{nd}$) from *Corynebacterium* sp. strain N-1074 having the amino acid sequence represented by SEQ ID NO: 2, examples of more specific and preferred embodiments include improved halohydrin epoxidases having any of the amino acid sequences represented by SEQ ID NOs: 16-28 and 80-83.

Hereinafter, embodiments of amino acid mutations (amino acid substitutions) in the amino acid sequences represented by SEQ ID NOs: 3-15 and 76-79 are shown in Table A, and embodiments of amino acid mutations (amino acid substitutions) in the amino acid sequences represented by SEQ ID NOs: 16-28 and 80-83 are shown in Table B. In this regard, in Table A, descriptions "Ala2", "Thr141", "Phe144" and "Asp207" represent the position and type of an amino acid residue (three-character codes) targeted for amino acid substitution in the amino acid sequence represented by SEQ ID NO: 1. For example, "Thr141" means a threonine residue at position-141. Further, descriptions in columns below "Ala2", etc. represent amino acid residues in the amino acid sequences represented by SEQ ID NOs: 3-15 and 76-79 after amino acid substitution. For example, regarding the amino acid sequence represented by SEQ ID NO: 3, "Lys" is described below "Ala2", and it means an amino acid sequence in which an alanine residue at position-2 is substituted with a lysine residue. The description "-" means that there is no amino acid substitution. In addition, SEQ ID NOs: of nucleotide sequences encoding the amino acid sequences (described later) after amino acid substitution are described in the rightmost columns in the table. The above-described explanation regarding the descriptions in Table A is applied to Table B.

TABLE A

| SEQ ID NO: (amino acid sequence) | Embodiment of amino acid substitution | | | | SEQ ID NO: (nucleotide sequence) |
|---|---|---|---|---|---|
| | Ala2 | Thr141 | Phe144 | Asp207 | |
| 3 | Lys | — | — | — | 31 |
| 4 | Asn | — | — | — | 32 |
| 5 | — | Ala | — | — | 33 |
| 6 | — | Cys | — | — | 34 |
| 7 | — | Ser | — | — | 35 |
| 8 | — | — | Ala | — | 36 |
| 9 | — | — | Ser | — | 37 |
| 76 | — | — | Trp | — | 84 |
| 10 | — | — | — | Gln | 38 |
| 11 | — | — | — | Glu | 39 |
| 12 | — | — | — | His | 40 |
| 13 | — | — | — | Ser | 41 |
| 14 | — | — | — | Thr | 42 |
| 15 | — | — | — | Tyr | 43 |
| 77 | — | — | — | Leu | 85 |
| 78 | — | — | — | Met | 86 |
| 79 | — | — | — | Ile | 87 |

TABLE B

| SEQ ID NO: (amino acid sequence) | Embodiment of amino acid substitution | | | | SEQ ID NO: (nucleotide sequence) |
|---|---|---|---|---|---|
| | Ala2 | Thr133 | Phe136 | Asp199 | |
| 16 | Lys | — | — | — | 44 |
| 17 | Asn | — | — | — | 45 |
| 18 | — | Ala | — | — | 46 |
| 19 | — | Cys | — | — | 47 |
| 20 | — | Ser | — | — | 48 |
| 21 | — | — | Ala | — | 49 |
| 22 | — | — | Ser | — | 50 |
| 80 | — | — | Trp | — | 88 |
| 23 | — | — | — | Gln | 51 |
| 24 | — | — | — | Glu | 52 |
| 25 | — | — | — | His | 53 |
| 26 | — | — | — | Ser | 54 |
| 27 | — | — | — | Thr | 55 |
| 28 | — | — | — | Tyr | 56 |
| 81 | — | — | — | Leu | 89 |
| 82 | — | — | — | Met | 90 |
| 83 | — | — | — | Ile | 91 |

It is sufficient if the improved halohydrin epoxidase of the present invention consists of an amino acid sequence having one or more amino acid substitutions selected from (A) to (D) above, and preferably from (E) to (H) above. Therefore, the improved halohydrin epoxidase of the present invention include those consisting of an amino acid sequence having a combination of a plurality of characteristics selected from (A) to (H) above (i.e., the amino acid mutations (A) to (H)). Moreover, improved halohydrin epoxidases consisting of an amino acid sequence, in which the embodiments of the amino acid mutations in (A) to (H) above are retained, and in which any one of or a plurality of amino acid mutations selected from (i) to (iii) below is introduced into an amino acid sequence of a wild-type halohydrin epoxidase that is a base of an improved halohydrin epoxidase, are also within the range of the improved halohydrin epoxidase of the present invention:

(i) an amino acid mutation in which one or several amino acid residues selected from amino acid residues other than the amino acid residue which is one residue closer to the C-terminal end than the start amino acid residue, α14 residue in the amino acid sequence I, α15 residue in the amino acid sequence I and β21 residue in the amino acid sequence II are substituted with other amino acids;

(ii) an amino acid mutation in which one or several amino acid residues selected from amino acid residues other than the amino acid residue which is one residue closer to the C-terminal end than the start amino acid residue, amino acid residues contained in the amino acid sequence I and amino acid residues contained in the amino acid sequence II are deleted; and (iii) an amino acid mutation in which one or several arbitrary amino acid residues are inserted in a region, which consists of amino acid residues which are one or two residues closer to the C-terminal end than the start amino acid residue, and which excludes a region consisting of the amino acid sequences I and II.

In the embodiments of (i) to (iii) above, "one or several" means, for example, about 1 to 10, and preferably about 1 to 5.

In the present invention, the type of amino acid is sometimes represented by 3 letters or one letter of the alphabet. In addition, there is a case where 3 letters or one letter of the alphabet are described before or before and after a numerical character. This expresses the position of an amino acid residue and the types of amino acids before/after substitution. That is, unless otherwise specified, as described above, numerical characters indicate at what position numbers amino acid residue are present when defining the amino acid residue (usually methionine) encoded by the translation initiation codon as being at position-1. Further, 3 letters or one letter of the alphabet shown before a numerical character indicate an amino acid prior to amino acid substitution, and 3 letters or one letter of the alphabet shown after a numerical character indicate an amino acid after amino acid substitution (when it occurs). For example, an aspartic acid residue at position-207 may be described as "Asp207" or "D207", and when the aspartic acid residue at position-207 is substituted with histidine, it may be described as "Asp207His" or "D207H".

(III) Halohydrin Epoxidase Gene (III-1) Wild-Type Halohydrin Epoxidase Gene

Among wild-type halohydrin epoxidases, those whose gene sequence (nucleotide sequence) has been revealed have been registered in GenBank database provided by National Center for Biotechnology Information (NCBI) (http://www.ncbi.nlm.nih.gov/entrez/query.fcgi?db=Nucleotide) with the following Accession Numbers.

"Accession No. D90349": Nucleotide sequence of gene encoding HheA from *Corynebacterium* sp. strain N-1074
"Accession No. AF397297": Nucleotide sequence of gene encoding HheA$_{AD2}$ from *Arthrobacter* sp. strain AD2
"Accession No. D90350": Nucleotide sequence of gene encoding HheB from *Corynebacterium* sp. strain N-1074
"Accession No. AY044094": Nucleotide sequence of gene encoding HheB$_{GP1}$ from *Mycobacterium* sp. strain GP1
"Accession No. AF397296": Nucleotide sequence of gene encoding HheC from *Agrobacterium radiobacter* strain AD1
"Accession No. AF149769": Nucleotide sequence of gene encoding HalB from *Agrobacterium tumefaciens*

In the present invention, these are designated as "wild-type halohydrin epoxidase gene". In this regard, the word "wild-type" in the "wild-type halohydrin epoxidase gene" qualifies "halohydrin epoxidase", and it means that the amino acid sequence of halohydrin epoxidase is "wild-type". In the present invention, it is sufficient if the nucleotide sequence constituting the "wild-type halohydrin epoxidase gene" encodes a codon which can be utilized in a transformant host. The nucleotide sequence is not necessarily limited to those of the wild-type halohydrin epoxidase gene encoded on the genome DNA of original living organisms. Note that the wild-type halohydrin epoxidase gene encoding HheB($1^{st}$) described in "(II-1) Wild-type halohydrin epoxidase" is designated as HheB($1^{st}$) and the gene encoding HheB($2^{nd}$) is designated as HheB($2^{nd}$). The nucleotide sequence of HheB ($1^{st}$) is represented by SEQ ID NO: 29, and the nucleotide sequence of HheB($2^{nd}$) is represented by SEQ ID NO: 30.

Examples of methods for obtaining a wild-type halohydrin epoxidase gene whose nucleotide sequence has been revealed include a method in which: the genome DNA is prepared from an original living organism; a primer is designed based on the sequence information of a revealed wild-type halohydrin epoxidase gene; and a gene encoding the halohydrin epoxidase is amplified by means of PCR using the primer. Examples of original living organisms include strain N-1074, and this strain was deposited to the International Patent Organism Depositary, National Institute of Advanced Industrial Science and Technology (Chuo 6, Higashi 1-1-1, Tsukuba-shi, Ibaraki (the same applies to the following)) on Nov. 10, 1988 (Accession No. FERM BP-2643). It is also possible to chemically synthesize the full length of a wild-type halohydrin epoxidase gene utilizing, for example, a PCR method using synthetic oligoDNA (assembly PCR) based on the publicly-known gene sequence information. For example, a wild-type halohydrin epoxidase gene is divided into several regions (e.g., about 50 bases for each), and a plurality of oligonucleotides having an overlap (e.g., about 20 bases) with the adjacent region at both ends are designed and synthesized. The oligonucleotides are annealed to each other by PCR, thereby amplifying the wild-type halohydrin epoxidase gene.

According to need, the codon of the wild-type halohydrin epoxidase gene can be changed. Examples of means for changing the codon include a site-specific mutation induction method described, for example, in Molecular Cloning, A Laboratory Manual 2nd ed., Cold Spring Harbor Laboratory Press (1989); Current Protocols in Molecular Biology. John Wiley & Sons (1987-1997); etc, a kit for mutation introduction which utilizes a site-specific mutation induction method (e.g., QuickChange™ Site-Directed Mutagenesis Kit (Stratagene), GeneTailor™ Site-Directed Mutagenesis System (Invitrogen), and TaKaRa Site-Directed Mutagenesis System (Mutan-K, Mutan-Super Express Km, etc.: Takara Bio Inc.)) and the like. It is also possible to change the codon using a primer in which the codon is changed when performing a PCR method using synthetic oligoDNA (assembly PCR) as described above.

(III-2) Improved Halohydrin Epoxidase Gene

The improved halohydrin epoxidase gene of the present invention means a gene encoding the improved halohydrin epoxidase enzyme protein described in (II-2) above. The improved halohydrin epoxidase gene of the present invention is, for example, a gene encoding an improved halohydrin epoxidase having an amino acid sequence in which any one of or a plurality of amino acid mutations selected from (A) to (D) in (II-2) above are introduced into the wild-type halohydrin epoxidase consisting of the amino acid sequence represented by SEQ ID NO: 1 or 2, and is more preferably a gene encoding an improved halohydrin epoxidase having an amino acid sequence in which any one of or a plurality of amino acid mutations selected from (E) to (H) in (II-2) above are introduced. It is sufficient if the wild-type halohydrin epoxidase gene and the nucleotide sequence constituting the amino acid residue after the above-described introduction of amino acid mutation encode a codon which can be utilized in a transformant host. The nucleotide sequence is not necessarily limited to those of the wild-type halohydrin epoxidase gene encoded on the genome DNA of original living organisms. Note that both the wild-type halohydrin epoxidase gene HheB($1^{st}$) encoding HheB($1^{st}$) and the wild-type halohydrin epoxidase gene HheB($2^{nd}$) encoding HheB($2^{nd}$), which are described in (II-1) above, can be used as a wild-type halohydrin epoxidase gene to be a base for obtaining an improved halohydrin epoxidase gene. When a wild-type halohydrin epoxidase is HheB ($1^{st}$) from *Corynebacterium* sp. strain N-1074 having the amino acid sequence represented by SEQ ID NO: 1, more specific and preferred examples of embodiments of the "improved halohydrin epoxidase gene" of the present invention include improved halohydrin epoxidase genes having any of the nucleotide sequences represented by SEQ ID NOs: 31-43 and 84-87. When a wild-type halohydrin epoxidase is HheB($2^{nd}$) from *Corynebacterium* sp. strain N-1074 having the amino acid sequence represented by SEQ ID NO: 2, more specific and preferred examples include improved halohydrin epoxidase genes having any of the nucleotide sequences represented by SEQ ID NOs: 44-56 and 88-91.

It is sufficient if the improved halohydrin epoxidase gene of the present invention is a gene encoding an amino acid sequence of an improved halohydrin epoxidase into which one or more amino acid mutations selected from (A) to (H) in (II-2) above are introduced. Therefore, the improved halohydrin epoxidase gene of the present invention include genes encoding an amino acid sequence of an improved halohydrin epoxidase having a combination of a plurality of characteristics selected from (A) to (H) in (II-2) above (i.e., the amino acid mutations (A) to (H)). Moreover, genes encoding an amino acid sequence of an improved halohydrin epoxidase, in which the embodiments of the amino acid mutations in (A) to (H) in (II-2) above are retained, and in which any of the amino acid mutations selected from (i) to (iii) in (II-2) above is introduced into an amino acid sequence of a wild-type halohydrin epoxidase that is a base of an improved halohydrin epoxidase, are also within the range of the improved halohydrin epoxidase gene of the present invention.

Furthermore, the improved halohydrin epoxidase gene of the present invention also includes DNAs, which hybridize, under stringent conditions, to a DNA consisting of a nucleotide sequence complementary to a nucleotide sequence encoding an amino acid sequence of an improved halohydrin epoxidase into which any one of or a plurality of amino acid mutations selected from (A) to (H) in (II-2) above are introduced. Such DNAs can be obtained, for example, from cDNA library and genomic library by means of a publicly-known hybridization method such as a colony hybridization method, a plaque hybridization method and Southern blotting using, as a probe, a DNA of an improved halohydrin epoxidase gene consisting of a nucleotide sequence encoding an amino acid sequence into which any one of or a plurality of amino mutations selected from (A) to (H) above are introduced or a complementary sequence thereof, or a fragment thereof. Regarding libraries, a library prepared using a publicly-known method can be utilized, and a commercially-available cDNA library and genomic library can also be utilized.

The "stringent conditions" mean conditions at the time of washing after hybridization, in which: the salt concentration is 300 to 2000 mM, and preferably 600 to 900 mM; and the temperature is 40 to 75° C., and preferably 65° C. (e.g., 2×SSC, 50° C.). Regarding the salt concentration of buffer and the temperature as well as other conditions such as the concentration of probe, probe length, reaction time, etc., those skilled in the art would be able to set suitable conditions for obtaining a DNA which hybridizes, under stringent conditions, to a DNA consisting of a nucleotide sequence complementary to a nucleotide sequence encoding an amino acid sequence of an improved halohydrin epoxidase into which any one of or a plurality of amino acid mutations selected from (A) to (H) in (II-2) above are introduced.

Regarding detailed procedures of hybridization, Molecular Cloning, A Laboratory Manual 2nd ed. (Cold Spring Harbor Laboratory Press (1989)), etc. can be referred to. Examples of DNAs which hybridize include DNAs comprising a nucleotide sequence having at least 40% identity, preferably at least 60% identity, and more preferably at least 90% identity to a nucleotide sequence encoding an amino acid sequence into which any one of or a plurality of amino acid mutations selected from (A) to (H) in (II-2) above are introduced, and partial fragments thereof.

In the present invention, as a method for preparing an improved halohydrin epoxidase gene, any already-known method for introducing mutation may be employed, and usually, a publicly-known method can be used. Examples of such methods include: a method in which a site-specific substitution is caused based on a wild-type halohydrin epoxidase gene utilizing a commercially-available kit; and a method in which a gene DNA fragment is selectively cleaved and then a selected oligonucleotide is removed/added, followed by linking. These site-specific mutation induction methods are described, for example, in "Molecular Cloning, A Laboratory Manual 2nd ed." (Cold Spring Harbor Press (1989)); "Current Protocols in Molecular Biology" (John Wiley & Sons (1987-1997)); Kunkel, Proc. Natl. Acad. Sci. USA, 82: 488-492 (1985); Kramer and Fritz Method. Enzymol., 154: 350-367 (1987); and Kunkel, Method. Enzymol., 85: 2763-2766 (1988). Recently, kits for mutation introduction utilizing a site-specific mutation induction method based on the Kunkel method. Gapped duplex method or the like (e.g., Quick-Change™ Site-Directed Mutagenesis Kit (Stratagene), GeneTailor™ Site-Directed Mutagenesis System (Invitrogen), and TaKaRa Site-Directed Mutagenesis System (Mutan-K, Mutan-Super Express Km, etc.: Takara Bio Inc.)) have been developed, and these kits can also be used. When a target position for mutation introduction is positioned adjacent to a restriction enzyme site, which can be easily digested/linked, in a target gene sequence, a primer into which a target mutation is introduced (synthetic oligoDNA) is used to perform PCR, thereby easily obtaining a gene DNA fragment into which the target mutation is introduced. Alternatively, extension may be performed using a PCR method using synthetic oligoDNA (assembly PCR), thereby obtaining a synthetic gene. Moreover, an improved halohydrin epoxidase gene can also be obtained from a wild-type halohydrin epoxidase gene using a method of random mutation introduction such as: a method of bringing an agent as a mutation source such as hydroxylamine and nitrous acid into contact for providing action; a method for inducing mutation by ultraviolet irradiation; and a method for introducing random mutation using PCR (polymerase chain reaction).

(IV) Recombinant Vector, Transformant (IV-1) Recombinant Vector

In order to express the improved halohydrin epoxidase gene of the present invention obtained using the above-described method in a host, a transcription promoter is inserted upstream of the gene and a terminator is inserted downstream of the gene to construct an expression cassette, and this cassette can be inserted into an expression vector. Alternatively, when a transcription promoter and a terminator already exist in an expression vector into which the improved halohydrin epoxidase gene should be introduced, it is not necessary to construct an expression cassette, and the mutated gene may be inserted between the promoter and the terminator in the vector. In order to insert the improved halohydrin epoxidase gene into a vector, a method using a restriction enzyme, a method using topoisomerase or the like can be utilized. If necessary at the time of insertion, a suitable linker may be added. In the present invention, the operation for insertion as described above may be performed together with the operation for preparing the improved halohydrin epoxidase gene. That is, using a primer having a nucleotide sequence subjected to substitution to provide a nucleotide sequence encoding another amino acid, PCR is performed utilizing, as a template, a recombinant vector in which a wild-type halohydrin epoxidase gene is cloned, and an amplified product obtained can be incorporated into a vector.

The type of promoter is not particularly limited as long as the promoter enables appropriate expression in a host. Examples of promoters which can be utilized in *E. coli* hosts include trp promoter of tryptophan operon, lac promoter of lactose operon, and PL promoter and PR promoter from lambda phage. Modified and designed sequences such as tac promoter and trc promoter can also be utilized. Examples of promoters which can be utilized in *Bacillus subtilis* hosts include gluconate synthase promoter (gnt), alkaline protease promoter (apr), neutral protease promoter (npr), and α-amylase promoter (amy). Examples of promoters which can be utilized in *Rhodococcus* hosts include promoters associated with nitrilase expression regulatory gene from *Rhodococcus erythropolis* strain SK92-B1 included in the expression vector pSJ034. pSJ034 is a plasmid expressing nitrile-hydratase in a bacterium of the genus *Rhodococcus*, and can be prepared from pSJ023 using a method indicated in Japanese Laid-Open Patent Publication No. 10-337185. Note that pSJ023 was deposited to International Patent Organism Depositary, National Institute of Advanced Industrial Science and Technology (Chuo 6, Higashi 1-1-1, Tsukuba-shi, Ibaraki) on Mar. 4, 1997, as transformant ATCC12674/pSJ023 (Accession No. FERM BP-6232).

Terminators are not necessarily required, and the type of terminator is not particularly limited. Examples of terminators include those which are ρ factor-independent such as lipoprotein terminator, trp operon terminator and rrnB terminator.

As nucleotide sequences which are important for translation into amino acids, ribosome-binding sequences such as SD sequence and Kozak sequence are known. Such sequences can be inserted upstream of a mutated gene. A SD sequence (when using a prokaryote as a host) and a Kozak sequence (when using a eukaryotic cell as a host) may be added by means of the PCR method or the like. Examples of SD sequences include sequences derived from *E. coli, Bacillus subtilis* or the like, but the SD sequence is not particularly limited as long as it is a sequence which functions in a desired host of *E. coli, Bacillus subtilis* or the like. For example, a consensus sequence consisting of 4 or more contiguous bases in a sequence complementary to the 3'-terminal region of 16S ribosome RNA may be prepared by means of DNA synthesis for utilization.

In general, a vector includes a factor for selecting a transformant of interest (selection marker). Examples of selection markers include drug-resistant genes, auxotrophic complementary genes and genes conferring assimilation ability, and selection is made depending on the purpose, the type of host, etc. Examples of drug-resistant genes for use as a selection marker in *E. coli* include ampicillin-resistant genes, kanamycin genes, dihydrofolate reductase genes and neomycin-resistant gene.

The vector to be used in the present invention is not particularly limited as long as it retains the above-described mutated gene, and various vectors which are suitable for various types of hosts respectively can be used. Examples of vectors include plasmid DNA, bacteriophage DNA, retrotransposon DNA and artificial chromosome DNA. For example, when using *E. coli* as a host, the following vectors having a region which can autonomously replicate in *E. coli* can be used: pTrc99A (Centraalbureau voor Schimmelcultures (CBS), Netherlands; http://www.cbs.knaw.nl/), pUC19 (Takara Bio Inc., Japan), pKK233-2 (Centraalbureau voor Schimmelcultures (CBS), Netherlands; http://www.cbs.knaw.nl/), pET-12 (Novagen, Germany), pET-26b (Novagen. Germany), etc. If required, these vectors can be modified to be used. Further, expression vectors having high expression efficiency can be used (for example, expression vector pTrc99A or pKK233-2 having trc promoter or lac operator).

Recombinant vectors including the above-described improved halohydrin epoxidase gene are within the scope of the present invention. Specific examples of recombinant vectors including the improved halohydrin epoxidase gene include the following vectors which are exemplified herein: pSTK002, pSTK003, pSTT002, pSTT003, pSTT002-T133A, pSTT002-T136C, pSTT002-T133S, pSTT002-F136A, pSTT002-F136S, pSTT002-F136W, pSTT002-D199Q, pSTT002-D199E, pSTT002-D199H, pSTT002-D199S, pSTT002-D199T, pSTT002-D199Y, pSTT002-D199L, pSTT002-D199M, pSTT002-D199I, etc.

(IV-1) Transformant

By transforming or transducing the recombinant vector of the present invention into a host, a transformant or transductant (hereinafter collectively referred to as "transformant") is prepared. The transformant is also within the scope of the present invention.

The host to be used in the present invention is not particularly limited as long as it can express an improved halohydrin epoxidase of interest after the above-described recombinant vector is introduced therein. Examples of hosts include bacteria (e.g., *E. coli, Bacillus subtilis*, and bacteria of the genus *Rhodococcus*), yeasts (*Pichia, Saccharomyces*), fungi (*Aspergillus*), animal cells, insect cells and plant cells.

In the present invention, when using a bacterium as a host. *E. coli* and bacteria of the genus *Rhodococcus* are preferably used. Examples of *E. coli* include *E. coli* strain K-12 and strain B, and strains JM109, XL1-Blue and C600 derived from these wild-type strains. In particular, in the case of using the above-described lac promoter of lactose operon or a promoter derived therefrom as an expression promoter, when using a host having the lad repressor gene, expression becomes the inducible type (induction by IPTG or the like), and when using a host without the lacI repressor gene, expression becomes the constitutive type. Therefore, a host according to need can be utilized. These strains can be easily obtained from the American Type Culture Collection (ATCC) or the like. Examples of grass bacilli include *Bacillus subtilis*. Examples of bacteria of the genus *Rhodococcus* include: strains ATCC999, ATCC12674, ATCC17895, ATCC15998, ATCC33275, ATCC184, ATCC4001, ATCC4273, ATCC4276, ATCC9356, ATCC12483, ATCC14341, ATCC14347, ATCC14350, ATCC15905, ATCC15998, ATCC17041, ATCC19149, ATCC19150, ATCC21243, ATCC29670, ATCC29672. ATCC29675, ATCC33258, ATCC13808, ATCC17043, ATCC19067, ATCC21999, ATCC21291, ATCC21785, ATCC21924, IFO14894, IFO3338, NCIMB11215, NCIMB11216, and JCM3202 of *Rhodococcus rhodochrous*; strain J1 of *Rhodococcus rhodochrous* (Accession No. FERM BP-1478); strain IFO14531 of *Rhodococcus globerulus*; strains JCM6162 and JCM6164 of *Rhodococcus luteus*; strains IFO12538 and IFO12320 of *Rhodococcus erythropolis*; and strains IFO3730 and JCM1313 of *Rhodococcus equi*. Preferably, strain J1 of *Rhodococcus rhodochrous* (Accession No. FERM BP-1478) is used. The above-described ATCC strains can be obtained from the American Type Culture Collection. The IFO strains can be obtained from NITE Biological Resource Center (NBRC). The JCM strains can be obtained from Japan Collection of Microorganisms, RIKEN Bioresource Center. The FERM strains can be obtained from the International Patent Organism Depositary, National Institute of Advanced Industrial Science and Technology.

The method for introducing a recombinant vector into a bacterium is not particularly limited as long as it is a method for introducing a DNA into a bacterium. Examples thereof include a method using calcium ion and the electroporation method. When using a yeast as a host, for example, *Saccharomyces cerevisiae, Schizosaccharomyces pombe, Pichia pastoris* or the like can be used. The method for introducing a recombinant vector into a yeast is not particularly limited as long as it is a method for introducing a DNA into a yeast. Examples thereof include the electroporation method, spheroplast method and lithium acetate method. When using an animal cell as a host, a monkey cell COS-7, Vero, CHO cell, mouse L cell, rat GH3, human FL cell or the like can be used. Examples of methods for introducing a recombinant vector into an animal cell include the electroporation method, calcium phosphate method and lipofection method. When using an insect cell as a host, Sf9 cell, Sf21 cell or the like can be used. Examples of methods for introducing a recombinant vector into an insect cell include the calcium phosphate method, lipofection method and electroporation method. When using a plant cell as a host, examples thereof include, but are not limited to, *nicotiana tabacum* BY-2 cell, etc. Examples of methods for introducing a recombinant vector into a plant cell include the *Agrobacterium* method, particle gun method, PEG method and electroporation method.

Transformants obtained from recombinant vectors including the above-described improved halohydrin epoxidase gene are within the scope of the present invention. Specific examples of transformants obtained from recombinant vectors including the improved halohydrin epoxidase gene include the following transformants which are exemplified herein: JM109/pSTK002, JM109/pSTK003, JM109/pSTT002, JM109/pSTT003, JM109/pSTT002-T133A, JM109/pSTT002-T133C, JM109/pSTT002-T133S, JM109/pSTT002-F136A, JM109/pSTT002-F136S, JM109/pSTT002-F136W, JM109/pSTT002-D199Q, JM109/pSTT002-D199E, JM109/pSTT002-D199H, JM109/pSTT002-D199S, JM109/pSTT002-D199T, JM109/pSTT002-D199Y, JM109/pSTT002-D199L, JM109/pSTT002-D199M, JM109/pSTT002-D199I, etc.

(V) Method for Producing the Improved Halohydrin Epoxidase

In the present invention, the improved halohydrin epoxidase can be produced, as a culture product per se obtained by culturing the above-described transformant, or by collecting from the culture. As used herein, the "culture" means both products obtained by culturing a transformant which produces the improved halohydrin epoxidase and products derived therefrom (e.g., culture solution, culture supernatant fluid, higher eukaryotic or microbial cells, suspension containing higher eukaryotic or microbial cells, a disintegrated product of higher eukaryotic or microbial cells, crude enzyme solution, and products obtained by treatment thereof). Cultures obtained by culturing the transformant of the present invention are within the scope of the present invention. The method for culturing the transformant of the present invention can be carried out according to a usual method used for culture of a host. An improved halohydrin epoxidase of interest is accumulated in any of the above-described cultures.

A medium for culturing the transformant of the present invention may be natural or synthetic as long as it is a medium containing a carbon source, a nitrogen source, inorganic salt or the like by which a host can have assimilation capacity, in which culture of the transformant can be efficiently performed. Examples of carbon sources include: carbohydrates such as glucose, galactose, fructose, sucrose, raffinose and starch; organic acids such as acetic acid and propionic acid; and alcohols such as ethanol and propanol. Examples of nitrogen sources include: ammonium salts of inorganic acid or organic acid such as ammonia, ammonium chloride, ammonium sulfate, ammonium acetate and ammonium phosphate; and other nitrogen-containing compounds. Peptone, yeast extract, meat extract, corn steep liquor, various amino acids, etc. may also be used. Examples of inorganic substances include monopotassium phosphate, dipotassium phosphate, magnesium phosphate, magnesium sulfate, sodium chloride, ferrous sulfate, manganese sulfate, zinc sulfate, copper sulfate, and calcium carbonate. According to need, an antifoamer may be added in order to prevent foam formation in culture. Further, according to need, vitamins, etc. may be suitably added. During culture, antibiotics such as ampicillin and tetracycline may be added to a medium according to need.

Culture may be performed under selective pressure in order to prevent dropout of a vector and a gene of interest during culture. That is, in the case where the selection marker is a drug-resistant gene, a corresponding agent may be added to a medium, and in the case where the selection marker is an auxotrophic complementary gene, a corresponding nutritional factor may be removed from a medium. When the selection marker is a gene conferring assimilation ability, a corresponding factor for assimilation capacity may be added as an only factor according to need. For example, in the case where $E.$ $coli$ which is transformed with a vector including an ampicillin-resistant gene is cultured, ampicillin may be added to a medium during culture according to need.

In the case where a transformant, which is transformed with an expression vector in which an inducible promoter is used as a promoter, is cultured, an inducer may be added to a medium according to need. For example, when a transformant, which is transformed with an expression vector having a promoter that is inducible with isopropyl-$\beta$-D-thiogalactoside (IPTG), is cultured, IPTG, etc. may be added to a medium. When a transformant, which is transformed with an expression vector in which a trp promoter that is inducible with indoleacetic acid (IAA) is used, is cultured, IAA, etc. may be added to a medium.

Culture conditions of transformant are not particularly limited as long as the productivity of an improved halohydrin epoxidase of interest and growth of a host are not inhibited thereby. The culture temperature is generally 10 to 45° C., preferably 10 to 40° C., more preferably 15 to 40° C., and even more preferably 20 to 37° C. According to need, the temperature may be changed during culture. Culture time is about 5 to 120 hours, preferably about 5 to 100 hours, more preferably about 10 to 100 hours, and even more preferably about 15 to 80 hours. Adjustment of pH is carried out using an inorganic or organic acid, an alkali solution or the like. In the case of $E.$ $coli$, pH is usually adjusted to 6 to 9. Examples of culture methods include solid culture, static culture, shaking culture and stirred aerobic culture.

In particular, in the case where $E.$ $coli$ transformant is cultured, it is preferably carried out under an aerobic condition by means of shaking culture or stirred aerobic culture (jar fermenter). In this case, culture may be performed using a usual solid culture method, but is preferably performed by employing a liquid culture method as much as possible. Examples of media to be used in culture include those in which one or more types of inorganic salts (e.g., sodium chloride, monopotassium phosphate, dipotassium phosphate, magnesium sulfate, magnesium chloride, ferric chloride, ferric sulfate, and manganese sulfate) are added to one or more types of nitrogen sources (e.g., yeast extract, triptone, polypeptone, corn steep liquor, and steep liquor of soybean or wheat bran) and saccharine materials, vitamins, etc. are further added suitably thereto according to need. It is appropriate that the initial pH of a medium is adjusted to 7 to 9. Further, the culture is performed at 5 to 40° C., and preferably 10 to 37° C. for 5 to 100 hours. The culture is preferably carried out by means of stirred and submerged aerobic culture, shaking culture, static culture, feeding culture or the like. In particular, when producing the improved halohydrin epoxidase on industrial scale, stirred aerobic culture may be utilized. The operation method of stirred aerobic culture is not particularly limited, and any of batch culture, fed-batch culture (semi-batch culture) and continuous culture may be employed. In particular, when the productivity per apparatus, per time, per cost, or per operation is desired to be increased by means of high concentration culture, fed-batch culture may be employed. The composition of components of the fed-medium to be used in fed-batch culture may be the same as that of components of the batch-medium, or the composition may be changed therefrom. However, it is preferred that the concentration of the fed-medium components is higher than that of the batch-medium. The volume of the fed-medium is not particularly limited, but usually, a volume of 1/2 or smaller of the batch-medium may be added. Examples of methods for adding a fed-medium (feeding mode) include constant feeding method, exponential feeding method, stepwise-increasing feeding method, specific growth-rate control feeding method, pH-stat feeding method, DO-stat feeding method, glucose concentration control feeding method, acetate concentration monitoring feeding method, and fuzzy neural network feeding method (Trends in Biotechnology (1996), 14, 98-105). However, there is no specific limitation thereon as long as desired halohydrin epoxidase activity can be obtained. Note that timing of the termination of culture at the time of performing fed-batch culture is not required to be limited to the point after the completion of feeding of the fed-medium, and culture may be continued according to need and terminated at the point of obtaining the highest halohydrin epoxidase activity per transformant.

As a medium for culturing a transformant obtained using an animal cell as a host, a generally-used RPMI 1640 medium, DMEM medium, or mediums in which fetal bovine serum or the like is added to any of the aforementioned media, etc. may be used. The culture is usually performed in the presence of 5% $CO_2$ at 37° C. for 1 to 30 days. During culture, antibiotics such as kanamycin and penicillin may be added to the medium according to need. When the transformant is a plant cell or plant tissue, the culture can be performed using usual media for plant culture such as MS based media, LS based media, etc. As the culture method, any of the usual solid culture method and liquid culture method may be employed.

When performing culture under the above-described culture conditions, the improved halohydrin epoxidase of the present invention can be accumulated in at least any one of the above-described cultures, i.e., culture solution, culture supernatant fluid, higher eukaryotic cells, microbial cells, and a disintegrated product of higher eukaryotic or microbial cells.

After culture, when the improved halohydrin epoxidase is produced in a microbial or higher eukaryotic cells, the microbial or higher eukaryotic cells may be used as it is as a catalyst for the substance production, and alternatively, the microbial or higher eukaryotic cells may be disintegrated, thereby collecting an improved halohydrin epoxidase of interest. In each case, if necessary, the medium can be removed and washed by means of operation for solid-liquid separation such as centrifugal separation and membrane filtration. Centrifugal separation is not particularly limited as long as it can provide the centrifugal force to precipitate microbial or higher eukaryotic cells, and a cylindrical type apparatus, a separating plate type apparatus, etc. may be utilized. Centrifugal separation can be performed, for example, with the centrifugal force of about 500 to 20,000 G. As membrane filtration which can be utilized in the process, both a microfiltration (MF) membrane and an ultrafiltration (UF) membrane may used as long as desired solid-liquid separation can be accomplished. Usually, a microfiltration (MF) membrane is preferably used. For example, based on the flow direction, microfiltration can be classified into the dead-end mode and the cross-flow mode (tangential flow method), and based on the way to apply pressure, it can be classified into the gravity-based method, pressure-based method, vacuum-based method, centrifugal force-based method, etc., and based on the operation method, it can be classified into the batch-based method, continuous method, etc. Any of the above-described methods can be utilized as long as the solid-liquid separation operation can be carried out thereby. Materials for MF membranes can be roughly classified into polymer membranes, ceramic membranes, metallic membranes, and complex membranes thereof, and there is no particular limitation thereon as long as the materials do not reduce the improved halohydrin epoxidase activity or the activity recovery ratio at the time of solid-liquid separation operation. In particular, polymer membranes such as polysulfone, polyether sulfone, polytetrafluoroethylene, polyvinylidene fluoride, polyvinyl chloride, polypropylene, polyolefine, polyethylene, polycarbonate, polyacrylonitrile, mixed cellulose ester, cuprammonium regenerated cellulose ester, polyimide, nylon, Teflon (registered trademark), etc. are preferably used. The pore size of the membrane is sufficient if microbial or higher eukaryotic cells can be captured and concentration operation can be performed with the size. Usually, the pores size may be about 0.1 to 0.5 μm.

At the time of the solid-liquid separation operation by means of centrifugal separation and membrane filtration, water, or according to need, a buffer solution and/or isotonic solution may be added thereto, thereby performing dilution and wash. The buffer solution to be used is not particularly limited as long as it does not reduce the improved halohydrin epoxidase activity or the activity recovery ratio at the time of solid-liquid separation operation. For example, it is sufficient if the buffer solution has the salt concentration of about 5 to 500 mM, and preferably about 5 to 150 mM, and pH of about 5 to 9. Examples of components of the buffer solution include tris(hydroxymethyl)aminomethane (Tris), sodium phosphate or potassium salt, citrate salt, and acetate. Specific examples thereof include 20 mM Tris-sulfuric acid buffer solution (pH 8), and 20 mM sodium phosphate buffer solution (pH 7). Examples of isotonic solutions include 0.7 to 0.9% sodium chloride solution. In addition, if any, substances which can stabilize the improved halohydrin epoxidase, etc. may also be added.

After performing the above-described removal of medium and washing operation, microbial or higher eukaryotic cells may be resuspended in water, or according to need, a buffer solution and/or isotonic solution, thereby preparing a suspension containing microbial or higher eukaryotic cells. The suspension containing microbial or higher eukaryotic cells may be used as it is as a catalyst for the substance production, but according to need, it may be used after treated. In one example of the treatment method, a surfactant is added to a culture obtained by culture as described above so that the final concentration of the surfactant becomes 0.01 to 10%, and the mixture may be stirred at a temperature at which halohydrin epoxidase is not deactivated. The final concentration of the surfactant is preferably 0.05 to 1%, and particularly preferably 0.1 to 0.5%. The treatment temperature is preferably 0 to 40° C., and particularly preferably 4 to 20° C. Regarding the treatment time, it is sufficient if the effect of the treatment of cells is exhibited within the time frame, and preferably 15 minutes to 24 hours, and particularly preferably 30 minutes to 2 hours. As the surfactant, an anionic surfactant, a cationic surfactant or a nonionic surfactant may be used. As the anionic surfactant, sodium dodecyl sulfate or the like may be used. As the cationic surfactant, benzethonium chloride or the like may be used. As the nonionic surfactant, Triton X-100 or the like may be used. Cells after treated with the surfactant may be used after washed with a buffer, or may also be used directly (without washing). Moreover, microbial or higher eukaryotic cells can be directly treated with the surfactant or the like without performing the above-described removal of medium and washing operation. Furthermore, microbial or higher eukaryotic cells can be immobilized to be used. Specific examples thereof include a product in which higher eukaryotic or microbial cells after culture are encapsulated in gel such as acrylamide, and a product in which higher eukaryotic or microbial cells are supported on inorganic carriers such as alumina, silica, zeolite and diatom earth.

Alternatively, an improved halohydrin epoxidase of interest can be collected by disintegrating microbial or higher eukaryotic cells. Examples of methods for disintegrating microbial or higher eukaryotic cells include: ultrasonic treatment; high-pressure treatment using the French press, homogenizer or the like; treatment of grinding down by friction using a bead mill; impact treatment using an apparatus for impact disintegration; enzyme treatment using lysozyme, cellulase, pectinase or the like; freezing and thawing treatment; treatment with hypotonic fluid; and lysis induction treatment using phage. These methods can be utilized solely or in combination according to need. When disintegrating microbial or higher eukaryotic cells on industrial scale, it is preferred that high-pressure treatment, treatment of grinding down by friction or impact treatment is mainly utilized in view of the operability, recovery rate, cost, etc. Depending on circumstances, enzyme treatment, etc. may be used in combination with these physically-treating operations for disintegration. In each of the disintegration treatment methods, operation conditions are not particularly limited as long as the recovery rate of the improved halohydrin epoxidase from microbial or higher eukaryotic cells is sufficiently high. "Sufficiently high recovery rate of the improved halohydrin epoxidase" is, for example, preferably 85% or higher, more preferably 90% or higher, even more preferably 95% or higher, and most preferably 99% or higher.

The treatment of grinding down by friction using a bead mill can be usually carried out by filling the bead mill to about 80 to 85% with, for example, beads having a density of 2.5 to 6.0 g/cm$^3$ and a size of 0.1 to 1.0 mm. Regarding the operation mode, both batch operation and continuous operation can be employed. The concentration of microbial or higher eukaryotic cells is not particularly limited. However, for example, it is sufficient if the concentration is about 6 to 12% in the case of bacterium, and about 14 to 18% in the case of yeast.

When performing the high-pressure treatment, the process pressure is not particularly limited as long as the recovery rate of the improved halohydrin epoxidase from microbial or higher eukaryotic cells is sufficiently high. For example, disintegration can be performed with pressure of about 40 to 150 MPa. The concentration of microbial or higher eukaryotic cells is not particularly limited. However, for example, it is sufficient if the concentration is about 20% or lower. According to need, the disintegration efficiency and the operation efficiency can be improved by performing a multistage treatment (e.g., arranging apparatuses in series, and using an apparatus having a multiple-stage structure). Usually, the temperature is increased by 2 to 3° C. per 10 MPa of process pressure. Therefore, it is preferred that cooling treatment is performed according to need.

In the case of the impact treatment, for example, slurry of microbial or higher eukaryotic cells to be disintegrated is subjected to rapid spray freezing treatment in advance (freezing speed: e.g., several thousand degrees per minute) to obtain frozen fine particles thereof (e.g., 50 μm or less), and the obtained particles are impacted on an impact plate using high-speed carrier gas (e.g., about 300 m/s), thereby disintegrating the microbial or higher eukaryotic cells.

As a result of the above-described treatment for disintegrating microbial or higher eukaryotic cells, when it becomes difficult to handle the obtained product due to increase in the viscosity of the treatment solution caused by effusion of nucleic acids in cells, or when it is effective in improving the activity recovery ratio in the later step of residue separation, removal or degradation of nucleic acid is performed according to need, thereby expecting reduction in the viscosity of the treatment solution and the improvement of the activity recovery ratio in the step of residue separation. As the method for removing or degrading nucleic acids in a disintegrated product of cell, any method may be employed as long as it is a method in which the improved halohydrin epoxidase activity or the activity recovery ratio is not reduced and nucleic acids can be removed or degraded. Examples thereof include: the method in which nucleic acids are precipitated by adding protamine sulfate or streptomycin to the disintegrated product of cell; the method in which nucleic acids are degraded using a nucleolytic enzyme; and the method in which liquid-liquid separation is performed using dextran-polyethylene glycol (as described in *Seikagaku Jikken Kota* (Biochemical Experiment), Volume 5, pages 200-201). Moreover, there is a case where further addition of a physical disintegration treatment is effective. Among the above-described methods, in particular, when nucleic acids are desired to be rapidly disintegrated without complicated processes, the method in which nucleic acids are degraded using a nucleolytic enzyme can be employed. As the nucleolytic enzyme to be used in the nucleolytic enzyme treatment, any enzyme may be employed as long as it at least acts on deoxyribonucleic acid (DNA), has the ability to catalyze the nucleolytic degradation reaction, and reduces the DNA polymerization degree. A nucleolytic enzyme which originally exists in the transformant cell may be utilized. Alternatively, an exogenous nucleolytic enzyme may be added. Examples of nucleolytic enzymes to be added include bovine spleen-derived DNaseI (Takara Bio Inc. Japan), porcine spleen-derived DNaseII (Wako Pure Chemical Industries. Ltd. Japan), *Serratia marcescens*-derived nucleolytic enzyme Benzonase (registered trademark) Nuclease (Takara Bio Inc., Japan), and Nuclease from *Staphylococcus aureus* (Wako Pure Chemical Industries. Ltd., Japan). The amount of enzyme to be added varies depending on the type of enzyme and the definition of the number of units (U), but those skilled in the art would be able to suitably set the amount. According to need, cofactors such as magnesium, which are required for the nucleolytic enzyme, may be added to the enzyme solution. The treatment temperature varies depending on the type of nucleolytic enzyme used. When a nucleolytic enzyme derived from mesophilic organisms is used, usually, the temperature is preferably set to 20 to 40° C.

When the residue of the disintegrated microbial or higher eukaryotic cells is required to be removed from the obtained disintegrated products, for example, removal can be performed by means of centrifugation, filtration (dead-end mode or the cross-flow mode), etc.

The centrifugation operation can be performed in a manner similar to that described above. When the amount of the residue of the disintegrated microbial or higher eukaryotic cells is very small and precipitation thereof cannot be easily performed, a flocculant may be used according to need, thereby increasing the residue precipitation efficiency. Examples of organic polymer flocculants include cationic flocculants, anionic flocculants, amphoteric flocculants and nonionic flocculants (based on ionicity), or include acryl type, polyethyleneimine, condensed polycation (polyamine), dimethyldiallylammonium chloride, chitosan, etc. (based on components). As the flocculant to be used in the present invention, any flocculant may be used as long as it does not reduce the improved halohydrin epoxidase activity or the activity recovery ratio and can improve the residue separation efficiency. Examples of water-soluble acrylic monomers, which may be components of acrylic flocculants, include acrylamide, sodium acrylate, sodium acrylamide-2-methylpropanesulfonate, dimethylaminoethyl-methacrylate, methacryloyloxyethyl-trimethylammonium-chloride, methacryloyloxyethyl-benzyldimethyl-ammonium chloride, dimethylaminoethyl-acrylate, acryloyloxyethyl-trimethylammonium-chloride, dimethylaminopropyl-acrylamide, acrylamide propyl-trimethylammonium-chloride, and polyamidine-chloride. Single polymers of these monomers, copolymers of these monomers with various compositions, and high molecular modified products of these monomers are included in examples of acrylic flocculants. In particular, typical examples of cationic polymer flocculants include polyaminoalkylmethacrylates, copolymerized products of polyaminoalkylmethacrylate and acrylamide, Mannich modified products of polyacrylamide, polydimethyldiallylammonium salts, polyvinylimidazolines, polyacrylamides, and amine-based polycondensated products, and many such products have already been commercialized. Examples of major products include: Sanpoly K-601, K-602 (main component: polyamine, Sankyo Kasei); Kuriflock LC-599 (main component: polyamine and polyamide, Kurita Water); Hymolock M-166, M-566, M-966 (main component: acrylamide modified product, Kyoritu Organic Industry); Uniflocker UF-301, UF-304, UF-305 (main component: polyacrylamide, Unitika); UF-330, UF-340 (main component:

aminomethacrylic acid ester, Unitika); UF-505 (main component: dicyano amine, Unitika); Ryufloc C-110 (main component: polyamine, Dainippon Ink & Chemicals); and Purifloc C-31 (main component: polyamine, Dow Chemical). Further, K-400 series, KM-200 series, KM-1200 series, KAM-200 series, KD-200 series, KP-000 series, KP-100 series, KP-200 series, KP-300 series, KP-500 series, KP-1200 series, KA-000 series, KA-200 series, KA-300 series, KA-400 series, KA-600 series, KA-700 series and KA-800 series manufactured by DiaNitrix (Japan) may also be used. These flocculants may be used solely or in combination. Any of the above-described flocculants may be used in the present invention as long as it does not reduce the improved halohydrin epoxidase activity or the activity recovery ratio and can improve the residue separation efficiency. Specifically, for example, K-403B, K-408, K-415, etc. manufactured by DiaNitrix (Japan) may be used. The amount of flocculant to be added varies depending on the type of flocculant or the microbes and the state of the disintegrated products. For example, the flocculant may be used at a concentration of 1/200-1/5, and preferably 1/100-1/10, relative to the dry weight % concentration of the disintegrated microorganism. The flocculant may be added, for example, as follows: the flocculant is dissolved in water in advance, and thereafter the mixture is added to the disintegrated product of microbial or higher eukaryotic cells, and the obtained mixture is allowed to stand or stirred for at least about 5 minutes to 24 hours, and preferably about 30 minutes to 10 hours. The temperature at that time is, for example, 0 to 60° C., preferably 0 to 50° C., and more preferably 0 to 40° C. When pH adjustment is required, an inorganic salt may be suitably added at a final concentration of 5 to 200 mM to buffer the liquid. Alternatively, according to need, a substance which stabilizes the improved halohydrin epoxidase may be added to the liquid.

When the residue is separated by filtration, either a microfiltration (MF) membrane or an ultrafiltration (UF) membrane may be used as along as the desired separation of residue can be achieved. Usually, it is preferable to use a microfiltration (MF) membrane. Any MF membrane may be used as long as it is capable of separation of residue as described above. The pore size of the membrane is not particularly limited as long as it allows capturing of the residue of microbial or higher eukaryotic cells and the improved halohydrin epoxidase activity can be recovered in filtrate. For example, a membrane with a pore size of about 0.1 to 0.5 μm may be used. Further, when using a filter aid, and a flocculant according to need, a membrane or filter paper with a pore size of 0.5 μm or more may also be used. Examples of filter aids include diatomaceous earth, cellulose powder and active carbon. Flocculants are as described above.

The supernatant obtained after removal of the residue is a cell extract soluble fraction, and this may be used as a crude enzyme solution containing the improved halohydrin epoxidase. Subsequently, according to need, common biochemical methods used for isolation/purification of proteins, such as ammonium sulfate precipitation, various chromatographies (e.g., gel filtration chromatography (with Sephadex column, etc.), ion exchange chromatography (with DEAE-Toyopearl, etc.), affinity chromatography, hydrophobic chromatography (with butyl Toyopearl, etc.), anion chromatography (with MonoQ column, etc.)) or SDS polyacrylamide gel electrophoresis may be suitably used solely or in combination, thereby isolating/purifying halohydrin epoxidase from the aforementioned culture.

When the transformant of the present invention is a genetic recombinant and there is a possible risk of secondary microbial contamination due to leakage of the transformant into environments or mixing of the transformant into products during the production process, inappropriate handling of the transformant after use or the like, according to need, inactivation of the transformant may be performed. As the inactivation method, any method may be employed as long as it does not reduce the improved halohydrin epoxidase activity or the activity recovery ratio and can inactivate the transformant. Examples thereof include thermal treatment, treatment of disintegrating cells and drug treatment. These methods can be used solely or in combination. For example, the transformant may be inactivated by treating it with a drug before or after the treatment of disintegrating cells. The drug to be used varies depending on the type of host of the transformant. Examples thereof include: cationic surfactants such as benzethonium chloride, cetylpyridinium chloride, methylstearoyl chloride and cetyltrimethylammonium bromide; and zwitterionic surfactants such as alkyldiaminoethylglycine hydrochloride. Further, alcohols such as ethanol, thiols such as 2-mercaptoethanol, amines such as ethylenediamine, amino acids such as cysteine, ornithine and citrulline, etc. may also be enumerated. Regarding the concentration of the drug, it is sufficient if the improved halohydrin epoxidase activity or the activity recovery ratio is not reduced and the transformant can be inactivated. For example, the drug may be used at a concentration of about 1/100 to 1/2, and preferably about 1/10 to 1/5, relative to the dry weight % concentration of the microorganism. The treatment temperature is 0 to 50° C., and preferably 0 to 40° C. The pH is about 5 to 9, and preferably about 6 to 8.

On the other hand, when the improved halohydrin epoxidase is produced outside the microbial or higher eukaryotic cells, the culture solution may be used as it is, or the microbial or higher eukaryotic cells are removed by means of centrifugation, filtration, etc. as described above. After that, the improved halohydrin epoxidase is collected from the aforementioned culture by means of extraction utilizing ammonium sulfate precipitation, etc. (if necessary). In addition, according to need, dialysis and various chromatographies (e.g., gel filtration, ion exchange chromatography, and affinity chromatography) are suitably used solely or in combination, thereby performing purification.

When the transformant is a plant cell or tissue, cells are disrupted by cell lysis treatment using enzymes such as cellulase and pectinase, ultrasonic fragmentation treatment, treatment of grinding down by friction or the like. After that, if required, common biochemical methods used for isolation/purification of proteins, such as ammonium sulfate precipitation, various chromatographies (e.g., gel filtration chromatography (with Sephadex column, etc.), ion exchange chromatography (with DEAE-Toyopearl, etc.), affinity chromatography, hydrophobic chromatography (with butyl Toyopearl, etc.), anion chromatography (with MonoQ column, etc.)) or SDS polyacrylamide gel electrophoresis may be suitably used solely or in combination, thereby isolating/purifying halohydrin epoxidase from the aforementioned culture. The isolated halohydrin epoxidase may be supported by a suitable carrier to be used as an immobilized enzyme, as in the above-described case of higher eukaryotic or microbial cells.

The culture and the improved halohydrin epoxidase thus obtained are within the scope of the present invention. The production yield of the obtained culture and the improved halohydrin epoxidase may calculated by measuring the halohydrin epoxidase activity described in (I) above per culture equipment, culture solution, wet weight or dry weight of cell (transformant), weight of protein in enzyme solution, or the like.

In the present invention, it is also possible to collect the improved halohydrin epoxidase from the above-described improved halohydrin epoxidase gene or a recombinant vector comprising the improved halohydrin epoxidase gene. That is, in the present invention, it is possible to produce the improved halohydrin epoxidase by employing a cell-free protein synthesis system without using living cells. The "cell-free protein synthesis system" is a system in which protein is synthesized in an artificial container such as a test tube using a cell extract. A cell-free transcription system, in which RNA is synthesized using DNA as a template, is also included in the cell-free protein synthesis system used in the present invention. In this case, an organism corresponding to the above-described host corresponds to an organism from which the cell extract described below is derived. In this regard, as the cell extract, a eukaryotic cell- or prokaryotic cell-derived cell extract (e.g., an extract from wheat germs or $E.$ $coli$) may be used. These cell extracts may be either concentrated or non-concentrated. Cell extracts may be obtained by means of ultrafiltration, dialysis, polyethylene glycol (PEG) precipitation or the like. Moreover, in the present invention, the cell-free protein synthesis may also be performed using a commercially available kit. Examples of such kits include reagent kits PROTEIOS™ (Toyobo) and TNT™ System (Promega) and synthesis apparatuses PG-Mate™ (Toyobo) and RTS (Roche Diagnostics).

The improved halohydrin epoxidase obtained by the cell-free protein synthesis as described above can be purified, for example, by appropriately selecting chromatography as described above.

(VI) Method for Producing Epihalohydrin and 4-halo-3-hydroxybutyronitrile

The improved halohydrin epoxidase produced as described above can be utilized in the substance production as an enzyme catalyst. That is, the improved halohydrin epoxidase can be used for the following reactions in (VI-1) to (VI-3).

(VI-1) Conversion of 1,3-dihalo-2-propanol into Epihalohydrin

This conversion reaction can be performed by bringing 1,3-dihalo-2-propanol into contact with the aforementioned improved halohydrin epoxidase and/or the culture obtained by culturing as described above.

The substrate, 1,3-dihalo-2-propanol is a compound represented by the aforementioned general formula (1). As the halogen atom, fluorine, chlorine, bromine and iodine are preferred, and chlorine and bromine are particularly preferred. Specific examples thereof include 1,3-difluoro-2-propanol, 1,3-dichloro-2-propanol, 1,3-dibromo-2-propanol, and 1,3-diiodo-2-propanol, and 1,3-dichloro-2-propanol and 1,3-dibromo-2-propanol are preferred.

The substrate concentration in the conversion reaction solution is preferably 0.01 to 15 (W/V) %. Within this range, it is preferred in terms of enzyme stability. The concentration is particularly preferably 0.01 to 10%. The substrate can be added to the reaction solution all at a time or portionwise. It is preferred that the substrate concentration is maintained by such split addition in terms of accumulability.

As a solvent for the reaction solution, water or a buffer solution having pH of about 4 to 10, which is optimum for enzyme activity, is preferred. Preferred examples of buffer solutions include buffer solutions constituted by a salt (e.g., phosphoric acid, boric acid, citric acid, glutaric acid, malic acid, malonic acid, o-phthalic acid, succinic acid and acetic acid), etc., Tris buffer solution, and Good's buffer solution.

The reaction temperature is preferably 5 to 50° C., and the reaction pH is preferably 4 to 10.

The reaction temperature is more preferably 10 to 40° C., and the reaction pH is more preferably 6 to 9. The reaction time is suitably selected based on the substrate concentration, the concentration of cells and other reaction conditions, but the conditions are preferably set so that the reaction is completed in 1 to 120 hours. In this reaction, by removing chlorine ion, which is produced as the reaction proceeds, from the reaction system, the optical purity can be further improved. This removal of chlorine ion is preferably performed by addition of silver nitrate, etc.

The epihalohydrin produced and accumulated in the reaction solution can be collected and purified using a publicly-known method. For example, extraction is performed using a solvent such as ethyl acetate, and the solvent is removed under reduced pressure, thereby obtaining a syrup of epihalohydrin. Further purification can be performed by distilling the syrup under reduced pressure.

(VI-2) Conversion of 1,3-dihalo-2-propanol into 4-halo-3-hydroxybutyronitrile This conversion reaction can be performed by bringing 1,3-dihalo-2-propanol into contact with the aforementioned improved halohydrin epoxidase and/or the culture obtained by culturing as described above.

The substrate, 1,3-dihalo-2-propanol is a compound represented by the aforementioned general formula (1), and preferably 1,3-dichloro-2-propanol, 1,3-dibromo-2-propanol, etc.

As a cyanogen compound, a compound which generates cyanogen ion (CN—) or hydrogen cyanide when added to a reaction solution of hydrogen cyanide, potassium cyanide, sodium cyanide, cyanic acid, acetone cyanhydrin or the like, or a solution thereof can be used. In terms of enzyme stability, the substrate concentration in the reaction solution is preferably 0.01 to 15 (W/V) %, and particularly preferably 0.01 to 10%.

The use amount of the cyanogen compound is preferably 1 to 3 volumes (mole) based on the substrate in terms of enzyme stability.

The reaction conditions may be the same as those in (VI-1) above.

The 4-halo-3-hydroxybutyronitrile produced and accumulated in the reaction solution can be collected and purified using a publicly-known method. For example, after cells are removed from the reaction solution using a method such as centrifugation, extraction is performed using a solvent such as ether acetate, and the solvent is removed under reduced pressure, thereby obtaining syrup of 4-halo-3-hydroxybutyronitrile. Further purification can be performed by distilling the syrup under reduced pressure.

(VI-3) Conversion of Epihalohydrin into 4-halo-3-hydroxybutyronitrile

This conversion reaction can be performed by bringing epihalohydrin into contact with the aforementioned improved halohydrin epoxidase and/or the culture obtained by culturing as described above.

The substrate, epihalohydrin is a compound represented by the aforementioned general formula (2). As the halogen atom, fluorine, chlorine, bromine and iodine are preferred, and chlorine and bromine are particularly preferred. Specific examples thereof include epifluorohydrin, epichlorohydrin, epibromohydrin and epiiodohydrin, and epichlorohydrin and epibromohydrin are particularly preferred.

As a cyanogen compound, a compound which generates cyanogen ion (CN—) or hydrogen cyanide when added to a reaction solution of hydrogen cyanide, potassium cyanide, sodium cyanide, cyanic acid, acetone cyanhydrin or the like, or a solution thereof can be used.

The reaction conditions and method of collection and purification may be the same as those in (VI-2) above.

EXAMPLES

Hereinafter, the present invention will be described in more detail based on working examples, but the present invention is not limited thereto.

Example 1

Obtaining Improved Halohydrin Epoxidase in which an Amino Acid Residue which is One Residue Closer to the C-Terminal End than the Start Amino Acid Residue is Substituted with Another Amino Acid and Evaluation Thereof (1) Preparation of Transformants Expressing Improved Halohydrin Epoxidase (Expression Vector pKK233-2)

Expression plasmids (expression vector pKK233-2) which express an improved halohydrin epoxidase in which an amino acid residue that is one-residue downstream of the amino acid residue encoded by the translation initiation codon (second amino acid residue) is substituted with lysine or asparagine in HheB ($2^{nd}$), which is a wild-type halohydrin epoxidase from *Corynebacterium* sp. strain N-1074, and transformants expressing the improved halohydrin epoxidases including the expression plasmids, were prepared as follows.

Firstly, the halohydrin epoxidase gene HheB ($2^{nd}$) was amplified with PCR. Compositions of PCR reaction solutions (each 50 μl in total) are as shown in the table below, and 3 lines were prepared (the three lines respectively have different sense primers).

TABLE a

|  | Line 1 | Line 2 | Line 3 |
|---|---|---|---|
| Pfuturbo DNA polymerase (2.5 U/μl) (Stratagene) | 1 μl | 1 μl | 1 μl |
| 10× Cloned Pfu DNA polymerase reaction buffer (Stratagene) | 5 μl | 5 μl | 5 μl |
| dNTP Mixture (2.5 mM for each) | 4 μl | 4 μl | 4 μl |
| Sense primer (100 μM) | DH-08 1 μl | DH-09 1 μl | DH-10 1 μl |
| Antisense primer DH-07 (100 μM) | 1 μl | 1 μl | 1 μl |
| Template plasmid pST111 (100 ng/μl) | 1 μl | 1 μl | 1 μl |
| Sterile distilled water | 37 μl | 37 μl | 37 μl |
| Total | 50 μl | 50 μl | 50 μl |

Sequences of the oligonucleotides used as the primers are as follows:

DH-08: GGCCATGGCTAACGGAAGACTGGCAGGC (SEQ ID NO: 57: the sequence consists of 28 nucleotides; the sequence has the restriction enzyme NcoI recognition site (CCATGG) and a region starting from the translation initiation codon in the halohydrin epoxidase gene HheB ($2^{nd}$); and the codon corresponding to the second amino acid is GCT and encodes alanine.)

DH-09: GATCATGAAAAACGGAAGACTGGCAGGCAAGCG (SEQ ID NO: 58: the sequence consists of 33 nucleotides; the sequence has the restriction enzyme BspHI recognition site (TCATGA) and a region starting from the translation initiation codon in the halohydrin epoxidase gene HheB ($2^{nd}$); and the codon corresponding to the second amino acid is AAA and encodes lysine.)

DH-10: GATCATGAACAACGGAAGACTGGCAGGCAAGCG (SEQ ID NO: 59: the sequence consists of 33 nucleotides; the sequence has the restriction enzyme BspHI recognition site (TCATGA) and a region starting from the translation initiation codon in the halohydrin epoxidase gene HheB ($2^{nd}$); and the codon corresponding to the second amino acid is AAC and encodes asparagine.)

DH-07: CGCCTGCAGGCTACAACGACGACGAGCGCCTG (SEQ ID NO: 60: the sequence consists of 32 nucleotides; and the sequence has the recognition site of the restriction enzymes Sse8387I and PstI (CCTGCAGG) and a region downstream of the termination codon in the halohydrin epoxidase gene HheB ($2^{nd}$).)

Further, pST111, which was used as a template, is described in Japanese Publication for Opposition No. 5-317066. The *E. coli* transformant JM109/pST111 obtained using a recombinant vector including pST111 was deposited to the International Patent Organism Depositary, National Institute of Advanced Industrial Science and Technology on Mar. 1, 1991 (Accession No. FERM BP-10922).

The prepared PCR reaction solutions (50 μl for each) were respectively subjected to the following thermal cycling treatment.

TABLE b

| Temperature | Time | Cycle number |
|---|---|---|
| 95° C. | 2 minutes | — |
| 94° C. | 30 seconds | 30 |
| 50° C. | 30 seconds |  |
| 72° C. | 2 minutes |  |
| 72° C. | 10 minutes | — |

The PCR reaction solutions of the three lines after the thermal cycling treatment were respectively purified by GFX PCR DNA band and GelBand Purification kit (GE Healthcare Bio-Sciences). After that, the PCR amplification product of the line 1 was subjected to double digestion using restriction enzymes NcoI and PstI, and the PCR amplification products of the lines 2 and 3 were respectively subjected to double digestion using restriction enzymes BspHI and PstI. The respective digested products were separated by means of agarose gel electrophoresis, and after that, a band including the full-length halohydrin epoxidase gene (about 0.8 kb) was purified using QIAquick Gel Extraction Kit (QIAGEN). Meanwhile, an expression vector pKK233-2 (+Sse), which is a derivative of pKK233-2 (Centraalbureau voor Schimmelcultures (CBS), Netherlands; http://www.cbs.knaw.nl/), and which can be prepared using the method described in International Publication WO 2006/41226 pamphlet, was digested with restriction enzymes NcoI and PstI, and after that, purification was performed using phenol extraction/chloroform extraction/ethanol precipitation (Molecular Cloning, A Laboratory Manual, 2nd ed. (Cold Spring Harbor Laboratory Press (1989))). The purified product was mixed with each of the three types of PCR amplification products including the above-described full-length halohydrin epoxidase gene, and after that, Solution I (DNA Ligation Kit ver. 2; Takara Bio Inc.) was added to each of the mixtures to prepare ligation mixtures. Each of the mixtures was incubated at 16° C. for 12 hours, thereby combining each of the PCR amplification products with the expression vector pKK233-2 (+Sse).

200 µl of E. coli strain JM109 competent cells prepared in advance (E. coli strain JM109 was inoculated into 1 ml of LB medium (1% Bacto tryptone, 0.5% Bacto yeast extract, 0.5% NaCl) and precultured at 37° C. for 5 hours aerobically; after that, the resultant preculture solution (0.4 ml) was added to 40 ml of SOB medium (2% Bacto tryptone, 0.5% Bacto yeast extract, 10 mM NaCl, 2.5 mM KCl, 1 mM MgSO$_4$, 1 mM MgCl2) and cultured at 18° C. for 20 hours; the obtained culture was harvested by centrifugation (3,700×g, 10 minutes, 4° C.), and after that, 13 ml of cold TF solution (20 mM PIPES-KOH (pH 6.0), 200 mM KCl, 10 mM CaCl2, 40 mM MnCl2) was added thereto; the mixture was left at 0° C. for 10 minutes, and subsequently the mixture was recentrifuged (3,700×g, 10 minutes, 4° C.) to remove the supernatant; the obtained cells of E. coli were suspended in 3.2 ml of cold TF solution; 0.22 ml of dimethylsulfoxide was added thereto, and the mixture was left at 0° C. for 10 minutes; and after that, the resultant mixture was preserved at −80° C. using liquid nitrogen) was added to 10 µl of the ligation product, and the mixture was left at 0° C. for 30 minutes. Subsequently, the competent cells were subjected to heat shock at 42° C. for 30 seconds and cooled at 0° C. for 2 minutes. After that, 1 ml of SOC medium (20 mM glucose, 2% Bacto tryptone, 0.5% Bacto yeast extract, 10 mM NaCl, 2.5 mM KCl, 1 mM MgSO4, 1 mM MgCl2) was added thereto, and the resultant mixture was subjected to shaking culture at 37° C. for 1 hour. The resultant culture solution in 200 µl aliquots was applied to LB Amp agar medium (LB medium containing 100 mg/L ampicillin and 1.5% agar) and cultured overnight at 37° C. A plurality of transformant colonies grown on the agar medium were cultured overnight in 1.5 ml of LB Amp medium (LB medium containing 100 mg/L ampicillin) at 37° C. After each of the resultant culture solutions was harvested, recombinant plasmids were collected using Flexi Prep (GE Healthcare Bio-Sciences). The nucleotide sequences of the PCR amplification products cloned in the three types of plasmids were analyzed using a capillary DNA sequencer CEQ 2000 (BECKMAN COULTER) according to the attached manual, and it was confirmed that no error mutation occurred in the PCR reaction. The plasmid in which a DNA fragment from the PCR amplification product of the line 1 was cloned was designated as pSTK001. The plasmid in which a DNA fragment from the PCR amplification product of the line 2 was cloned was designated as pSTK002. The plasmid in which a DNA fragment from the PCR amplification product of the line 3 was cloned was designated as pSTK003. Further, the transformants of E. coli strain JM109 including the plasmids were designated as JM109/pSTK001, JM109/pSTK002 and JM109/pSTK003, respectively.

Characteristics of each of the above-described plasmids are as follows:

pSTK001: a wild-type halohydrin epoxidase gene encoding the wild-type halohydrin epoxidase HheB ($2^{nd}$) in which the second amino acid residue is an alanine residue is cloned into the expression vector pKK233-2.

pSTK002: an improved halohydrin epoxidase gene encoding the improved halohydrin epoxidase HheB ($2^{nd}$) in which the second amino acid residue (alanine residue) is substituted with lysine is cloned into the expression vector pKK233-2.

pSTK003: an improved halohydrin epoxidase gene encoding the improved halohydrin epoxidase HheB ($2^{nd}$) in which the second amino acid residue (alanine residue) is substituted with asparagine is cloned into the expression vector pKK233-2.

(2) Preparation of Transformants Expressing Improved Halohydrin Epoxidase (Expression Vector pTrc99A)

Expression plasmids (expression vector pTrc99A) which express an improved halohydrin epoxidase in which an amino acid residue that is one residue closer to the C-terminal end than the start amino acid residue (second amino acid residue) is substituted with lysine and asparagine, respectively, in HheB ($2^{nd}$), which is a wild-type halohydrin epoxidase from Corynebacterium sp. strain N-1074, and transformants expressing the improved halohydrin epoxidases including the expression plasmids, were prepared. The preparation was carried out in a manner similar to that in Example 1 (1) except that pTrc99A was used instead of the expression vector pKK233-2 that was used in Example 1 (1). The plasmid in which a DNA fragment from the PCR amplification product of the line 1 was cloned was designated as pSTT001. The plasmid in which a DNA fragment from the PCR amplification product of the line 2 was cloned was designated as pSTT002. The plasmid in which a DNA fragment from the PCR amplification product of the line 3 was cloned was designated as pSTT003. Further, the transformants of E. coli strain JM109 including the plasmids were designated as JM109/pSTT001, JM109/pSTT002 and JM109/pSTT003, respectively.

Characteristics of each of the above-described plasmids are as follows:

pSTT001: a wild-type halohydrin epoxidase gene encoding the wild-type halohydrin epoxidase HheB ($2^{nd}$) in which the second amino acid residue is an alanine residue is cloned into the expression vector pTrc99A.

pSTT002: an improved halohydrin epoxidase gene encoding the improved halohydrin epoxidase HheB ($2^{nd}$) in which the second amino acid residue (alanine residue) is substituted with lysine is cloned into the expression vector pTrc99A.

pSTT003: an improved halohydrin epoxidase gene encoding the improved halohydrin epoxidase HheB ($2^{nd}$) in which the second amino acid residue (alanine residue) is substituted with asparagine is cloned into the expression vector pTrc99A.

(3) Evaluation of Transformants Expressing Improved Halohydrin Epoxidase

The six transformant strains prepared in Example 1 (1) and (2) (JM109/pSTK001, JM109/pSTK002, JM109/pSTK003, JM109/pSTT001, JM109/pSTT002 and JM109/pSTT003) and the strain JM109/pST111 described in Japanese Publication for Opposition No. 5-317066 (7 strains in total) were evaluated using IPTG (isopropyl-1-thio-D-β-D-galactoside) as follows. 1 ml of LBAmp medium was poured into each of Wassermann test tubes, and colonies of the 6 strains selected in the secondary evaluation and JM109/pST111 were inoculated into the test tubes, respectively. They were cultured at 37° C. at 210 rpm for about 8 hours, and subsequently 100 µl of each of the obtained culture solutions was inoculated into LBAmp medium containing 1 mM IPTG as the final concentration (100 ml in a 500 ml conical flask) and cultured at 37° C. at 210 rpm for 24 hours. Respective cells were collected from the obtained culture solutions by means of centrifugation (3,700×g, 10 minutes, 4° C.), and after washed with 20 mM Tris-sulfuric acid buffer solution (pH 8.0), the cells were suspended in the same buffer solution so that the concentration of the cells became 12.5 gDC/L. 1 ml of the obtained suspension containing the cells was disintegrated for 3 minutes using a sonicator VP-15S (Taitec, Japan) while ice-cooling under the following conditions: output control 4, DUTY CYCLE 40%, PULS, TIMER=B mode 10s. The disintegrated suspension containing the cells was subjected to centrifugation (23,000×g, 5 minutes, 4° C.); and the supernatant was collected as a crude enzyme solution. Each of the obtained crude enzyme solutions was diluted with 20 mM Tris-sulfuric acid buffer solution (pH 8.0) so that the concentration of the cells before disintegrated (at the time when it was still the suspension containing the cells) became 6.25 gDC/L. Each of the diluted crude enzyme solutions from the respective transformants was mixed with an equal amount of polyacrylamide gel electrophoresis sample buffer (0.1 M Tris-HCl (pH 6.8), 4% w/v SDS. 12% v/v β-mercaptoethanol, 20% v/v glycerol, a slight amount of bromophenol blue), and each of the mixture was boiled for 5 minutes to be subjected to modification treatment. 10% polyacrylamide gel was prepared, and the modified samples were applied to respective lanes (5 μl per lane) and subjected to electrophoresis analysis (FIG. 1). Each halohydrin epoxidase was observed as a band of slightly over 30 kDa (the arrow mark in FIG. 1). It was confirmed that the expression level of each of the crude enzyme solutions derived from JM109/pSTK001 and JM109/pSTT001, both of which express the wild-type halohydrin epoxidase HheB ($2^{nd}$), was increased compared to the crude enzyme solution derived from JM109/pST111 expressing the wild-type halohydrin epoxidase HheB ($1^{st}$) (it is thought that this is attributed to the difference in expression vector). Meanwhile, it was confirmed that, when compared to the crude enzyme solutions derived from JM109/pSTK001 and JM109/pSTT001, the expression level of each of the crude enzyme solutions derived from JM109/pSTK003 and JM109/pSTT003, both of which express the improved halohydrin epoxidase HheB ($2^{nd}$) in which the second amino acid residue is substituted with asparagine, was more increased, and the expression level of each of the crude enzyme solutions derived from JM109/pSTK002 and JM109/pSTT002, both of which express the improved halohydrin epoxidase HheB ($2^{nd}$) in which the second amino acid residue is substituted with lysine, was much further increased.

Subsequently, using the above-described crude enzyme solutions, halohydrin epoxidase activities (dechlorination activity) were measured according to the method described below. 100 ml of reaction solution for measurement of activity (50 mM DCP, 50 mM Tris-sulfuric acid (pH8)) was prepared, and the temperature was adjusted to 20° C. To the reaction solution, each of the diluted crude enzyme solutions derived from the respective transformants was added, thereby initiating a reaction. In order to prevent pH decrease due to free chloride ion caused by the halohydrin epoxidase activity, an automatic pH controller and 0.01 N sodium hydroxide solution were used to continuously adjust pH to 8. The production amount of chloride ion was calculated from the amount of 0.01 N sodium hydroxide solution used to maintain pH 8 during the reaction time (10 minutes), and then the halohydrin epoxidase activity (dechlorination activity) (U) was calculated. 1 U is defined as corresponding to the enzyme level by which 1 μmol of chloride ion is detached from DCP per minute under the above-described conditions, and the activity of each of the crude enzyme solutions used in the activity measurement was calculated. Further, by dividing the activity by the fluid volume of each of the crude enzyme solutions used in the activity measurement, the liquid activity of each of the crude enzyme solutions was calculated. Further, assuming that the cells were completely disintegrated by the above-described ultrasonic treatment, by dividing the liquid activity by the concentration of the cells before disintegrated (at the time when it was still the suspension containing the cells), the cell specific activity was calculated. Results of the cell specific activity of each of the transformants are shown in Table 1. It was confirmed that, when compared to JM109/pSTK001 and JM109/pSTT001 which express the wild-type halohydrin epoxidase HheB ($2^{nd}$), the cell specific activities of JM109/pSTK003 and JM109/pSTT003, which express the improved halohydrin epoxidase HheB ($2^{nd}$) in which the second amino acid residue is substituted with asparagine, increased about 12 times and about 5 times, respectively, and further, the cell specific activities of JM109/pSTK002 and JM109/pSTT002, which express the improved halohydrin epoxidase HheB ($2^{nd}$) in which the second amino acid residue is substituted with lysine, increased about 25 times and about 17 times, respectively. That is, regarding the transformant expressing the improved halohydrin epoxidase in which the amino acid residue which is one residue closer to the C-terminal end than the start amino acid residue (the second amino acid residue in the amino acid sequence represented by SEQ ID NO: 2) is substituted with another amino acid, it was confirmed that the halohydrin epoxidase activity per transformant was higher than that of the wild-type halohydrin epoxidase.

TABLE 1

| Transformant | Cell specific activity [U/mgDC] | Relative value |
|---|---|---|
| JM109/pSTK001 | 0.14 | 1 |
| JM109/pSTK002 | 3.50 | 25.0 |
| JM109/pSTK003 | 1.64 | 11.7 |
| JM109/pSTT001 | 0.24 | 1 |
| JM109/pSTT002 | 4.14 | 17.3 |
| JM109/pSTT003 | 1.26 | 5.3 |

*In the case of JM109/pSTK002 and JM109/pSTK003, the cell specific activity of JM109/pSTK001 is regarded as 1, and in the case of JM109/pSTT002 and JM109/pSTT003, the cell specific activity of JM109/pSTT001 is regarded as 1, and relative values thereof were calculated, respectively.

Example 2

Screening of Improved Halohydrin Epoxidase Utilizing Random Mutation (1) Preparation of Halohydrin Epoxidase Mutant Library In order to obtain more useful improved halohydrin epoxidases, a halohydrin epoxidase gene mutant library in which random mutation was introduced by means of error prone PCR was prepared, and improved halohydrin epoxidases and genes thereof from the library were screened.

Using pSTT002 prepared in Example 1 (2) as a template, a halohydrin epoxidase gene mutant library was prepared utilizing error prone PCR as described below. 100 μl of PCR reaction solution having the composition described in the below table was prepared.

TABLE c

| | |
|---|---|
| Taq DNA polymerase(New England Biolabs) | 1 μl |
| 10× buffer(New England Biolabs) | 10 μl |
| dNTP Mixture (2.5 mM for each) | 8 μl |
| $MgCl_2$ (25 mM) | 4 μl |
| Sense primer DH-09 (50 μM) | 2 μl |
| Antisense primer Trc-03 (50 μM) | 2 μl |
| Template plasmid pSTT002 (100 ng/μl) | 4 μl |
| Sterile distilled water | 69 μl |
| Total | 100 μl |

The sequence of Trc-03 used as the primer is as follows:
Trc-03: GGCTGAAAATCTTCTCTCATCCGCC (SEQ ID NO: 61: the sequence consists of 25 nucleotides and corresponds to the downstream region of the multicloning site of pTrc99A.)

The prepared PCR reaction solution (100 μl) was dividedly poured into 10 tubes for PCR reaction (10 μl for each), and thereafter subjected to the following thermal cycling treatment.

TABLE d

| Temperature | Time | Cycle number |
|---|---|---|
| 95° C. | 5 minutes | — |
| ↓ | | |
| 95° C. | 1 minute | 30 |
| 55° C. | 1 minute | |
| 72° C. | 2 minutes | |
| ↓ | | |
| 72° C. | 10 minutes | — |

The PCR reaction solutions in 10 tubes after the thermal cycling treatment were mixed together, and in a manner similar to that in Example 1 (2), purification and restriction enzyme digestion (double digestion using NcoI and PstI) of the PCR reaction solution and purification from gel; restriction enzyme digestion (double digestion using NcoI and PstI) and purification of the expression vector pTrc99A; ligation reaction; and transformation were carried out. The colonies which appeared on the plate were used as the halohydrin epoxidase gene mutant library.

(2) Screening of Improved Halohydrin Epoxidase (Primary Evaluation)

Using the halohydrin epoxidase gene mutant library prepared in Example 2 (1), the improved halohydrin epoxidase was subjected to screening (primary evaluation) as follows: LBAmp medium containing 1 mM IPTG as the final concentration was dividedly poured into a 96-well plate (Deep Well) (500 μl per well), and the colonies of the halohydrin epoxidase gene mutant library was inoculated into each well. However, into 1 or 2 wells among the 96 wells, the colony of JM109/pSTT002 to be used as a control for evaluation was inoculated. After cultured at 37° C. at 800 rpm for about 16 hours, 20 μl of the culture solution obtained was dividedly poured into a flat-type 96-well plate. Using a centrifuge (Sakuma Seisakusho; 50A-IVD) and a rotor (Sakuma Seisakusho; HM-2HLS), the flat-type 96-well plate was subjected to centrifugation (3000 rpm, 5 minutes, 4° C.). After the culture supernatant was removed, 40 μl of reaction solution 1 for evaluation (400 mM DCP, 800 mM (R)-CHBN, 0.025% bromocresol purple (BCP), 50 mM Tris-sulfuric acid (pH8)) was added to each well. After suspension, it was allowed to stand at room temperature, and change in color of the reaction solution was observed over time (the color of BCP changes from purple to yellow due to decrease in pH accompanied by the production of chloride ion by the halohydrin epoxidase activity). Strains, regarding which change in color was observed significantly faster than the case of the control, JM109/pSTT002, were selected. Colonies of about 20,000 strains were subjected to the primary evaluation, and 77 strains were selected.

(3) Screening of Improved Halohydrin Epoxidase (Secondary Evaluation)

The 77 strains selected in the primary evaluation in Example 2 (2) were subjected to the secondary evaluation as follows. In a manner similar to that in Example 2 (2), the 77 strains selected in the primary evaluation were cultured in a 96-well plate (Deep Well), and after that, samples ((20 μl, 15 μl, 10 μl, 5 μl)×2) of each of the obtained culture solutions were dividedly poured into a flat-type 96-well plate. Using a centrifuge (Sakuma Seisakusho; 50A-IVD) and a rotor (Sakuma Seisakusho; HM-2HLS), the flat-type 96-well plate was subjected to centrifugation (3000 rpm, 5 minutes, 4° C.). After the culture supernatant was removed, for precipitate (cells) of each of the culture solutions, 40 μl of the reaction solution 1 for evaluation described in Example 2 (2) and 40 μl of reaction solution 2 for evaluation (400 mM DCP, 0.025% bromocresol purple (BCP), 50 mM Tris-sulfuric acid (pH8)) were added to each well. After suspension, it was allowed to stand at room temperature, and change in color of the reaction solution was observed over time. Strains, regarding which change in color was observed significantly faster than the case of the control, JM109/pSTT002 when adding the reaction solution 1 for evaluation, and regarding which the difference between the rate of change in color when adding the reaction solution 1 for evaluation and the rate of change in color when adding the reaction solution 2 for evaluation was small, were selected. The 77 strains selected in the primary evaluation were subjected to the secondary evaluation, and 20 strains were selected.

(4) Confirmation of Mutation of Halohydrin Epoxidase Gene of Strains Selected in the Secondary Evaluation Regarding the 20 strains selected in the secondary evaluation in Example 2 (3), mutation of halohydrin epoxidase gene possessed by each of the strains was analyzed. Plasmids were collected from the respective culture solutions obtained in Example 2 (3) using Flexi Prep (GE Healthcare Bio-Sciences). Then, the nucleotide sequence of the halohydrin epoxidase gene in each of the plasmids was analyzed using a capillary DNA sequencer CEQ 2000 (BECKMAN COULTER) according to the attached manual. Results are shown in Table 2.

TABLE 2

| Transformant | Amino acid substitution mutation (*) | Codon mutation | Name of transformant |
|---|---|---|---|
| #1002 | T133A | ACG→GCG | JM109/pSTT002-T133A |
| #1005 | T133A | ACG→GCG | JM109/pSTT002-T133A |
| #1007 | F136S | TTC→TCC | JM109/pSTT002-F136S |
| #1009 | F136S | TTC→TCC | JM109/pSTT002-F136S |
| #1014 | F136S | TTC→TCC | JM109/pSTT002-F136S |
| #1018 | D199H | GAC→CAC | JM109/pSTT002-D199H |
| #1019 | F136S | TTC→TCC | JM109/pSTT002-F136S |
| #1020 | V75A | GTG→GCG | JM109/pSTT002-V75A |
| #1023 | F136S | TTC→TCC | JM109/pSTT002-F136S |
| #1024 | F136S | TTC→TCC | JM109/pSTT002-F136S |
| #1029 | V25I | GTC→ATC | JM109/pSTT002-V25I |

TABLE 2-continued

| Transformant | Amino acid substitution mutation (*) | Codon mutation | Name of transformant |
|---|---|---|---|
| #1034 | F136S | TTC→TCC | JM109/pSTT002-F136S |
| #1037 | F136S | TTC→TCC | JM109/pSTT002-F136S |
| #1038 | F136S | TTC→TCC | JM109/pSTT002-F136S |
| #1050 | (R107R) | CGT→CGC | JM109/pSTT002-R107R |
| #1055 | V75A | GTG→GCG | JM109/pSTT002-V75A |
| #1057 | H57R, Y87F | CAC→CGC, TAC→TTC | JM109/pSTT002-H57R + Y87F |
| #1066 | F136S | TTC→TCC | JM109/pSTT002-F136S |
| #1068 | F136S | TTC→TCC | JM109/pSTT002-F136S |
| #1072 | F136S | TTC→TCC | JM109/pSTT002-F136S |

(*) In the halohydrin epoxidase in each of the strains, the second amino acid residue is substituted with lysine. The position of amino acid mutation indicates the position in Hheb ($2^{nd}$) (SEQ ID NO: 2).

Regarding the 20 strains analyzed, it was confirmed that: 12 strains (#1007, #1009, #1014, #1019, #1023, #1024, #1034, #1037, #1038, #1066, #1068, #1072) expressed a halohydrin epoxidase having an amino acid substitution mutation F136S; 2 strains (#1002, #1005) expressed a halohydrin epoxidase having an amino acid substitution mutation T133A; 2 strains (#1020, #1055) expressed a halohydrin epoxidase having an amino acid substitution mutation V75A; 1 strain (#1018) expressed a halohydrin epoxidase having an amino acid substitution mutation D199H; 1 strain (#1029) expressed a halohydrin epoxidase having an amino acid substitution mutation V25I; 1 strain (#1057) expressed a halohydrin epoxidase having amino acid substitutions mutations H57R and Y87F. The respective transformants, halohydrin epoxidases expressed thereby, and halohydrin epoxidase genes encoding the same were named as shown in Table 2.

(5) Screening of Improved Halohydrin Epoxidase (Tertiary Evaluation)

6 strains (JM109/pSTT002-V25I, JM109/pSTT002-H57R+Y87F, JM109/pSTT002-V75A, JM109/pSTT002-T133A, JM109/pSTT002-F136S and JM109/pSTT002-D199H), which were selected in Example 2 (3), and regarding which the halohydrin epoxidase gene mutation was confirmed in Example 2 (4), and a control strain JM109/pSTT002 (7 strains in total) were subjected to the tertiary evaluation as follows. 1 ml of LBAmp medium was poured into each of Wassermann test tubes, and colonies of the 6 strains selected in the secondary evaluation and JM109/pSTT002 were inoculated into the test tubes, respectively. They were cultured at 37° C. at 210 rpm for about 8 hours, and subsequently 100 μl of each of the obtained culture solutions was inoculated into LBAmp medium containing 1 mM IPTG as the final concentration (100 ml in a 500 ml conical flask) and cultured at 37° C. at 210 rpm for 16 hours. Each cell was collected from 100 ml of each of the obtained culture solution by means of centrifugation (3,700×g, 10 minutes, 4° C.), and after washed with 20 mM Tris-sulfuric acid buffer solution (pH 8.0), the cells were suspended in the same buffer solution so that the concentration of the cells became 12.5 gDC/L. Using the obtained suspension containing the cells, and employing the same method as described in Example 1 (3) except that the DCP concentration of the reaction solution was 400 mM and the same method as described in Example 1 (3) except that the DCP concentration of the reaction solution was 400 mM and that (R)-CHBN was added to the reaction solution to the final concentration of 800 mM, the halohydrin epoxidase activity (dechlorination activity) in the presence/absence of (R)-CHBN was measured. 1 U is defined as corresponding to the enzyme level by which 1 μmol of chloride ion is detached from DCP per minute under the above-described conditions, and the activity of each of the suspensions containing cells used in the activity measurement was calculated. Further, the liquid activity of each of the suspensions containing cells was calculated by dividing the activity by the fluid volume of each of the suspensions containing cells used in the activity measurement. Furthermore, the cell specific activity of each of the strains was calculated by dividing the liquid activity by the concentration of cells. Results are shown in Table 3.

TABLE 3

| Transformant | Cell specific activity in the absence of (R)-CHBN [U/mgDC] | Cell specific activity in the presence of (R)-CHBN [U/mgDC] |
|---|---|---|
| JM109/pSTT002-V25I | 17.4 | 1.40 |
| JM109/pSTT002-H57R + Y87F | 29.2 | 2.37 |
| JM109/pSTT002-V75A | 31.3 | 1.59 |
| JM109/pSTT002-T133A | 20.4 | 2.15 |
| JM109/pSTT002-F136S | 32.0 | 3.19 |
| JM109/pSTT002-D199H | 31.8 | 3.98 |
| JM109/pSTT002 | 21.2 | 1.74 |

Regarding JM109/pSTT002-H57R+Y87F, JM109/pSTT002-V75A, JM109/pSTT002-F136S and JM109/pSTT002-D199H, it was confirmed that the cell specific activity in the absence of (R)-CHBN was higher than the cell specific activity of JM109/pSTT002. Regarding JM109/pSTT002-H57R+Y87F, JM109/pSTT002-T133A, JM109/pSTT002-F136S and JM109/pSTT002-D199H, it was confirmed that the cell specific activity in the presence of (R)-CHBN was higher than the cell specific activity of JM109/pSTT002. That is, it was confirmed that halohydrin epoxidases expressed by these transformants were improved halohydrin epoxidases which achieve improvement of the halohydrin epoxidase activity per transformant in the absence or presence of (R)-CHBN.

Example 3

Screening of Improved Halohydrin Epoxidase by Means of Site-Specific Random Mutation (1) Preparation of Site-Specific Random Mutant Library Among the improved halohydrin epoxidases found in Example 2 (5), as positions of amino acid mutation which achieve improvement of the halohydrin epoxidase activity per transformant, the threonine residue at position-133 (T133), the phenylalanine residue at position-136 (F136) and the aspartic acid residue at position-199 (D199) in the halohydrin epoxidase Hheb ($2^{nd}$) (SEQ ID NO: 2) were found. The amino acids at these positions were mutated in a random manner, thereby trying to obtain more useful improved halohydrin epoxidases.

As random primers which can mutate T133, F136 and D199 to 20 essential amino acids, the following products were prepared:

MDH-14: CGCTGGCCTACAGCNNNGCGCGTTTCGCT (SEQ ID NO: 62; a sense primer consisting of 29 nucleotides, in which a codon encoding the amino acid at position-141 in the halohydrin epoxidase HheB ($1^{st}$) (SEQ ID NO: 1) or the amino acid at position-133 in the halohydrin epoxidase HheB ($2^{nd}$) (SEQ ID NO: 2) is a random base (NNN; N is any of adenine, thymine, guanine and cytosine));

MDH-15: AGCGAAACGCGCNNNGCTGTAGGC-CAGCG (SEQ ID NO: 63; an antisense primer consisting of 29 nucleotides, which has a complementary sequence of MDH-14);

MDH-16: CAGCACGGCGCGTNNNGCT-CAGCGCGGGT (SEQ ID NO: 64; a sense primer consisting of 29 nucleotides, in which a codon encoding the amino acid at position-144 in the halohydrin epoxidase HheB ($1^{st}$) (SEQ ID NO: 1) or the amino acid at position-136 in the halohydrin epoxidase HheB ($2^{nd}$) (SEQ ID NO: 2) is a random base (NNN; N is any of adenine, thymine, guanine and cytosine));

MDH-17: ACCCGCGCTGAGCNNNACGCGCCGTGCTG (SEQ ID NO: 65; an antisense primer consisting of 29 nucleotides, which has a complementary sequence of MDH-16);

MDH-18: CGACTGCCCGAGAGNNNGCGCT-GCTCGCG (SEQ ID NO: 66; a sense primer consisting of 29 nucleotides, in which a codon encoding the amino acid at position-207 in the halohydrin epoxidase HheB ($1^{st}$) (SEQ ID NO: 1) or the amino acid at position-199 in the halohydrin epoxidase HheB ($2^{nd}$) (SEQ ID NO: 2) is a random base (NNN; N is any of adenine, thymine, guanine and cytosine)); and MDH-19: CGCGAG-CAGCGCNNNCTCTCGGGCAGTCG (SEQ ID NO: 67; an antisense primer consisting of 29 nucleotides, which has a complementary sequence of MDH-18).

Using the above-described primers and the template pSTT002, site-specific mutation introduction was performed by means of QuickChange Site-Directed Mutagenesis Kit (STRATAGENE). The composition of each reaction solution (50 μl in total) is as described in the below table (the purpose of line 1, line 2 and line 3 was to obtain a T133 random mutant, a F136 random mutant and a D199 random mutant, respectively).

TABLE e

|  | Line 1 | Line 2 | Line 3 |
|---|---|---|---|
| Pfuturbo DNA polymerase (2.5 U/μl) (Stratagene) | 1 μl | 1 μl | 1 μl |
| 10× Cloned Pfu DNA polymerase reaction buffer (Stratagene) | 5 μl | 5 μl | 5 μl |
| dNTP Mixture (2.5 mM for each) | 1.25 μl | 1.25 μl | 1.25 μl |
| Sense primer (10 μM) | 1.25 μl | 1.25 μl | 1.25 μl |
| Antisense primer (10 μM) | 1.25 μl | 1.25 μl | 1.25 μl |
| Template plasmid pSTT002 (10 ng/μl) | 2 μl | 2 μl | 2 μl |
| Sterile distilled water | 39.5 μl | 39.5 μl | 39.5 μl |
| Total | 50 μl | 50 μl | 50 μl |

Combinations of primers used for the respective lines were as follows:

Line 1: sense primer MDH-14, antisense primer MDH-15
Line 2: sense primer MDH-16, antisense primer MDH-17
Line 3: sense primer MDH-17, antisense primer MDH-18

Each of the reaction solutions having the above-described composition was subjected to the thermal cycling treatment as described in the table below.

TABLE f

| Temperature | Time | Cycle number |
|---|---|---|
| 95° C. | 1 minute | — |
| ↓ | | |
| 95° C. | 50 seconds | 30 |
| 60° C. | 50 seconds | |
| 68° C. | 9 minutes | |
| ↓ | | |
| 68° C. | 7 minutes | — |

According to the attached manual, to each of the reaction solutions after subjected to the thermal cycling treatment, 1 μl of DpnI was added, and incubated at 37° C. for 1 hour. Using the DpnI treatment solution, transformation was performed in a manner similar to that in Example 2 (1). The colonies which appeared on the plate was used as the site-specific (T133, F136, D199) mutant library of halohydrin epoxidase gene.

(2) Screening of Improved Halohydrin Epoxidases from Site-Specific Random Mutants More useful improved halohydrin epoxidases were screened from the site-specific (T133, F136, D199) mutant library of halohydrin epoxidase gene prepared in Example 3 (1). LBAmp medium containing 1 mM IPTG as the final concentration was dividedly poured into a 96-well plate (Deep Well) (500 μl per well), and the colonies of the site-specific (T133, F136, D199) mutant library of halohydrin epoxidase gene prepared in Example 3 (1) (200 colonies for each line) were inoculated into each well. As controls for evaluation, JM109/pSTT002-T133A, JM109/pSTT002-F136S, JM109/pSTT002-D199H and JM109/pSTT002 were also inoculated. After cultured at 37° C. at 800 rpm for about 16 hours, 20 μl of the culture solution obtained was dividedly poured into a flat-type 96-well plate. Using a centrifuge (Sakuma Seisakusho; 50A-IVD) and a rotor (Sakuma Seisakusho; HM-2HLS), the flat-type 96-well plate was subjected to centrifugation (3000 rpm, 5 minutes, 4° C.). After the culture supernatant was removed, 40 μl of the reaction solution 1 for evaluation described in Example 2 (2) and 40 μl of reaction solution 3 for evaluation (200 mM (S)-CHBN, 0.025% bromocresol purple (BCP), and 50 mM Tris-sulfuric acid (pH 8)) were added to each well. After suspension, it was allowed to stand at room temperature, and change in color of the reaction solution was observed over time. Strains, regarding which change in color was observed significantly faster than the case of the control, JM109/pSTT002 when adding the reaction solution 1 for evaluation, and regarding which change in color was observed significantly faster than the case of the control, JM109/pSTT002 when adding the reaction solution 3 for evaluation, and regarding which the ratio between the rate of change in color when adding the reaction solution 1 for evaluation and the rate of change in color when adding the reaction solution 3 for evaluation was different from the ratio in the case of the control, JM109/pSTT002, were selected. 200 colonies of each of the lines were subjected to the evaluation. 7 strains from line 1 (T133 random mutant library), 7 strains from line 2 (F136 random mutant library) and 19 strains from line 3 (D199 random mutant library) were selected.

(3) Confirmation of Halohydrin Epoxidase Gene Mutation in Strains Selected from Site-Specific Random Mutant Library Regarding the 7 strains from line 1 (T133 random mutant library), the 7 strains from line 2 (F136 random mutant library) and the 19 strains from line 3 (D199 random mutant library) which were selected in Example 3 (2) (33 strain total), mutation of the halohydrin epoxidase gene possessed by each of the strains was analyzed. Plasmids were collected from the respective culture solutions of the strains obtained in Example 3 (2) using Flexi Prep (GE Healthcare Bio-Sciences). Then, using a capillary DNA sequencer CEQ 2000 (BECKMAN COULTER), the nucleotide sequence of the halohydrin epoxidase gene in each of the plasmids was analyzed according to the attached manual. Results are shown in Table 4.

solutions were prepared from the transformants expressing respective improved halohydrin epoxidases. The 15 transformant strains expressing the improved halohydrin epoxidase (JM109/pSTT002-T133A, JM109/pSTT002-T136C, JM109/pSTT002-T133S, JM109/pSTT002-F136A, JM109/pSTT002-F136S, JM109/pSTT002-F136W, JM109/pSTT002-D199Q, JM109/pSTT002-D199E, JM109/pSTT002-D199H, JM109/pSTT002-D199S, JM109/pSTT002-D199T, JM109/pSTT002-D199M, JM109/pSTT002-D199L, JM109/pSTT002-D199I, and JM109/pSTT002-D199Y) and the control JM109/pSTT002 (16 strains in total) were subjected to the tertiary evaluation as follows: 1 ml of LBAmp medium was poured into each of Wassermann test tubes, and colonies of the 15 strains selected in the secondary evaluation and JM109/pSTT002 were inocu-

TABLE 4

| Line | Transformant | Amino acid substitution mutation (*1) | Codon mutation | Name of transformant (*2) |
|---|---|---|---|---|
| 1 | T133-1, T133-2, T133-3, T133-4, T133-7 | T133C | ACG→TGT | JM109/pSTT002-T133C |
|   | T133-5 | T133A | ACG→GCT | |
|   | T133-6 | T133S | ACG→TCT | JM109/pSTT002-T133S |
| 2 | F136-1, F136-6 | F136S | TTC→AGT | |
|   | F136-3, F136-4, F136-5 | | TTC→TCA | |
|   | F136-2 | F136A | TTC→GCG | JM109/pSTT002-T133A |
|   | F136-7 | F136W | TTC→TGG | JM109/pSTT002-T133W |
| 3 | D199-1, D199-2, D199-3, D199-4, D199-5 | D199H | GAC→CAC | |
|   | D199-7, D199-8, D199-12 | D199E | GAC→GAG | JM109/pSTT002-D199E |
|   | D199-11 | | GAC→GAA | |
|   | D199-9 | D199Q | GAC→CAA | JM109/pSTT002-D199Q |
|   | D199-6, D199-10 | D199Y | GAC→TAT | JM109/pSTT002-D199Y |
|   | D199-9-5 | D199R | GAC→CGC | JM109/pSTT002-D199R |
|   | D199-6-2 | D199T | GAC→ACT | JM109/pSTT002-D199T |
|   | D199-4-3 | | GAC→ACC | |
|   | D199-6-4 | D199S | GAC→TCC | JM109/pSTT002-D199S |
|   | D199-13 | D199L | GAC→CTG | JM109/pSTT002-D199L |
|   | D199-14 | D199M | GAC→ATG | JM109/pSTT002-D199M |
|   | D199-15 | D199I | GAC→ATC | JM109/pSTT002-D199I |

(*1) In the halohydrin epoxidase in each of the strains, the second amino acid residue is substituted with lysine. The number indicating the position of amino acid residue is a number indicating the position of amino acid residue in the amino acid sequence of HheB (2$^{nd}$) (SEQ ID NO: 2).
(*2) Regarding amino acid substitution mutants, those which were already obtained in Example 2 or in this table were not renamed.

Halohydrin epoxidases expressed by the analyzed 33 strains and halohydrin epoxidase genes encoding them were named as described in Table 2, in consideration of overlapping with the embodiments of the amino acid substitution mutants already obtained.

Example 4

(R)-CHBN Synthesis Reaction Caused by Improved Halohydrin Epoxidase (1) Preparation of Crude Enzyme Solution of Improved Halohydrin Epoxidase In order to examine the optical purity of (R)-CHBN which was synthesized by each of the improved halohydrin epoxidases obtained in Examples 2 and 3, firstly, crude enzyme lated into the test tubes, respectively. They were cultured at 37° C. at 210 rpm for about 8 hours, and subsequently 100 µl of each of the obtained culture solutions was inoculated into LBAmp medium containing 1 mM IPTG as the final concentration (100 ml in a 500 ml conical flask) and cultured at 37° C. at 210 rpm for 16 hours. Each cell was collected from 100 ml of each of the obtained culture solutions by means of centrifugation (3,700×g, 10 minutes, 4° C.), and after washed with 20 mM Tris-sulfuric acid buffer solution (pH 8.0), the cells were" suspended in the same buffer solution so that the concentration of the cells became 12.5 gDC/L. 3 ml of the obtained suspension containing the cells was disintegrated for 10 minutes using a sonicator VP-15S (Taitec, Japan) while ice-cooling under the following conditions: output control 4, DUTY CYCLE 40%, PULS, TIMER=B mode 10s. The disintegrated suspension containing the cells was subjected to centrifugation (23,000×g, 5 minutes, 4° C.), and the supernatant was collected as a crude enzyme solution. Regarding each of the obtained crude enzyme solutions, the halohydrin epoxidase activity (dechlorination activity) was measured according to the same method as described in Example 1 (3) except that the DCP concentration of the reaction solution was 400 mM. 1 U is defined as corresponding to the enzyme level by which 1 µmol of chloride ion is detached from DCP per minute under the above-described conditions, and by dividing the activity of each of the suspensions containing cells used in the activity measurement by the fluid volume of each of the suspensions containing cells used in the activity measurement, the liquid activity of each of the suspensions containing cells was calculated.

(2) Method for Analysis

Analysis of concentrations of DCP, ECH and CHBN in the reaction solutions and analysis of the optical purity of produced CHBN, which are carried out in the (R)-CHBN synthesis reaction caused by the improved halohydrin epoxidase described later, were carried out as follows:

<Analysis of Concentrations of DCP, ECH and CHBN in the Reaction Solutions>

Analysis of concentrations of DCP, ECH and CHBN in the reaction solutions was carried out by means of reversed phase HPLC. Analytical conditions for reversed phase HPLC are shown in the table below.

TABLE g

| | | |
|---|---|---|
| Target for analysis (Retention time) DCP (about 14 minutes later), ECH (about 11 minutes later), CHBN (about 7 minutes later) | | |
| Analytical conditions | Column | Inertsil ODS-3V (GL Sciences) |
| | Mobile phase | 0.1% (v/v) phosphoric acid, 10% acetonitrile |
| | Flow rate | 1 ml/min |
| | Temperature | Column: 40° C., Differential refractometer cell: 35° C. |
| | Detection | Differential refractive index |
| | Amount for analysis | 5 µl |

100 µl of solution after reaction completion was diluted and mixed with 400 µl of the mobile phase described in the table above, and subsequently subjected to analysis under the analytical conditions described in the table above. The calibration curve was made in advance using DCP solution, ECH solution and CHBN solution, each of which had an already known concentration. Using the calibration curve, the concentrations of DCP, ECH and CHBN in the reaction solution were determined.

<Analysis of Optical Purity of Produced CHBN>

Analysis of the optical purity of produced CHBN was carried out by means of normal phase HPLC after CHBN was esterified. Analytical conditions for normal phase HPLC are shown in the table below.

TABLE h

| | | |
|---|---|---|
| Target for analysis (Retention time) (R)-CHBN-(R)-MTPA ester (about 17 minutes later), (S)-CHBN-(S)-MTPA ester (about 19 minutes later) | | |
| Analytical conditions | Column | Partsil-5 (GL Sciences) |
| | Mobile phase | n-hexane:2-propanol = 99:1 |
| | Flow rate | 1 ml/min |
| | Temperature | Column: 40° C. |
| | Detection | UV (wavelength: 254 nm) |
| | Amount for analysis | 5 µl |

To about 400 µl of solution after reaction completion, the same quantity of diisopropyl ether (hereinafter sometimes referred to as "IPE") was added and the mixture was subjected to extraction. The IPE layer was separated, and a small amount of anhydrous sodium sulfate was added thereto, followed by stirring. 100 µl of the IPE layer was separated, and 10 µl of (R)-α-methoxy-α-(trifluoromethyl)phenylacetyl chloride (hereinafter sometimes referred to as (R)-MTPA) and 40 µl of pyridine were added thereto. After the mixture was reacted at room temperature overnight, IPE was added thereto to provide a mixture in an amount of about 400 µl. 400 µl of 1N hydrochloric acid was added thereto, and the mixture was subjected to extraction twice. After that, to the separated IPE layer, 400 µl of saturated sodium bicarbonate solution was added and the mixture was subjected to extraction twice. To the separated IPE layer, a small amount of anhydrous sodium sulfate was added, followed by stirring. After that, the IPE layer was volatilized by means of an aspirator. The residue was suspended in the mobile phase described in the table above, and subsequently analysis was carried out under the analytical conditions described in the table above. From the ratio between the area of (R)-CHBN-(R)-MTPA ester and the area of (S)-CHBN-(R)-MTPA ester, the respective concentrations were calculated, and the optical purity of CHBN was calculated in the manner explained in this specification (described above).

(3) (R)-CHBN Synthesis by Improved Halohydrin Epoxidase

Using each of the crude enzyme solutions derived from the transformants expressing the respective improved halohydrin epoxidases prepared in Example 4 (1), a reaction for synthesizing CHBN from DCP was performed in the presence of potassium cyanide. The basic composition of reaction solution is shown in the table below. 2 ml reaction scale was employed.

TABLE i

| Component | Concentration in reaction solution |
|---|---|
| Respective crude enzyme solutions (active) | 10 U/ml |
| DCP | 400 mM |
| KCN | 200 mM |
| Tris-sulfuric acid buffer solution (pH 8) | 750 mM |

The reaction was performed at 20° C. for 3 hours. After the reaction was completed, analysis of the concentrations of DCP, ECH and CHBN in the reaction solution and analysis of the optical purity of the produced CHBN were carried out under the same analytical conditions as those described in Example 4 (2). Results are shown in Table 5.

TABLE 5

| Crude enzyme solution | Concentration in solution after reaction completion [mM] | | | Optical purity of CHBN |
|---|---|---|---|---|
| Original transformant | DCP | ECH | CHBN | (% ee)) |
| JM109/pSTT002-T133A | 247 | 29 | 87 | 93.1 |
| JM109/pSTT002-T133C | 250 | 33 | 88 | 93.9 |
| JM109/pSTT002-T133S | 243 | 31 | 91 | 91.5 |
| JM109/pSTT002-F136A | 245 | 29 | 90 | 90.1 |
| JM109/pSTT002-F136S | 247 | 30 | 92 | 90.1 |
| JM109/pSTT002-F136W | 260 | 36 | 85 | 92.0 |
| JM109/pSTT002-D199Q | 180 | 27 | 148 | 97.7 |
| JM109/pSTT002-D199E | 201 | 29 | 144 | 95.5 |
| JM109/pSTT002-D199H | 215 | 36 | 114 | 96.7 |
| JM109/pSTT002-D199S | 187 | 28 | 149 | 97.8 |

TABLE 5-continued

| Crude enzyme solution | Concentration in solution after reaction completion [mM] | | | Optical purity of CHBN |
|---|---|---|---|---|
| Original transformant | DCP | ECH | CHBN | (% ee)) |
| JM109/pSTT002-D199T | 218 | 40 | 105 | 97.6 |
| JM109/pSTT002-D199Y | 230 | 40 | 95 | 94.8 |
| JM109/pSTT002-D199L | 243 | 40 | 112 | 96.2 |
| JM109/pSTT002-D199M | 204 | 45 | 121 | 97.0 |
| JM109/pSTT002-D199I | 212 | 44 | 121 | 95.6 |
| JM109/pSTT002 | 264 | 30 | 77 | 91.6 |

In the case of the reaction using the crude enzyme solution derived from the transformant strain JM109/pSTT002 expressing the wild-type halohydrin epoxidase, only 77 mM CHBN was accumulated. Whereas, in the case of the reactions using the respective crude enzyme solutions derived from the respective transformant strains expressing the improved halohydrin epoxidase, 87 to 149 mM CHBN was accumulated. Thus, it was indicated that a higher concentration of product can be accumulated in these improved halohydrin epoxidases compared to the wild-type halohydrin epoxidase.

Further, the optical purity of (R)-CHBN synthesized using the crude enzyme solution derived from the transformant strain JM109/pSTT002 expressing the wild-type halohydrin epoxidase was 91.6% ee. Whereas, the optical purities of (R)-CHBN synthesized using the crude enzyme solutions derived from the respective transformant strains expressing the improved halohydrin epoxidase (JM109/pSTT002-T133A, JM109/pSTT002-T133C, JM109/pSTT002-D199Q, JM109/pSTT002-D199E, JM109/pSTT002-D199H, JM109/pSTT002-D199S, JM109/pSTT002-D199T, JM109/pSTT002-D199L, JM109/pSTT002-D199M, JM109/pSTT002-D199I and JM109/pSTT002-D199Y) were 93.1% ee to 97.8% ee. Thus, it was confirmed that the optical purities of (R)-CHBN synthesized by these improved halohydrin epoxidases were higher than the optical purity of (R)-CHBN synthesized by the wild-type halohydrin epoxidase. Therefore, it was thought that these improved halohydrin epoxidases had improved stereoselectivity with respect to DCP and/or intermediate ECH.

Example 5

Confirmation of the Activity of Improved Halohydrin Epoxidase in the Presence of Chloride Ion Chloride ion is a product produced at the time of synthesizing 4-halo-3-hydroxybutyronitrile from 1,3-dihalo-2-propanol and a cyanogen compound using halohydrin epoxidase, and can inhibit the synthetic reaction using halohydrin epoxidase. The halohydrin epoxidase activities of the wild-type halohydrin epoxidase and the improved halohydrin epoxidase in the presence of chloride ion at a high concentration were examined and subjected to comparison. Using the crude enzyme solution derived from the transformant strain JM109/pSTT002 expressing the wild-type halohydrin epoxidase and the crude enzyme solution derived from the transformant strain JM109/pSTT002-D199H expressing the improved halohydrin epoxidase prepared in Example 4, the halohydrin epoxidase activities (dechlorination activities) in the absence (0 mM)/presence (100 mM and 200 mM) of sodium chloride were measured according to the same method as described in Example 1 (3) except that the DCP concentration of the reaction solution was 400 mM and the same method as described in Example 1 (3) except that the DCP concentration of the reaction solution was 400 mM and that the sodium chloride was added to the reaction solution to the final concentration of 100 mM or 200 mM. The activities of the crude enzyme solutions derived from the respective transformants in the absence (0 mM) of sodium chloride were regarded as 100%, and values of relative activity were calculated. Results are shown in Table 6.

TABLE 6

| Crude enzyme solution | Concentration of sodium chloride in reaction solution [mM] | | |
|---|---|---|---|
| Original transformant | 0 | 100 | 200 |
| JM109/pSTT002-D199H | 100% | 91% | 78% |
| JM109/pSTT002 | 100% | 44% | 40% |

In the presence of 100 mM/200 mM chloride ion, the halohydrin epoxidase activity of the crude enzyme solution derived from the transformant strain JM109/pSTT002 expressing the wild-type halohydrin epoxidase was decreased to 44% and 40%, respectively. Whereas, even in the presence of 100 mM/200 mM chloride ion, the halohydrin epoxidase activity of the crude enzyme solution derived from the transformant strain JM109/pSTT002-D199H expressing the improved halohydrin epoxidase showed the remaining activity of 91% and 78%, respectively. Therefore, it was confirmed that the resistance to reaction inhibition by chloride ion of the improved halohydrin epoxidase was improved compared to that of the wild-type halohydrin epoxidase.

Example 6

Preparation of Transformant Expressing Improved Halohydrin Epoxidase (Host of Bacterium of the Genus *Rhodococcus*) and Evaluation Thereof (1) Preparation of Transformant Expressing Improved Halohydrin Epoxidase (Host of Bacterium of the Genus *Rhodococcus*)

Transformants expressing the improved halohydrin epoxidase (hosts of bacterium of the genus *Rhodococcus*) were prepared and evaluated. Firstly, using the expression plasmid pJHB057 described in Japanese Laid-Open Patent Publication No. 2007-49932 as the template, plasmids expressing improved halohydrin epoxidases, in which substitution mutation of threonine residue at position-141 to alanine (T141A), substitution mutation of phenylalanine residue at position-144 to serine (F144S) and substitution mutation of aspartic acid residue at position-207 to histidine (D207H) in the halohydrin epoxidase HheB ($1^{st}$) (SEQ ID NO: 1) were introduced, respectively, were prepared. As primers to be used for mutation introduction, the following primers were prepared:
MDH-05: CGCTGGCCTACAGCGCGGCGCGTTTCGCT (SEQ ID NO: 68: a sense primer consisting of 29 nucleotides, in which a codon encoding the amino acid at position-141 in the halohydrin epoxidase HheB ($1^{st}$) is GCG (encoding alanine));
MDH-06: AGCGAAACGCGCCGCGCTGTAGGCCAGCG (SEQ ID NO: 69: an antisense primer consisting of 29 nucleotides, which has a complementary sequence of MDH-05);
MDH-07: CAGCACGGCGCGTTCCGCTCAGCGCGGGT (SEQ ID NO: 70: a sense primer consisting of 29 nucleotides, in which a codon encoding the amino acid at position-144 in the halohydrin epoxidase HheB ($1^{st}$) is TCC (encoding serine));

MDH-08: ACCCGCGCTGAGCGGAACGCGCCGTGCTG (SEQ ID NO: 71: an antisense primer consisting of 29 nucleotides, which has a complementary sequence of MDH-07);
MDH-09: CGACTGCCCGAGAGCACGCGCTGCTCGCG (SEQ ID NO: 72: a sense primer consisting of 29 nucleotides, in which a codon encoding the amino acid at position-207 in the halohydrin epoxidase HheB ($1^{st}$) is CAC (encoding histidine)); and
MDH-10: CGCGAGCAGCGCGTGCTCTCGGGCAGTCG (SEQ ID NO: 73: an antisense primer consisting of 29 nucleotides, which has a complementary sequence of MDH-09).

Using the above-described primers and the template pJHB057, site-specific mutation introduction was performed by means of QuickChange Site-Directed Mutagenesis Kit (STRATAGENE). Compositions of reaction solutions (each 50 µl in total) are as shown in the table below (the purpose of line 1, line 2 and line 3 was to obtain a T141A mutant, a F144S mutant and a D207H mutant, respectively).

TABLE j

|  | Line 1 | Line 2 | Line 3 |
|---|---|---|---|
| Pfuturbo DNA polymerase (2.5 U/µl) (Stratagene) | 1 µl | 1 µl | 1 µl |
| 10× Cloned Pfu DNA polymerase reaction buffer (Stratagene) | 5 µl | 5 µl | 5 µl |
| dNTP Mixture (2.5 mM for each) | 1.25 µl | 1.25 µl | 1.25 µl |
| Sense primer (10 µM) | 1.25 µl | 1.25 µl | 1.25 µl |
| Antisense primer (10 µM) | 1.25 µl | 1.25 µl | 1.25 µl |
| Template plasmid pJHB057 (10 ng/µl) | 2 µl | 2 µl | 2 µl |
| Sterile distilled water | 39.5 µl | 39.5 µl | 39.5 µl |
| Total | 50 µl | 50 µl | 50 µl |

Combinations of primers used for the respective lines were as follows:
Line 1: sense primer MDH-05, antisense primer MDH-06
Line 2: sense primer MDH-07, antisense primer MDH-08
Line 3: sense primer MDH-09, antisense primer MDH-10

Each of the reaction solutions having the above-described composition was subjected to the thermal cycling treatment as described in the table below.

TABLE k

| Temperature | Time | Cycle number |
|---|---|---|
| 95° C. | 1 minute | — |
| ↓ | | |
| 95° C. | 50 seconds | 30 |
| 60° C. | 50 seconds | |
| 68° C. | 9 minutes | |
| ↓ | | |
| 68° C. | 15 minutes | — |

According to the attached manual, to each of the reaction solutions after subjected to the thermal cycling treatment, 1 µl of DpnI was added, and incubated at 37° C. for 1 hour. Using the DpnI treatment solution, transformation of E. coli was performed in a manner similar to that in Example 2 (1). A plurality of transformant colonies grown on an agar medium were cultured in 1.5 ml of LB Amp medium (LB medium containing 100 mg/L of ampicillin) at 37° C. overnight. After each of the obtained culture solutions was harvested, recombinant plasmids were collected using Flexi Prep (GE Healthcare Bio-Sciences). Using a capillary DNA sequencer CEQ 2000 (BECKMAN COULTER), the nucleotide sequences of the PCR amplification products cloned in the three types of plasmids were analyzed according to the attached manual, and it was confirmed that no error mutation occurred in the PCR reaction. The plasmid in which a DNA fragment from the PCR amplification product of the line 1 was cloned was designated as pJHB057-T141A. The plasmid in which a DNA fragment from the PCR amplification product of the line 2 was cloned was designated as pJHB057-F144S. The plasmid in which a DNA fragment from the PCR amplification product of the line 3 was cloned was designated as pJHB057-D207H. Further, transformants of E. coli strain JM109 including these plasmids were designated as JM109/pJHB057-T141A, JM109/pJHB057-F144S and JM109/pJHB057-D207H, respectively. (The number indicating the position of amino acid residue is a number indicating the position of amino acid residue in HheB ($1^{st}$) (SEQ ID NO: 1).)

Using the obtained pJHB057-T141A, pJHB057-F144S and pJHB057-D207H, transformation of Rhodococcus rhodochrous strain J1 (Accession No. FERM BP-1478) was performed according to the method described in Japanese Laid-Open Patent Publication No. 2007-49932. Plasmids of the obtained colonies were confirmed, and 3 types of transformants, J1/pJHB057-T141A, J1/pJHB057-F144S and J1/pJHB057-D207H were obtained.

(2) Evaluation of Transformant Expressing Improved Halohydrin Epoxidase (Host of Bacterium of the Genus Rhodococcus)

The 3 types of transformants obtained in Example 6 (1) (J1/pJHB057-T141A, J1/pJHB057-F144S and J1/pJHB057-D207H) were evaluated as follows. Each of the 3 types of transformant strains and the control J1/pJHB057 (4 strains in total) was inoculated into 100 ml of GGPK medium (1.5% glucose, 1% sodium glutamate, 0.1% Bacto yeast extract, 0.05% $K_2HPO_4$, 0.05% $KH_2PO_4$, 0.05% $MgSO_4.7H_2O$, 50 µg/ml of kanamycin, pH7.2), and subjected to shaking culture at 30° C. for 72 hours. From 100 ml of each of the obtained culture solution, each cells were collected by means of centrifugation (3,700×g, 10 minutes, 4° C.). After washed with 20 mM Tris-sulfuric acid buffer solution (pH 8), each cell was suspended in the same buffer solution so that the concentration of the cells became 12.5 gDC/L. 3 ml of the obtained suspension containing the cells was disintegrated for 10 minutes using a sonicator VP-15S (Taitec, Japan) while ice-cooling under the following conditions: output control 4, DUTY CYCLE 40%, PULS, TIMER=B mode 10s. The disintegrated suspension containing the cells was subjected to centrifugation (23,000×g, 5 minutes, 4° C.), and the supernatant was collected as a crude enzyme solution. Regarding each of the obtained crude enzyme solutions, the halohydrin epoxidase activity (dechlorination activity) was measured according to the same method as described in Example 1 (3) except that the DCP concentration of the reaction solution was 400 mM. 1 U is defined as corresponding to the enzyme level by which 1 µmol of chloride ion is detached from DCP per minute under the above-described conditions, and by dividing the activity of each of the crude enzyme solutions used in the activity measurement by the fluid volume of each of the crude enzyme solutions used in the activity measurement, the liquid activity of each of the crude enzyme solutions was calculated. Further, by dividing the liquid activity by the protein concentration, the specific activity per protein of each of the strains was calculated. The protein concentrations were measured using the Bio-Rad protein assay (Bio-Rad). Results are shown in table 7.

TABLE 7

| Transformant | Specific activity per protein [U/mg protein] |
| --- | --- |
| J1/pJHB057-T141A | 72 |
| J1/PJHB057-F144S | 72 |
| J1/pJHB057-D207H | 53 |
| J1/pJHB057 | 46 |

It was confirmed that, even in the case where a bacterium of the genus *Rhodococcus* is used as a host, the improved halohydrin epoxidases, in which substitution mutation of threonine residue at position-141 to alanine (T141A), substitution mutation of phenylalanine residue at position-144 to serine (F144S) and substitution mutation of aspartic acid residue at position-207 to histidine (D207H) in HheB (1$^{st}$) (SEQ ID NO: 1) are introduced, respectively, provide improvement of the halohydrin epoxidase activity per transformant.

Sequence Listing Free Text
SEQ ID NOs: 3 to 28: mutant peptide
SEQ ID NOs: 31 to 56: mutant DNA
SEQ ID NOs: 57 to 61: synthetic DNAs
SEQ ID NO: 62: synthetic DNA
SEQ ID NO: 62: n represents a, c, g or t (Location: 15 to 17)
SEQ ID NO: 63: synthetic DNA
SEQ ID NO: 63: n represents a, c, g or t (Location: 13 to 15)
SEQ ID NO: 64: synthetic DNA
SEQ ID NO: 64: n represents a, c, g or t (Location: 14 to 16)
SEQ ID NO: 65: synthetic DNA
SEQ ID NO: 65: n represents a, c, g or t (Location: 14 to 16)
SEQ ID NO: 66: synthetic DNA
SEQ ID NO: 66: n represents a, c, g or t (Location: 15 to 17)
SEQ ID NO: 67: synthetic DNA
SEQ ID NO: 67: n represents a, c, g or t (Location: 13 to 15)
SEQ ID NOs: 68 to 73: synthetic DNA
SEQ ID NO: 74: Xaa represents any amino acid residue (Location: 2 to 13, 15, 16 and 19)
SEQ ID NO: 75: Xaa represents any amino acid residue (Location: 2, 5 to 8 and 10)
SEQ ID NOs: 76 to 83: mutant peptide
SEQ ID NOs: 84 to 91: mutant DNA

The invention claimed is:

1. An isolated halohydrin epoxidase consisting of an amino acid sequence in which any one of or a plurality of amino acid mutations selected from (A) to (D) below are introduced into an amino acid sequence of a wild-type halohydrin epoxidase having the amino acid sequence represented by SEQ ID NO:2:
   (A) an amino acid mutation in which Ala at the 2nd position is substituted with Lys or Asn;
   (B) an amino acid mutation in which Thr at the 133rd position is substituted with Ala, Cys, or Ser;
   (C) an amino acid mutation in which Phe at the 136th position is substituted with Ala, Ser, or Trp; and
   (D) an amino acid mutation in which Asp at the 199th position is substituted with Gln, Glu, His, Ser, Thr, Tyr, Leu, Ile, or Met.

2. The isolated halohydrin epoxidase of claim 1, wherein said isolated halohydrin epoxidase consists of an amino acid sequence in which one or several amino acid residues selected from the residues at 3rd to 132nd, 134th, 135th, 137th to 198th, and 200th to 227th positions are substituted with other amino acids.

3. An isolated halohydrin epoxidase collected from a culture obtained by culturing a transformant or transductant obtained by introducing a recombinant vector comprising a gene encoding the isolated halohydrin epoxidase according to claim 1 into a host.

4. A method for producing an isolated halohydrin epoxidase, wherein a transformant or transductant obtained by introducing a recombinant vector comprising a gene encoding the isolated halohydrin epoxidase according to claim 1 is cultured and the isolated halohydrin epoxidase obtained from the culture is collected.

5. An isolated halohydrin epoxidase encoded by a DNA, which has at least 90% identity and hybridizes under stringent conditions, to a DNA consisting of a nucleotide sequence complementary to a nucleotide sequence encoding an amino acid sequence of the isolated halohydrin epoxidase of claim 1, wherein the stringent conditions comprise at the time of washing a salt concentration of 600 to 900 mM and a temperature of 65° C.

6. The isolated halohydrin epoxidase according to claim 2, wherein said isolated halohydrin epoxidase is encoded by a DNA, which has at least 90% identity and hybridizes under stringent conditions, to a DNA consisting of a nucleotide sequence complementary to a nucleotide sequence encoding an amino acid sequence of the isolated halohydrin epoxidase of claim 1, wherein the stringent conditions comprise at the time of washing a salt concentration of 600 to 900 mM and a temperature of 65° C.

7. An isolated halohydrin epoxidase consisting of an amino acid sequence in which any one of or a plurality of amino acid mutations selected from (A) to (D) below are introduced into an amino acid sequence of a wild-type halohydrin epoxidase having the amino acid sequence represented by SEQ ID NO:1:
   (A) an amino acid mutation in which Ala at the 2nd position is substituted with Lys or Asn;
   (B) an amino acid mutation in which Thr at the 141st position is substituted with Ala, Cys or Ser;
   (C) an amino acid mutation in which Phe at the 144th position is substituted with Ala, Ser or Trp; and
   (D) an amino acid mutation in which Asp at the 207th position is substituted with Gln, Glu, His, Ser, Thr, Tyr, Leu, Ile or Met.

8. The isolated halohydrin epoxidase of claim 7, wherein said isolated halohydrin epoxidase consists of an amino acid sequence in which one or several amino acid residues selected from the residues at 3rd to 140th, 142nd, 143rd, 145th to 206th and 208th to 235th positions are substituted with other amino acids.

9. An isolated halohydrin epoxidase encoded by a DNA, which has at least 90% identity and hybridizes under stringent conditions, to a DNA consisting of a nucleotide sequence complementary to a nucleotide sequence encoding an amino acid sequence of the isolated halohydrin epoxidase of claim 7, wherein the stringent conditions comprise at the time of washing a salt concentration of 600 to 900 mM and a temperature of 65° C.

10. The isolated halohydrin epoxidase according to claim 8, wherein said isolated halohydrin epoxidase is encoded by a DNA, which has at least 90% identity and hybridizes under stringent conditions, to a DNA consisting of a nucleotide sequence complementary to a nucleotide sequence encoding an amino acid sequence of the isolated halohydrin epoxidase of claim 7, wherein the stringent conditions comprise at the time of washing a salt concentration of 600 to 900 mM and a temperature of 65° C.

11. An isolated halohydrin epoxidase collected from a culture obtained by culturing a transformant or transductant obtained by introducing a recombinant vector comprising a gene encoding the isolated halohydrin epoxidase according to claim 7 into a host.

12. A method for producing an isolated halohydrin epoxidase, wherein a transformant or transductant obtained by introducing a recombinant vector comprising a gene encoding the isolated halohydrin epoxidase according to claim 7 is cultured and the isolated halohydrin epoxidase obtained from the culture is collected.

13. The isolated halohydrin epoxidase of claim 1, wherein said isolated halohydrin epoxidase consists of an amino acid sequence in which one or several amino acid residues selected from the residues at 3rd to 117th, 137th to 189th, and 200th to 227th positions are deleted.

14. The isolated halohydrin epoxidase of claim 1, wherein said isolated halohydrin epoxidase consists of an amino acid sequence in which one or several arbitrary amino acid residues are inserted in a region, which consists of amino acid residues at 3rd to 117th, 137th to 189th, and 200th to 227th positions.

15. The isolated halohydrin epoxidase of claim 7, wherein said isolated halohydrin epoxidase consists of an amino acid sequence in which one or several amino acid residues selected from amino acid residues at 3rd to 125th, 145th to 197th and 208th to 235th positions are deleted.

16. The isolated halohydrin epoxidase of claim 7, wherein said isolated halohydrin epoxidase consists of an amino acid sequence in which one or several arbitrary amino acid residues are inserted in a region, which consists of amino acid residues at 3rd to 125th, 145th to 197th and 208th to 235th positions.

* * * * *

```
                        SEQUENCE LISTING

<160> NUMBER OF SEQ ID NOS: 91

<210> SEQ ID NO 1
<211> LENGTH: 235
<212> TYPE: PRT
<213> ORGANISM: Corynebacterium

<400> SEQUENCE: 1

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Gly Ala Glu Val Ile Ala Asp His Thr
        35                  40                  45

Asp Leu Thr Lys Val Gly Ala Ala Glu Glu Val Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
                100                 105                 110

Phe Tyr Glu Arg Asn Lys Gly Lys Ile Val Val Tyr Gly Ser Ala Ala
            115                 120                 125

Ala Met Arg Tyr Gln Glu Gly Ala Leu Ala Tyr Ser Thr Ala Arg Phe
        130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
            180                 185                 190

Ala Arg Arg Val Pro Leu Gly Arg Leu Ala Thr Ala Arg Glu Asp Ala
        195                 200                 205

Leu Leu Ala Leu Phe Leu Ala Ser Asp Glu Ser Asp Phe Ile Val Gly
    210                 215                 220
```

Lys Ser Ile Glu Phe Asp Gly Gly Trp Ala Thr
225                 230                 235

<210> SEQ ID NO 2
<211> LENGTH: 227
<212> TYPE: PRT
<213> ORGANISM: Corynebacterium

<400> SEQUENCE: 2

Met Ala Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Glu Gly
            20                  25                  30

Ala Glu Val Ile Ala Asp His Thr Asp Leu Thr Lys Val Gly Ala Ala
        35                  40                  45

Glu Glu Val Val Glu Arg Ala Gly His Ile Asp Val Leu Val Ala Asn
    50                  55                  60

Phe Ala Val Asp Ala His Phe Gly Val Thr Val Leu Glu Thr Asp Glu
65                  70                  75                  80

Glu Leu Trp Gln Thr Ala Tyr Glu Thr Ile Val His Pro Leu His Arg
                85                  90                  95

Ile Cys Arg Ala Val Leu Pro Gln Phe Tyr Glu Arg Asn Lys Gly Lys
            100                 105                 110

Ile Val Val Tyr Gly Ser Ala Ala Met Arg Tyr Gln Glu Gly Ala
        115                 120                 125

Leu Ala Tyr Ser Thr Ala Arg Phe Ala Gln Arg Gly Tyr Val Thr Ala
    130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
            180                 185                 190

Leu Ala Thr Ala Arg Glu Asp Ala Leu Leu Ala Leu Phe Leu Ala Ser
        195                 200                 205

Asp Glu Ser Asp Phe Ile Val Gly Lys Ser Ile Glu Phe Asp Gly Gly
    210                 215                 220

Trp Ala Thr
225

<210> SEQ ID NO 3
<211> LENGTH: 235
<212> TYPE: PRT
<213> ORGANISM: Artificial Sequence
<220> FEATURE:
<223> OTHER INFORMATION: Variant peptide

<400> SEQUENCE: 3

Met Lys Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Gly Ala Glu Val Ile Ala Asp His Thr
        35                  40                  45

Asp Leu Thr Lys Val Gly Ala Ala Glu Glu Val Val Glu Arg Ala Gly
    50                  55                  60

His Ile Asp Val Leu Val Ala Asn Phe Ala Val Asp Ala His Phe Gly

```
                65                  70                  75                  80
Val Thr Val Leu Glu Thr Asp Glu Glu Leu Trp Gln Thr Ala Tyr Glu
                    85                  90                  95

Thr Ile Val His Pro Leu His Arg Ile Cys Arg Ala Val Leu Pro Gln
                    100                 105                 110

Phe Tyr Glu Arg Asn Lys Gly Lys Ile Val Val Tyr Gly Ser Ala Ala
                    115                 120                 125

Ala Met Arg Tyr Gln Glu Gly Ala Leu Ala Tyr Ser Thr Ala Arg Phe
                    130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                    165                 170                 175

Tyr Phe Trp Pro Glu Arg Ile Ala Thr Asp Glu Phe Lys Glu Asp Met
                    180                 185                 190

Ala Arg Arg Val Pro Leu Gly Arg Leu Ala Thr Ala Arg Glu Asp Ala
                    195                 200                 205

Leu Leu Ala Leu Phe Leu Ala Ser Asp Glu Ser Asp Phe Ile Val Gly
                    210                 215                 220

Lys Ser Ile Glu Phe Asp Gly Gly Trp Ala Thr
225                 230                 235

<210> SEQ ID NO 4
<211> LENGTH: 235
<212> TYPE: PRT
<213> ORGANISM: Artificial Sequence
<220> FEATURE:
<223> OTHER INFORMATION: Variant peptide

<400> SEQUENCE: 4

Met Asn Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
                    20                  25                  30

Val Gln Val Phe Glu Glu Glu Gly Ala Glu Val Ile Ala Asp His Thr
                    35                  40                  45

Asp Leu Thr Lys Val Gly Ala Ala Glu Glu Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                    85                  90                  95

Thr Ile Val His Pro Leu His Arg Ile Cys Arg Ala Val Leu Pro Gln
                    100                 105                 110

Phe Tyr Glu Arg Asn Lys Gly Lys Ile Val Val Tyr Gly Ser Ala Ala
                    115                 120                 125

Ala Met Arg Tyr Gln Glu Gly Ala Leu Ala Tyr Ser Thr Ala Arg Phe
                    130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                    165                 170                 175

Tyr Phe Trp Pro Glu Arg Ile Ala Thr Asp Glu Phe Lys Glu Asp Met
                    180                 185                 190

Ala Arg Arg Val Pro Leu Gly Arg Leu Ala Thr Ala Arg Glu Asp Ala
                    195                 200                 205
```

```
Leu Leu Ala Leu Phe Leu Ala Ser Asp Glu Ser Asp Phe Ile Val Gly
    210                 215                 220

Lys Ser Ile Glu Phe Asp Gly Gly Trp Ala Thr
225                 230                 235

<210> SEQ ID NO 5
<211> LENGTH: 235
<212> TYPE: PRT
<213> ORGANISM: Artificial Sequence
<220> FEATURE:
<223> OTHER INFORMATION: Variant peptide

<400> SEQUENCE: 5

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Glu Gly Ala Glu Val Ile Ala Asp His Thr
        35                  40                  45

Asp Leu Thr Lys Val Gly Ala Ala Glu Glu Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
            100                 105                 110

Phe Tyr Glu Arg Asn Lys Gly Lys Ile Val Val Tyr Gly Ser Ala Ala
        115                 120                 125

Ala Met Arg Tyr Gln Glu Gly Ala Leu Ala Tyr Ser Ala Ala Arg Phe
    130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
            180                 185                 190

Ala Arg Arg Val Pro Leu Gly Arg Leu Ala Thr Ala Arg Glu Asp Ala
        195                 200                 205

Leu Leu Ala Leu Phe Leu Ala Ser Asp Glu Ser Asp Phe Ile Val Gly
    210                 215                 220

Lys Ser Ile Glu Phe Asp Gly Gly Trp Ala Thr
225                 230                 235

<210> SEQ ID NO 6
<211> LENGTH: 235
<212> TYPE: PRT
<213> ORGANISM: Artificial Sequence
<220> FEATURE:
<223> OTHER INFORMATION: Variant peptide

<400> SEQUENCE: 6

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Glu Gly Ala Glu Val Ile Ala Asp His Thr
        35                  40                  45
```

```
Asp Leu Thr Lys Val Gly Ala Glu Glu Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
                100                 105                 110

Phe Tyr Glu Arg Asn Lys Gly Lys Ile Val Val Tyr Gly Ser Ala Ala
                115                 120                 125

Ala Met Arg Tyr Gln Glu Gly Ala Leu Ala Tyr Ser Cys Ala Arg Phe
        130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
                180                 185                 190

Ala Arg Arg Val Pro Leu Gly Arg Leu Ala Thr Ala Arg Glu Asp Ala
        195                 200                 205

Leu Leu Ala Leu Phe Leu Ala Ser Asp Glu Ser Asp Phe Ile Val Gly
    210                 215                 220

Lys Ser Ile Glu Phe Asp Gly Gly Trp Ala Thr
225                 230                 235

<210> SEQ ID NO 7
<211> LENGTH: 235
<212> TYPE: PRT
<213> ORGANISM: Artificial Sequence
<220> FEATURE:
<223> OTHER INFORMATION: Variant peptide

<400> SEQUENCE: 7

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
                20                  25                  30

Val Gln Val Phe Glu Glu Gly Ala Glu Val Ile Ala Asp His Thr
            35                  40                  45

Asp Leu Thr Lys Val Gly Ala Glu Glu Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
                100                 105                 110

Phe Tyr Glu Arg Asn Lys Gly Lys Ile Val Val Tyr Gly Ser Ala Ala
                115                 120                 125

Ala Met Arg Tyr Gln Glu Gly Ala Leu Ala Tyr Ser Ser Ala Arg Phe
        130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175
```

-continued

Tyr Phe Trp Pro Glu Arg Ile Ala Thr Asp Glu Phe Lys Glu Asp Met
            180                 185                 190

Ala Arg Arg Val Pro Leu Gly Arg Leu Ala Thr Ala Arg Glu Asp Ala
            195                 200                 205

Leu Leu Ala Leu Phe Leu Ala Ser Asp Glu Ser Asp Phe Ile Val Gly
            210                 215                 220

Lys Ser Ile Glu Phe Asp Gly Gly Trp Ala Thr
225                 230                 235

<210> SEQ ID NO 8
<211> LENGTH: 235
<212> TYPE: PRT
<213> ORGANISM: Artificial Sequence
<220> FEATURE:
<223> OTHER INFORMATION: Variant peptide

<400> SEQUENCE: 8

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Glu Gly Ala Glu Val Ile Ala Asp His Thr
            35                  40                  45

Asp Leu Thr Lys Val Gly Ala Ala Glu Glu Val Glu Arg Ala Gly
        50                  55                  60

His Ile Asp Val Leu Val Ala Asn Phe Ala Val Asp Ala His Phe Gly
65                  70                  75                  80

Val Thr Val Leu Glu Thr Asp Glu Gly Leu Trp Gln Thr Ala Tyr Glu
                85                  90                  95

Thr Ile Val His Pro Leu His Arg Ile Cys Arg Ala Val Leu Pro Gln
            100                 105                 110

Phe Tyr Glu Arg Asn Lys Gly Lys Ile Val Val Tyr Gly Ser Ala Ala
            115                 120                 125

Ala Met Arg Tyr Gln Glu Gly Ala Leu Ala Tyr Ser Thr Ala Arg Ala
        130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
            180                 185                 190

Ala Arg Arg Val Pro Leu Gly Arg Leu Ala Thr Ala Arg Glu Asp Ala
            195                 200                 205

Leu Leu Ala Leu Phe Leu Ala Ser Asp Glu Ser Asp Phe Ile Val Gly
        210                 215                 220

Lys Ser Ile Glu Phe Asp Gly Gly Trp Ala Thr
225                 230                 235

<210> SEQ ID NO 9
<211> LENGTH: 235
<212> TYPE: PRT
<213> ORGANISM: Artificial Sequence
<220> FEATURE:
<223> OTHER INFORMATION: Variant peptide

<400> SEQUENCE: 9

Met Ala Asn Gly Arg Lys Arg Glu Met Ala Asn Gly Arg Leu Ala Gly
1               5                   10                  15

-continued

Lys Arg Val Leu Leu Thr Asn Ala Asp Ala Tyr Met Gly Glu Ala Thr
            20                  25                  30

Val Gln Val Phe Glu Glu Gly Ala Glu Val Ile Ala Asp His Thr
        35                  40                  45

Asp Leu Thr Lys Val Gly Ala Ala Glu Glu Val Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
            100                 105                 110

Phe Tyr Glu Arg Asn Lys Gly Lys Ile Val Val Tyr Gly Ser Ala Ala
        115                 120                 125

Ala Met Arg Tyr Gln Glu Gly Ala Leu Ala Tyr Ser Thr Ala Arg Ser
    130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
            180                 185                 190

Ala Arg Arg Val Pro Leu Gly Arg Leu Ala Thr Ala Arg Glu Asp Ala
        195                 200                 205

Leu Leu Ala Leu Phe Leu Ala Ser Asp Glu Ser Asp Phe Ile Val Gly
    210                 215                 220

Lys Ser Ile Glu Phe Asp Gly Gly Trp Ala Thr
225                 230                 235

<210> SEQ ID NO 10
<211> LENGTH: 235
<212> TYPE: PRT
<213> ORGANISM: Artificial Sequence
<220> FEATURE:
<223> OTHER INFORMATION: Variant peptide

<400> SEQUENCE: 10

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Gly Ala Glu Val Ile Ala Asp His Thr
        35                  40                  45

Asp Leu Thr Lys Val Gly Ala Ala Glu Glu Val Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
            100                 105                 110

Phe Tyr Glu Arg Asn Lys Gly Lys Ile Val Val Tyr Gly Ser Ala Ala
        115                 120                 125

Ala Met Arg Tyr Gln Glu Gly Ala Leu Ala Tyr Ser Thr Ala Arg Phe
    130                 135                 140

Ala Gln Arg Gly Tyr Val Thr Ala Leu Gly Pro Glu Ala Ala Arg His

```
                145                 150                 155                 160
Asn Val Asn Val Asn Phe Ile Ala Gln His Trp Thr Gln Asn Lys Glu
                    165                 170                 175
Tyr Phe Trp Pro Glu Arg Ile Ala Thr Asp Glu Phe Lys Glu Asp Met
                180                 185                 190
Ala Arg Arg Val Pro Leu Gly Arg Leu Ala Thr Ala Arg Glu Gln Ala
                195                 200                 205
Leu Leu Ala Leu Phe Leu Ala Ser Asp Glu Ser Asp Phe Ile Val Gly
            210                 215                 220
Lys Ser Ile Glu Phe Asp Gly Gly Trp Ala Thr
225                 230                 235

<210> SEQ ID NO 11
<211> LENGTH: 235
<212> TYPE: PRT
<213> ORGANISM: Artificial Sequence
<220> FEATURE:
<223> OTHER INFORMATION: Variant peptide

<400> SEQUENCE: 11

Met Ala Asn Gly Arg Lys Arg Glu Met Ala Asn Gly Arg Leu Ala Gly
1               5                   10                  15
Lys Arg Val Leu Leu Thr Asn Ala Asp Ala Tyr Met Gly Glu Ala Thr
                20                  25                  30
Val Gln Val Phe Glu Glu Gly Ala Glu Val Ile Ala Asp His Thr
                35                  40                  45
Asp Leu Thr Lys Val Gly Ala Ala Glu Glu Val Val Glu Arg Ala Gly
            50                  55                  60
His Ile Asp Val Leu Val Ala Asn Phe Ala Val Asp Ala His Phe Gly
65                  70                  75                  80
Val Thr Val Leu Glu Thr Asp Glu Glu Leu Trp Gln Thr Ala Tyr Glu
                85                  90                  95
Thr Ile Val His Pro Leu His Arg Ile Cys Arg Ala Val Leu Pro Gln
                100                 105                 110
Phe Tyr Glu Arg Asn Lys Gly Lys Ile Val Val Tyr Gly Ser Ala Ala
            115                 120                 125
Ala Met Arg Tyr Gln Glu Gly Ala Leu Ala Tyr Ser Thr Ala Arg Phe
            130                 135                 140
Ala Gln Arg Gly Tyr Val Thr Ala Leu Gly Pro Glu Ala Ala Arg His
145                 150                 155                 160
Asn Val Asn Val Asn Phe Ile Ala Gln His Trp Thr Gln Asn Lys Glu
                    165                 170                 175
Tyr Phe Trp Pro Glu Arg Ile Ala Thr Asp Glu Phe Lys Glu Asp Met
                180                 185                 190
Ala Arg Arg Val Pro Leu Gly Arg Leu Ala Thr Ala Arg Glu Glu Ala
                195                 200                 205
Leu Leu Ala Leu Phe Leu Ala Ser Asp Glu Ser Asp Phe Ile Val Gly
            210                 215                 220
Lys Ser Ile Glu Phe Asp Gly Gly Trp Ala Thr
225                 230                 235

<210> SEQ ID NO 12
<211> LENGTH: 235
<212> TYPE: PRT
<213> ORGANISM: Artificial Sequence
<220> FEATURE:
<223> OTHER INFORMATION: Variant peptide
```

-continued

<400> SEQUENCE: 12

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Gly Ala Glu Val Ile Ala Asp His Thr
        35                  40                  45

Asp Leu Thr Lys Val Gly Ala Ala Glu Glu Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
            100                 105                 110

Phe Tyr Glu Arg Asn Lys Gly Lys Ile Val Val Tyr Gly Ser Ala Ala
        115                 120                 125

Ala Met Arg Tyr Gln Glu Gly Ala Leu Ala Tyr Ser Thr Ala Arg Phe
    130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
            180                 185                 190

Ala Arg Arg Val Pro Leu Gly Arg Leu Ala Thr Ala Arg Glu His Ala
        195                 200                 205

Leu Leu Ala Leu Phe Leu Ala Ser Asp Glu Ser Asp Phe Ile Val Gly
    210                 215                 220

Lys Ser Ile Glu Phe Asp Gly Gly Trp Ala Thr
225                 230                 235

<210> SEQ ID NO 13
<211> LENGTH: 235
<212> TYPE: PRT
<213> ORGANISM: Artificial Sequence
<220> FEATURE:
<223> OTHER INFORMATION: Variant peptide

<400> SEQUENCE: 13

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Gly Ala Glu Val Ile Ala Asp His Thr
        35                  40                  45

Asp Leu Thr Lys Val Gly Ala Ala Glu Glu Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
            100                 105                 110

Phe Tyr Glu Arg Asn Lys Gly Lys Ile Val Val Tyr Gly Ser Ala Ala
        115                 120                 125

```
Ala Met Arg Tyr Gln Glu Gly Ala Leu Ala Tyr Ser Thr Ala Arg Phe
    130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
            180                 185                 190

Ala Arg Arg Val Pro Leu Gly Arg Leu Ala Thr Ala Arg Glu Ser Ala
        195                 200                 205

Leu Leu Ala Leu Phe Leu Ala Ser Asp Glu Ser Asp Phe Ile Val Gly
    210                 215                 220

Lys Ser Ile Glu Phe Asp Gly Gly Trp Ala Thr
225                 230                 235

<210> SEQ ID NO 14
<211> LENGTH: 235
<212> TYPE: PRT
<213> ORGANISM: Artificial Sequence
<220> FEATURE:
<223> OTHER INFORMATION: Variant peptide

<400> SEQUENCE: 14

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Gly Ala Glu Val Ile Ala Asp His Thr
        35                  40                  45

Asp Leu Thr Lys Val Gly Ala Ala Glu Glu Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
            100                 105                 110

Phe Tyr Glu Arg Asn Lys Gly Lys Ile Val Val Tyr Gly Ser Ala Ala
        115                 120                 125

Ala Met Arg Tyr Gln Glu Gly Ala Leu Ala Tyr Ser Thr Ala Arg Phe
    130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
            180                 185                 190

Ala Arg Arg Val Pro Leu Gly Arg Leu Ala Thr Ala Arg Glu Thr Ala
        195                 200                 205

Leu Leu Ala Leu Phe Leu Ala Ser Asp Glu Ser Asp Phe Ile Val Gly
    210                 215                 220

Lys Ser Ile Glu Phe Asp Gly Gly Trp Ala Thr
225                 230                 235

<210> SEQ ID NO 15
<211> LENGTH: 235
```

```
<212> TYPE: PRT
<213> ORGANISM: Artificial Sequence
<220> FEATURE:
<223> OTHER INFORMATION: Variant peptide

<400> SEQUENCE: 15

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Gly Ala Glu Val Ile Ala Asp His Thr
        35                  40                  45

Asp Leu Thr Lys Val Gly Ala Ala Glu Glu Val Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
            100                 105                 110

Phe Tyr Glu Arg Asn Lys Gly Lys Ile Val Val Tyr Gly Ser Ala Ala
        115                 120                 125

Ala Met Arg Tyr Gln Glu Gly Ala Leu Ala Tyr Ser Thr Ala Arg Phe
    130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
            180                 185                 190

Ala Arg Arg Val Pro Leu Gly Arg Leu Ala Thr Ala Arg Glu Tyr Ala
        195                 200                 205

Leu Leu Ala Leu Phe Leu Ala Ser Asp Glu Ser Asp Phe Ile Val Gly
    210                 215                 220

Lys Ser Ile Glu Phe Asp Gly Gly Trp Ala Thr
225                 230                 235

<210> SEQ ID NO 16
<211> LENGTH: 227
<212> TYPE: PRT
<213> ORGANISM: Artificial Sequence
<220> FEATURE:
<223> OTHER INFORMATION: Variant peptide

<400> SEQUENCE: 16

Met Lys Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Gly
            20                  25                  30

Ala Glu Val Ile Ala Asp His Thr Asp Leu Thr Lys Val Gly Ala Ala
        35                  40                  45

Glu Glu Val Val Glu Arg Ala Gly His Ile Asp Val Leu Val Ala Asn
    50                  55                  60

Phe Ala Val Asp Ala His Phe Gly Val Thr Val Leu Glu Thr Asp Glu
65                  70                  75                  80

Glu Leu Trp Gln Thr Ala Tyr Glu Thr Ile Val His Pro Leu His Arg
                85                  90                  95
```

```
Ile Cys Arg Ala Val Leu Pro Gln Phe Tyr Glu Arg Asn Lys Gly Lys
            100                 105                 110

Ile Val Val Tyr Gly Ser Ala Ala Met Arg Tyr Gln Glu Gly Ala
            115                 120                 125

Leu Ala Tyr Ser Thr Ala Arg Phe Ala Gln Arg Gly Tyr Val Thr Ala
        130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
            165                 170                 175

Thr Asp Glu Phe Lys Glu Asp Met Ala Arg Arg Val Pro Leu Gly Arg
            180                 185                 190

Leu Ala Thr Ala Arg Glu Asp Ala Leu Leu Ala Leu Phe Leu Ala Ser
        195                 200                 205

Asp Glu Ser Asp Phe Ile Val Gly Lys Ser Ile Glu Phe Asp Gly Gly
    210                 215                 220

Trp Ala Thr
225

<210> SEQ ID NO 17
<211> LENGTH: 227
<212> TYPE: PRT
<213> ORGANISM: Artificial Sequence
<220> FEATURE:
<223> OTHER INFORMATION: Variant peptide

<400> SEQUENCE: 17

Met Asn Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Glu Gly
            20                  25                  30

Ala Glu Val Ile Ala Asp His Thr Asp Leu Thr Lys Val Gly Ala Ala
        35                  40                  45

Glu Glu Val Val Glu Arg Ala Gly His Ile Asp Val Leu Val Ala Asn
    50                  55                  60

Phe Ala Val Asp Ala His Phe Gly Val Thr Val Leu Glu Thr Asp Glu
65                  70                  75                  80

Glu Leu Trp Gln Thr Ala Tyr Glu Thr Ile Val His Pro Leu His Arg
                85                  90                  95

Ile Cys Arg Ala Val Leu Pro Gln Phe Tyr Glu Arg Asn Lys Gly Lys
            100                 105                 110

Ile Val Val Tyr Gly Ser Ala Ala Met Arg Tyr Gln Glu Gly Ala
            115                 120                 125

Leu Ala Tyr Ser Thr Ala Arg Phe Ala Gln Arg Gly Tyr Val Thr Ala
        130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
            165                 170                 175

Thr Asp Glu Phe Lys Glu Asp Met Ala Arg Arg Val Pro Leu Gly Arg
            180                 185                 190

Leu Ala Thr Ala Arg Glu Asp Ala Leu Leu Ala Leu Phe Leu Ala Ser
        195                 200                 205

Asp Glu Ser Asp Phe Ile Val Gly Lys Ser Ile Glu Phe Asp Gly Gly
    210                 215                 220

Trp Ala Thr
```

```
<210> SEQ ID NO 18
<211> LENGTH: 227
<212> TYPE: PRT
<213> ORGANISM: Artificial Sequence
<220> FEATURE:
<223> OTHER INFORMATION: Variant peptide

<400> SEQUENCE: 18

Met Ala Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Glu Gly
            20                  25                  30

Ala Glu Val Ile Ala Asp His Thr Asp Leu Thr Lys Val Gly Ala Ala
        35                  40                  45

Glu Glu Val Val Glu Arg Ala Gly His Ile Asp Val Leu Val Ala Asn
    50                  55                  60

Phe Ala Val Asp Ala His Phe Gly Val Thr Val Leu Glu Thr Asp Glu
65                  70                  75                  80

Glu Leu Trp Gln Thr Ala Tyr Glu Thr Ile Val His Pro Leu His Arg
                85                  90                  95

Ile Cys Arg Ala Val Leu Pro Gln Phe Tyr Glu Arg Asn Lys Gly Lys
            100                 105                 110

Ile Val Val Tyr Gly Ser Ala Ala Met Arg Tyr Gln Glu Gly Ala
        115                 120                 125

Leu Ala Tyr Ser Ala Ala Arg Phe Ala Gln Arg Gly Tyr Val Thr Ala
    130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
            180                 185                 190

Leu Ala Thr Ala Arg Glu Asp Ala Leu Leu Ala Leu Phe Leu Ala Ser
    195                 200                 205

Asp Glu Ser Asp Phe Ile Val Gly Lys Ser Ile Glu Phe Asp Gly Gly
    210                 215                 220

Trp Ala Thr
225

<210> SEQ ID NO 19
<211> LENGTH: 227
<212> TYPE: PRT
<213> ORGANISM: Artificial Sequence
<220> FEATURE:
<223> OTHER INFORMATION: Variant peptide

<400> SEQUENCE: 19

Met Ala Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Glu Gly
            20                  25                  30

Ala Glu Val Ile Ala Asp His Thr Asp Leu Thr Lys Val Gly Ala Ala
        35                  40                  45

Glu Glu Val Val Glu Arg Ala Gly His Ile Asp Val Leu Val Ala Asn
    50                  55                  60

Phe Ala Val Asp Ala His Phe Gly Val Thr Val Leu Glu Thr Asp Glu
```

```
                65                  70                  75                  80
Glu Leu Trp Gln Thr Ala Tyr Glu Thr Ile Val His Pro Leu His Arg
                    85                  90                  95

Ile Cys Arg Ala Val Leu Pro Gln Phe Tyr Glu Arg Asn Lys Gly Lys
                100                 105                 110

Ile Val Val Tyr Gly Ser Ala Ala Met Arg Tyr Gln Glu Gly Ala
            115                 120                 125

Leu Ala Tyr Ser Cys Ala Arg Phe Ala Gln Arg Gly Tyr Val Thr Ala
        130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
                180                 185                 190

Leu Ala Thr Ala Arg Glu Asp Ala Leu Leu Ala Leu Phe Leu Ala Ser
            195                 200                 205

Asp Glu Ser Asp Phe Ile Val Gly Lys Ser Ile Glu Phe Asp Gly Gly
        210                 215                 220

Trp Ala Thr
225

<210> SEQ ID NO 20
<211> LENGTH: 227
<212> TYPE: PRT
<213> ORGANISM: Artificial Sequence
<220> FEATURE:
<223> OTHER INFORMATION: Variant peptide

<400> SEQUENCE: 20

Met Ala Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Glu Gly
                20                  25                  30

Ala Glu Val Ile Ala Asp His Thr Asp Leu Thr Lys Val Gly Ala Ala
            35                  40                  45

Glu Glu Val Val Glu Arg Ala Gly His Ile Asp Val Leu Val Ala Asn
        50                  55                  60

Phe Ala Val Asp Ala His Phe Gly Val Thr Val Leu Glu Thr Asp Glu
65                  70                  75                  80

Glu Leu Trp Gln Thr Ala Tyr Glu Thr Ile Val His Pro Leu His Arg
                85                  90                  95

Ile Cys Arg Ala Val Leu Pro Gln Phe Tyr Glu Arg Asn Lys Gly Lys
                100                 105                 110

Ile Val Val Tyr Gly Ser Ala Ala Met Arg Tyr Gln Glu Gly Ala
            115                 120                 125

Leu Ala Tyr Ser Ser Ala Arg Phe Ala Gln Arg Gly Tyr Val Thr Ala
        130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
                180                 185                 190

Leu Ala Thr Ala Arg Glu Asp Ala Leu Leu Ala Leu Phe Leu Ala Ser
            195                 200                 205
```

Asp Glu Ser Asp Phe Ile Val Gly Lys Ser Ile Glu Phe Asp Gly Gly
        210                 215                 220

Trp Ala Thr
225

<210> SEQ ID NO 21
<211> LENGTH: 227
<212> TYPE: PRT
<213> ORGANISM: Artificial Sequence
<220> FEATURE:
<223> OTHER INFORMATION: Variant peptide

<400> SEQUENCE: 21

Met Ala Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Glu Gly
            20                  25                  30

Ala Glu Val Ile Ala Asp His Thr Asp Leu Thr Lys Val Gly Ala Ala
        35                  40                  45

Glu Glu Val Val Glu Arg Ala Gly His Ile Asp Val Leu Val Ala Asn
50                  55                  60

Phe Ala Val Asp Ala His Phe Gly Val Thr Val Leu Glu Thr Asp Glu
65                  70                  75                  80

Glu Leu Trp Gln Thr Ala Tyr Glu Thr Ile Val His Pro Leu His Arg
                85                  90                  95

Ile Cys Arg Ala Val Leu Pro Gln Phe Tyr Glu Arg Asn Lys Gly Lys
            100                 105                 110

Ile Val Val Tyr Gly Ser Ala Ala Met Arg Tyr Gln Glu Gly Ala
        115                 120                 125

Leu Ala Tyr Ser Thr Ala Arg Ala Ala Gln Arg Gly Tyr Val Thr Ala
130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
            180                 185                 190

Leu Ala Thr Ala Arg Glu Asp Ala Leu Leu Ala Leu Phe Leu Ala Ser
        195                 200                 205

Asp Glu Ser Asp Phe Ile Val Gly Lys Ser Ile Glu Phe Asp Gly Gly
    210                 215                 220

Trp Ala Thr
225

<210> SEQ ID NO 22
<211> LENGTH: 227
<212> TYPE: PRT
<213> ORGANISM: Artificial Sequence
<220> FEATURE:
<223> OTHER INFORMATION: Variant peptide

<400> SEQUENCE: 22

Met Ala Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Glu Gly
            20                  25                  30

Ala Glu Val Ile Ala Asp His Thr Asp Leu Thr Lys Val Gly Ala Ala
        35                  40                  45

```
Glu Glu Val Val Glu Arg Ala Gly His Ile Asp Val Leu Val Ala Asn
 50                  55                  60

Phe Ala Val Asp Ala His Phe Gly Val Thr Val Leu Glu Thr Asp Glu
 65                  70                  75                  80

Glu Leu Trp Gln Thr Ala Tyr Glu Thr Ile Val His Pro Leu His Arg
                 85                  90                  95

Ile Cys Arg Ala Val Leu Pro Gln Phe Tyr Glu Arg Asn Lys Gly Lys
                100                 105                 110

Ile Val Val Tyr Gly Ser Ala Ala Met Arg Tyr Gln Glu Gly Ala
                115                 120                 125

Leu Ala Tyr Ser Thr Ala Arg Ser Ala Gln Arg Gly Tyr Val Thr Ala
130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
                180                 185                 190

Leu Ala Thr Ala Arg Glu Asp Ala Leu Leu Ala Leu Phe Leu Ala Ser
                195                 200                 205

Asp Glu Ser Asp Phe Ile Val Gly Lys Ser Ile Glu Phe Asp Gly Gly
210                 215                 220

Trp Ala Thr
225

<210> SEQ ID NO 23
<211> LENGTH: 227
<212> TYPE: PRT
<213> ORGANISM: Artificial Sequence
<220> FEATURE:
<223> OTHER INFORMATION: Variant peptide

<400> SEQUENCE: 23

Met Ala Asn Gly Arg Leu Ala Gly Lys Arg Val Leu Leu Thr Asn Ala
 1               5                  10                  15

Asp Ala Tyr Met Gly Glu Ala Thr Val Gln Val Phe Glu Glu Glu Gly
                 20                  25                  30

Ala Glu Val Ile Ala Asp His Thr Asp Leu Thr Lys Val Gly Ala Ala
                 35                  40                  45

Glu Glu Val Val Glu Arg Ala Gly His Ile Asp Val Leu Val Ala Asn
 50                  55                  60

Phe Ala Val Asp Ala His Phe Gly Val Thr Val Leu Glu Thr Asp Glu
 65                  70                  75                  80

Glu Leu Trp Gln Thr Ala Tyr Glu Thr Ile Val His Pro Leu His Arg
                 85                  90                  95

Ile Cys Arg Ala Val Leu Pro Gln Phe Tyr Glu Arg Asn Lys Gly Lys
                100                 105                 110

Ile Val Val Tyr Gly Ser Ala Ala Met Arg Tyr Gln Glu Gly Ala
                115                 120                 125

Leu Ala Tyr Ser Thr Ala Arg Phe Ala Gln Arg Gly Tyr Val Thr Ala
130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175
```

```
Thr Asp Glu Phe Lys Glu Asp Met Ala Arg Arg Val Pro Leu Gly Arg
            180                 185                 190

Leu Ala Thr Ala Arg Glu Gln Ala Leu Leu Ala Leu Phe Leu Ala Ser
        195                 200                 205

Asp Glu Ser Asp Phe Ile Val Gly Lys Ser Ile Glu Phe Asp Gly Gly
    210                 215                 220

Trp Ala Thr
225

<210> SEQ ID NO 24
<211> LENGTH: 227
<212> TYPE: PRT
<213> ORGANISM: Artificial Sequence
<220> FEATURE:
<223> OTHER INFORMATION: Variant peptide

<400> SEQUENCE: 24

Met Ala Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Glu Gly
            20                  25                  30

Ala Glu Val Ile Ala Asp His Thr Asp Leu Thr Lys Val Gly Ala Ala
        35                  40                  45

Glu Glu Val Val Glu Arg Ala Gly His Ile Asp Val Leu Val Ala Asn
    50                  55                  60

Phe Ala Val Asp Ala His Phe Gly Val Thr Val Leu Glu Thr Asp Glu
65                  70                  75                  80

Glu Leu Trp Gln Thr Ala Tyr Glu Thr Ile Val His Pro Leu His Arg
                85                  90                  95

Ile Cys Arg Ala Val Leu Pro Gln Phe Tyr Arg Asn Lys Gly Lys
            100                 105                 110

Ile Val Val Tyr Gly Ser Ala Ala Ala Met Arg Tyr Gln Glu Gly Ala
        115                 120                 125

Leu Ala Tyr Ser Thr Ala Arg Phe Ala Gln Arg Gly Tyr Val Thr Ala
    130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
            180                 185                 190

Leu Ala Thr Ala Arg Glu Gln Ala Leu Leu Ala Leu Phe Leu Ala Ser
        195                 200                 205

Asp Glu Ser Asp Phe Ile Val Gly Lys Ser Ile Glu Phe Asp Gly Gly
    210                 215                 220

Trp Ala Thr
225

<210> SEQ ID NO 25
<211> LENGTH: 227
<212> TYPE: PRT
<213> ORGANISM: Artificial Sequence
<220> FEATURE:
<223> OTHER INFORMATION: Variant peptide

<400> SEQUENCE: 25

Met Ala Asn Gly Arg Leu Ala Gly Lys Arg Val Leu Leu Thr Asn Ala
1               5                   10                  15
```

```
Asp Ala Tyr Met Gly Glu Ala Thr Val Gln Val Phe Glu Glu Gly
            20                  25                  30

Ala Glu Val Ile Ala Asp His Thr Asp Leu Thr Lys Val Gly Ala Ala
            35                  40                  45

Glu Glu Val Val Glu Arg Ala Gly His Ile Asp Val Leu Val Ala Asn
 50                      55                  60

Phe Ala Val Asp Ala His Phe Gly Val Thr Val Leu Glu Thr Asp Glu
 65                  70                  75                  80

Glu Leu Trp Gln Thr Ala Tyr Glu Thr Ile Val His Pro Leu His Arg
                85                  90                  95

Ile Cys Arg Ala Val Leu Pro Gln Phe Tyr Glu Arg Asn Lys Gly Lys
            100                 105                 110

Ile Val Val Tyr Gly Ser Ala Ala Ala Met Arg Tyr Gln Glu Gly Ala
            115                 120                 125

Leu Ala Tyr Ser Thr Ala Arg Phe Ala Gln Arg Gly Tyr Val Thr Ala
            130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
            180                 185                 190

Leu Ala Thr Ala Arg Glu His Ala Leu Leu Ala Leu Phe Leu Ala Ser
            195                 200                 205

Asp Glu Ser Asp Phe Ile Val Gly Lys Ser Ile Glu Phe Asp Gly Gly
            210                 215                 220

Trp Ala Thr
225

<210> SEQ ID NO 26
<211> LENGTH: 227
<212> TYPE: PRT
<213> ORGANISM: Artificial Sequence
<220> FEATURE:
<223> OTHER INFORMATION: Variant peptide

<400> SEQUENCE: 26

Met Ala Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Gly
            20                  25                  30

Ala Glu Val Ile Ala Asp His Thr Asp Leu Thr Lys Val Gly Ala Ala
            35                  40                  45

Glu Glu Val Val Glu Arg Ala Gly His Ile Asp Val Leu Val Ala Asn
 50                      55                  60

Phe Ala Val Asp Ala His Phe Gly Val Thr Val Leu Glu Thr Asp Glu
 65                  70                  75                  80

Glu Leu Trp Gln Thr Ala Tyr Glu Thr Ile Val His Pro Leu His Arg
                85                  90                  95

Ile Cys Arg Ala Val Leu Pro Gln Phe Tyr Glu Arg Asn Lys Gly Lys
            100                 105                 110

Ile Val Val Tyr Gly Ser Ala Ala Ala Met Arg Tyr Gln Glu Gly Ala
            115                 120                 125

Leu Ala Tyr Ser Thr Ala Arg Phe Ala Gln Arg Gly Tyr Val Thr Ala
            130                 135                 140

Leu Gly Pro Glu Ala Ala Arg His Asn Val Asn Val Asn Phe Ile Ala
```

```
                 145                 150                 155                 160
Gln His Trp Thr Gln Asn Lys Glu Tyr Phe Trp Pro Glu Arg Ile Ala
                     165                 170                 175

Thr Asp Glu Phe Lys Glu Asp Met Ala Arg Arg Val Pro Leu Gly Arg
            180                 185                 190

Leu Ala Thr Ala Arg Glu Ser Ala Leu Leu Ala Leu Phe Leu Ala Ser
        195                 200                 205

Asp Glu Ser Asp Phe Ile Val Gly Lys Ser Ile Glu Phe Asp Gly Gly
    210                 215                 220

Trp Ala Thr
225

<210> SEQ ID NO 27
<211> LENGTH: 227
<212> TYPE: PRT
<213> ORGANISM: Artificial Sequence
<220> FEATURE:
<223> OTHER INFORMATION: Variant peptide

<400> SEQUENCE: 27

Met Ala Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Glu Gly
            20                  25                  30

Ala Glu Val Ile Ala Asp His Thr Asp Leu Thr Lys Val Gly Ala Ala
        35                  40                  45

Glu Glu Val Val Glu Arg Ala Gly His Ile Asp Val Leu Val Ala Asn
    50                  55                  60

Phe Ala Val Asp Ala His Phe Gly Val Thr Val Leu Glu Thr Asp Glu
65                  70                  75                  80

Glu Leu Trp Gln Thr Ala Tyr Glu Thr Ile Val His Pro Leu His Arg
                85                  90                  95

Ile Cys Arg Ala Val Leu Pro Gln Phe Tyr Glu Arg Asn Lys Gly Lys
            100                 105                 110

Ile Val Val Tyr Gly Ser Ala Ala Ala Met Arg Tyr Gln Glu Gly Ala
        115                 120                 125

Leu Ala Tyr Ser Thr Ala Arg Phe Ala Gln Arg Gly Tyr Val Thr Ala
    130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
            180                 185                 190

Leu Ala Thr Ala Arg Glu Thr Ala Leu Leu Ala Leu Phe Leu Ala Ser
        195                 200                 205

Asp Glu Ser Asp Phe Ile Val Gly Lys Ser Ile Glu Phe Asp Gly Gly
    210                 215                 220

Trp Ala Thr
225

<210> SEQ ID NO 28
<211> LENGTH: 227
<212> TYPE: PRT
<213> ORGANISM: Artificial Sequence
<220> FEATURE:
<223> OTHER INFORMATION: Variant peptide
```

<400> SEQUENCE: 28

```
Met Ala Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Glu Gly
            20                  25                  30

Ala Glu Val Ile Ala Asp His Thr Asp Leu Thr Lys Val Gly Ala Ala
        35                  40                  45

Glu Glu Val Val Glu Arg Ala Gly His Ile Asp Val Leu Val Ala Asn
    50                  55                  60

Phe Ala Val Asp Ala His Phe Gly Val Thr Val Leu Glu Thr Asp Glu
65                  70                  75                  80

Glu Leu Trp Gln Thr Ala Tyr Glu Thr Ile Val His Pro Leu His Arg
                85                  90                  95

Ile Cys Arg Ala Val Leu Pro Gln Phe Tyr Glu Arg Asn Lys Gly Lys
            100                 105                 110

Ile Val Val Tyr Gly Ser Ala Ala Ala Met Arg Tyr Gln Gly Gly Ala
        115                 120                 125

Leu Ala Tyr Ser Thr Ala Arg Phe Ala Gln Arg Gly Tyr Val Thr Ala
    130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
            180                 185                 190

Leu Ala Thr Ala Arg Glu Tyr Ala Leu Leu Ala Leu Phe Leu Ala Ser
        195                 200                 205

Asp Glu Ser Asp Phe Ile Val Gly Lys Ser Ile Glu Phe Asp Gly Gly
    210                 215                 220

Trp Ala Thr
225
```

<210> SEQ ID NO 29
<211> LENGTH: 708
<212> TYPE: DNA
<213> ORGANISM: Corynebacterium

<400> SEQUENCE: 29

```
atggctaacg gaaggaaaag ggaaatggct aacggaagac tggcaggcaa gcgggtccta      60
ctcacgaacg ccgatgccta catgggtgag gccacggtcc aggtgttcga ggaggagggc     120
gcagaggtca tcgctgacca caccgacttg acgaaggtcg cgcggcgga ggaggtcgtc     180
gagagggctg gcacatcga tgtcctggtg gccaacttcg cggtcgacgc ccacttcggg     240
gtgaccgtgc tggagaccga cgaggagctg tggcagacgg cctacgagac catcgtgcac     300
ccgctgcatc ggatctgccg tgcggtgctc ccgcagttct acgagcggaa caagggcaag     360
atcgttgtct acggaagtgc cgcagcgatg cggtaccagg aaggtgcgct ggcctacagc     420
acggcgcgtt tcgctcagcg cgggtacgtc accgccctcg gtcccgaggc agcgaggcac     480
aacgtcaacg tgaacttcat cgcccagcac tggacccaaa acaaggagta cttctggccc     540
gagcgcatcg ccaccgacga gttcaaggag gatatggcgc ccgagttcc cctgggtcgg     600
ctcgcgactg cccgagagga cgcgctgctc gcgttgttcc tggcctcgga cgagagtgac     660
ttcatcgtcg gcaagtcgat cgagttcgac ggcggctggg ccacctga              708
```

<210> SEQ ID NO 30
<211> LENGTH: 684
<212> TYPE: DNA
<213> ORGANISM: Corynebacterium

<400> SEQUENCE: 30

```
atggctaacg aagactggc aggcaagcgg gtcctactca cgaacgccga tgcctacatg      60
ggtgaggcca cggtccaggt gttcgaggag gagggcgcag aggtcatcgc tgaccacacc    120
gacttgacga aggtcggcgc ggcggaggag gtcgtcgaga gggctgggca catcgatgtc    180
ctggtggcca acttcgcggt cgacgcccac ttcggggtga ccgtgctgga gaccgacgag    240
gagctgtggc agacggccta cgagaccatc gtgcacccgc tgcatcggat ctgccgtgcg    300
gtgctcccgc agttctacga gcggaacaag ggcaagatcg ttgtctacgg aagtgccgca    360
gcgatgcggt accaggaagg tgcgctggcc tacagcacgg cgcgtttcgc tcagcgcggg    420
tacgtcaccg ccctcggtcc cgaggcagcg aggcacaacg tcaacgtgaa cttcatcgcc    480
cagcactgga cccaaaacaa ggagtacttc tggcccgagc gcatcgccac cgacgagttc    540
aaggaggata tggcgcgccg agttcccctg gtcggctcg cgactgcccg agaggacgcg    600
ctgctcgcgt tgttcctggc ctcggacgag agtgacttca tcgtcggcaa gtcgatcgag    660
ttcgacggcg gctgggccac ctga                                           684
```

<210> SEQ ID NO 31
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 31

```
atg aaa aac gga agg aaa agg gaa atg gct aac gga aga ctg gca ggc     48
Met Lys Asn Gly Arg Lys Arg Glu Met Ala Asn Gly Arg Leu Ala Gly
 1               5                  10                  15 aag cgg gtc cta ctc acg aac gcc gat gcc tac atg ggt gag gcc acg     96
Lys Arg Val Leu Leu Thr Asn Ala Asp Ala Tyr Met Gly Glu Ala Thr
             20                  25                  30 gtc cag gtg ttc gag gag gag ggc gca gag gtc atc gct gac cac acc    144
Val Gln Val Phe Glu Glu Glu Gly Ala Glu Val Ile Ala Asp His Thr
         35                  40                  45 gac ttg acg aag gtc ggc gcg gcg gag gag gtc gtc gag agg gct ggg    192
Asp Leu Thr Lys Val Gly Ala Ala Glu Glu Val Val Glu Arg Ala Gly
     50                  55                  60 cac atc gat gtc ctg gtg gcc aac ttc gcg gtc gac gcc cac ttc ggg    240
His Ile Asp Val Leu Val Ala Asn Phe Ala Val Asp Ala His Phe Gly
 65                  70                  75                  80 gtg acc gtg ctg gag acc gac gag gag ctg tgg cag acg gcc tac gag    288
Val Thr Val Leu Glu Thr Asp Glu Glu Leu Trp Gln Thr Ala Tyr Glu
                 85                  90                  95 acc atc gtg cac ccg ctg cat cgg atc tgc cgt gcg gtg ctc ccg cag    336
Thr Ile Val His Pro Leu His Arg Ile Cys Arg Ala Val Leu Pro Gln
            100                 105                 110 ttc tac gag cgg aac aag ggc aag atc gtt gtc tac gga agt gcc gca    384
Phe Tyr Glu Arg Asn Lys Gly Lys Ile Val Val Tyr Gly Ser Ala Ala
        115                 120                 125 gcg atg cgg tac cag gaa ggt gcg ctg gcc tac agc acg gcg cgt ttc    432
Ala Met Arg Tyr Gln Glu Gly Ala Leu Ala Tyr Ser Thr Ala Arg Phe
    130                 135                 140
```

```
gct cag cgc ggg tac gtc acc gcc ctc ggt ccc gag gca gcg agg cac      480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag      528
Asn Val Asn Val Asn Phe Ile Ala Gln His Trp Thr Gln Asn Lys Glu
                165                 170                 175 tac ttc tgg ccc gag cgc atc gcc acc gac gag ttc aag gag gat atg      576
Tyr Phe Trp Pro Glu Arg Ile Ala Thr Asp Glu Phe Lys Glu Asp Met
            180                 185                 190 gcg cgc cga gtt ccc ctg ggt cgg ctc gcg act gcc cga gag gac gcg      624
Ala Arg Arg Val Pro Leu Gly Arg Leu Ala Thr Ala Arg Glu Asp Ala
        195                 200                 205 ctg ctc gcg ttg ttc ctg gcc tcg gac gag agt gac ttc atc gtc ggc      672
Leu Leu Ala Leu Phe Leu Ala Ser Asp Glu Ser Asp Phe Ile Val Gly
    210                 215                 220 aag tcg atc gag ttc gac ggc ggc tgg gcc acc tga                      708
Lys Ser Ile Glu Phe Asp Gly Gly Trp Ala Thr
225                 230                 235

<210> SEQ ID NO 32
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 32 atg aac aac gga agg aaa agg gaa atg gct aac gga aga ctg gca ggc       48
Met Asn Asn Gly Arg Lys Arg Glu Met Ala Asn Gly Arg Leu Ala Gly
1               5                   10                  15 aag cgg gtc cta ctc acg aac gcc gat gcc tac atg ggt gag gcc acg       96
Lys Arg Val Leu Leu Thr Asn Ala Asp Ala Tyr Met Gly Glu Ala Thr
            20                  25                  30 gtc cag gtg ttc gag gag gag ggc gca gag gtc atc gct gac cac acc      144
Val Gln Val Phe Glu Glu Glu Gly Ala Glu Val Ile Ala Asp His Thr
        35                  40                  45 gac ttg acg aag gtc ggc gcg gcg gag gag gtc gtc gag agg gct ggg      192
Asp Leu Thr Lys Val Gly Ala Ala Glu Glu Val Val Glu Arg Ala Gly
50                  55                  60 cac atc gat gtc ctg gtg gcc aac ttc gcg gtc gac gcc cac ttc ggg      240
His Ile Asp Val Leu Val Ala Asn Phe Ala Val Asp Ala His Phe Gly
65                  70                  75                  80 gtg acc gtg ctg gag acc gac gag gag ctg tgg cag acg gcc tac gag      288
Val Thr Val Leu Glu Thr Asp Glu Glu Leu Trp Gln Thr Ala Tyr Glu
                85                  90                  95 acc atc gtg cac ccg ctg cat cgg atc tgc cgt gcg gtg ctc ccg cag      336
Thr Ile Val His Pro Leu His Arg Ile Cys Arg Ala Val Leu Pro Gln
            100                 105                 110 ttc tac gag cgg aac aag ggc aag atc gtt gtc tac gga agt gcc gca      384
Phe Tyr Glu Arg Asn Lys Gly Lys Ile Val Val Tyr Gly Ser Ala Ala
        115                 120                 125 gcg atg cgg tac cag gaa ggt gcg ctg gcc tac agc acg gcg cgt ttc      432
Ala Met Arg Tyr Gln Glu Gly Ala Leu Ala Tyr Ser Thr Ala Arg Phe
130                 135                 140 gct cag cgc ggg tac gtc acc gcc ctc ggt ccc gag gca gcg agg cac      480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag      528
Asn Val Asn Val Asn Phe Ile Ala Gln His Trp Thr Gln Asn Lys Glu
                165                 170                 175
```

```
tac ttc tgg ccc gag cgc atc gcc acc gac gag ttc aag gag gat atg        576
Tyr Phe Trp Pro Glu Arg Ile Ala Thr Asp Glu Phe Lys Glu Asp Met
            180                 185                 190 gcg cgc cga gtt ccc ctg ggt cgg ctc gcg act gcc cga gag gac gcg        624
Ala Arg Arg Val Pro Leu Gly Arg Leu Ala Thr Ala Arg Glu Asp Ala
        195                 200                 205 ctg ctc gcg ttg ttc ctg gcc tcg gac gag agt gac ttc atc gtc ggc        672
Leu Leu Ala Leu Phe Leu Ala Ser Asp Glu Ser Asp Phe Ile Val Gly
    210                 215                 220 aag tcg atc gag ttc gac ggc ggc tgg gcc acc tga                        708
Lys Ser Ile Glu Phe Asp Gly Gly Trp Ala Thr
225                 230                 235

<210> SEQ ID NO 33
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 33 atg gct aac gga agg aaa agg gaa atg gct aac gga aga ctg gca ggc         48
Met Ala Asn Gly Arg Lys Arg Glu Met Ala Asn Gly Arg Leu Ala Gly
1               5                  10                  15 aag cgg gtc cta ctc acg aac gcc gat gcc tac atg ggt gag gcc acg         96
Lys Arg Val Leu Leu Thr Asn Ala Asp Ala Tyr Met Gly Glu Ala Thr
            20                  25                  30 gtc cag gtg ttc gag gag gag ggc gca gag gtc atc gct gac cac acc        144
Val Gln Val Phe Glu Glu Glu Gly Ala Glu Val Ile Ala Asp His Thr
        35                  40                  45 gac ttg acg aag gtc ggc gcg gcg gag gag gtc gtc gag agg gct ggg        192
Asp Leu Thr Lys Val Gly Ala Ala Glu Glu Val Val Glu Arg Ala Gly
    50                  55                  60 cac atc gat gtc ctg gtg gcc aac ttc gcg gtc gac gcc cac ttc ggg        240
His Ile Asp Val Leu Val Ala Asn Phe Ala Val Asp Ala His Phe Gly
65                  70                  75                  80 gtg acc gtg ctg gag acc gac gag gag ctg tgg cag acg gcc tac gag        288
Val Thr Val Leu Glu Thr Asp Glu Glu Leu Trp Gln Thr Ala Tyr Glu
                85                  90                  95 acc atc gtg cac ccg ctg cat cgg atc tgc cgt gcg gtg ctc ccg cag        336
Thr Ile Val His Pro Leu His Arg Ile Cys Arg Ala Val Leu Pro Gln
            100                 105                 110 ttc tac gag cgg aac aag ggc aag atc gtt gtc tac gga agt gcc gca        384
Phe Tyr Glu Arg Asn Lys Gly Lys Ile Val Val Tyr Gly Ser Ala Ala
        115                 120                 125 gcg atg cgg tac cag gaa ggt gcg ctg gcc tac agc gcg gcg cgt ttc        432
Ala Met Arg Tyr Gln Glu Gly Ala Leu Ala Tyr Ser Ala Ala Arg Phe
    130                 135                 140 gct cag cgc ggg tac gtc acc gcc ctc ggt ccc gag gca gcg agg cac        480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag        528
Asn Val Asn Val Asn Phe Ile Ala Gln His Trp Thr Gln Asn Lys Glu
                165                 170                 175 tac ttc tgg ccc gag cgc atc gcc acc gac gag ttc aag gag gat atg        576
Tyr Phe Trp Pro Glu Arg Ile Ala Thr Asp Glu Phe Lys Glu Asp Met
            180                 185                 190 gcg cgc cga gtt ccc ctg ggt cgg ctc gcg act gcc cga gag gac gcg        624
Ala Arg Arg Val Pro Leu Gly Arg Leu Ala Thr Ala Arg Glu Asp Ala
```

```
ctg ctc gcg ttg ttc ctg gcc tcg gac gag agt gac ttc atc gtc ggc      672
Leu Leu Ala Leu Phe Leu Ala Ser Asp Glu Ser Asp Phe Ile Val Gly
    210                 215                 220 aag tcg atc gag ttc gac ggc ggc tgg gcc acc tga                       708
Lys Ser Ile Glu Phe Asp Gly Gly Trp Ala Thr
225                 230                 235

<210> SEQ ID NO 34
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 34 atg gct aac gga agg aaa agg gaa atg gct aac gga aga ctg gca ggc       48
Met Ala Asn Gly Arg Lys Arg Glu Met Ala Asn Gly Arg Leu Ala Gly
1               5                   10                  15 aag cgg gtc cta ctc acg aac gcc gat gcc tac atg ggt gag gcc acg       96
Lys Arg Val Leu Leu Thr Asn Ala Asp Ala Tyr Met Gly Glu Ala Thr
                20                  25                  30 gtc cag gtg ttc gag gag gag ggc gca gag gtc atc gct gac cac acc      144
Val Gln Val Phe Glu Glu Glu Gly Ala Glu Val Ile Ala Asp His Thr
            35                  40                  45 gac ttg acg aag gtc ggc gcg gcg gag gag gtc gtc gag agg gct ggg      192
Asp Leu Thr Lys Val Gly Ala Ala Glu Glu Val Val Glu Arg Ala Gly
        50                  55                  60 cac atc gat gtc ctg gtg gcc aac ttc gcg gtc gac gcc cac ttc ggg      240
His Ile Asp Val Leu Val Ala Asn Phe Ala Val Asp Ala His Phe Gly
65                  70                  75                  80 gtg acc gtg ctg gag acc gac gag gag ctg tgg cag acg gcc tac gag      288
Val Thr Val Leu Glu Thr Asp Glu Glu Leu Trp Gln Thr Ala Tyr Glu
                85                  90                  95 acc atc gtg cac ccg ctg cat cgg atc tgc cgt gcg gtg ctc ccg cag      336
Thr Ile Val His Pro Leu His Arg Ile Cys Arg Ala Val Leu Pro Gln
            100                 105                 110 ttc tac gag cgg aac aag ggc aag atc gtt gtc tac gga agt gcc gca      384
Phe Tyr Glu Arg Asn Lys Gly Lys Ile Val Val Tyr Gly Ser Ala Ala
        115                 120                 125 gcg atg cgg tac cag gaa ggt gcg ctg gcc tac agc tgt gcg cgt ttc      432
Ala Met Arg Tyr Gln Glu Gly Ala Leu Ala Tyr Ser Cys Ala Arg Phe
130                 135                 140 gct cag cgc ggg tac gtc acc gcc ctc ggt ccc gag gca gcg agg cac      480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag      528
Asn Val Asn Val Asn Phe Ile Ala Gln His Trp Thr Gln Asn Lys Glu
                165                 170                 175 tac ttc tgg ccc gag cgc atc gcc acc gac gag ttc aag gag gat atg      576
Tyr Phe Trp Pro Glu Arg Ile Ala Thr Asp Glu Phe Lys Glu Asp Met
            180                 185                 190 gcg cgc cga gtt ccc ctg ggt cgg ctc gcg act gcc cga gag gac gcg      624
Ala Arg Arg Val Pro Leu Gly Arg Leu Ala Thr Ala Arg Glu Asp Ala
        195                 200                 205 ctg ctc gcg ttg ttc ctg gcc tcg gac gag agt gac ttc atc gtc ggc      672
Leu Leu Ala Leu Phe Leu Ala Ser Asp Glu Ser Asp Phe Ile Val Gly
210                 215                 220 aag tcg atc gag ttc gac ggc ggc tgg gcc acc tga                       708
```

```
Lys Ser Ile Glu Phe Asp Gly Gly Trp Ala Thr
225                 230                 235

<210> SEQ ID NO 35
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 35 atg gct aac gga agg aaa agg gaa atg gct aac gga aga ctg gca ggc     48
Met Ala Asn Gly Arg Lys Arg Glu Met Ala Asn Gly Arg Leu Ala Gly
1               5                   10                  15 aag cgg gtc cta ctc acg aac gcc gat gcc tac atg ggt gag gcc acg     96
Lys Arg Val Leu Leu Thr Asn Ala Asp Ala Tyr Met Gly Glu Ala Thr
            20                  25                  30 gtc cag gtg ttc gag gag gag ggc gca gag gtc atc gct gac cac acc    144
Val Gln Val Phe Glu Glu Glu Gly Ala Glu Val Ile Ala Asp His Thr
        35                  40                  45 gac ttg acg aag gtc ggc gcg gcg gag gag gtc gtc gag agg gct ggg    192
Asp Leu Thr Lys Val Gly Ala Ala Glu Glu Val Val Glu Arg Ala Gly
    50                  55                  60 cac atc gat gtc ctg gtg gcc aac ttc gcg gtc gac gcc cac ttc ggg    240
His Ile Asp Val Leu Val Ala Asn Phe Ala Val Asp Ala His Phe Gly
65                  70                  75                  80 gtg acc gtg ctg gag acc gac gag gag ctg tgg cag acg gcc tac gag    288
Val Thr Val Leu Glu Thr Asp Glu Glu Leu Trp Gln Thr Ala Tyr Glu
                85                  90                  95 acc atc gtg cac ccg ctg cat cgg atc tgc cgt gcg gtg ctc ccg cag    336
Thr Ile Val His Pro Leu His Arg Ile Cys Arg Ala Val Leu Pro Gln
            100                 105                 110 ttc tac gag cgg aac aag ggc aag atc gtt gtc tac gga agt gcc gca    384
Phe Tyr Glu Arg Asn Lys Gly Lys Ile Val Val Tyr Gly Ser Ala Ala
        115                 120                 125 gcg atg cgg tac cag gaa ggt gcg ctg gcc tac agc tct gcg cgt ttc    432
Ala Met Arg Tyr Gln Glu Gly Ala Leu Ala Tyr Ser Ser Ala Arg Phe
    130                 135                 140 gct cag cgc ggg tac gtc acc gcc ctc ggt ccc gag gca gcg agg cac    480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag    528
Asn Val Asn Val Asn Phe Ile Ala Gln His Trp Thr Gln Asn Lys Glu
                165                 170                 175 tac ttc tgg ccc gag cgc atc gcc acc gac gag ttc aag gag gat atg    576
Tyr Phe Trp Pro Glu Arg Ile Ala Thr Asp Glu Phe Lys Glu Asp Met
            180                 185                 190 gcg cgc cga gtt ccc ctg ggt cgg ctc gcg act gcc cga gag gac gcg    624
Ala Arg Arg Val Pro Leu Gly Arg Leu Ala Thr Ala Arg Glu Asp Ala
        195                 200                 205 ctg ctc gcg ttg ttc ctg gcc tcg gac gag agt gac ttc atc gtc ggc    672
Leu Leu Ala Leu Phe Leu Ala Ser Asp Glu Ser Asp Phe Ile Val Gly
    210                 215                 220 aag tcg atc gag ttc gac ggc ggc tgg gcc acc tga                    708
Lys Ser Ile Glu Phe Asp Gly Gly Trp Ala Thr
225                 230                 235

<210> SEQ ID NO 36
<211> LENGTH: 708
<212> TYPE: DNA
```

<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 36

```
atg gct aac gga agg aaa agg gaa atg gct aac gga aga ctg gca ggc      48
Met Ala Asn Gly Arg Lys Arg Glu Met Ala Asn Gly Arg Leu Ala Gly
1               5                   10                  15 aag cgg gtc cta ctc acg aac gcc gat gcc tac atg ggt gag gcc acg      96
Lys Arg Val Leu Leu Thr Asn Ala Asp Ala Tyr Met Gly Glu Ala Thr
            20                  25                  30 gtc cag gtg ttc gag gag gag ggc gca gag gtc atc gct gac cac acc     144
Val Gln Val Phe Glu Glu Glu Gly Ala Glu Val Ile Ala Asp His Thr
        35                  40                  45 gac ttg acg aag gtc ggc gcg gcg gag gag gtc gtc gag agg gct ggg     192
Asp Leu Thr Lys Val Gly Ala Ala Glu Glu Val Val Glu Arg Ala Gly
    50                  55                  60 cac atc gat gtc ctg gtg gcc aac ttc gcg gtc gac gcc cac ttc ggg     240
His Ile Asp Val Leu Val Ala Asn Phe Ala Val Asp Ala His Phe Gly
65                  70                  75                  80 gtg acc gtg ctg gag acc gac gag gag ctg tgg cag acg gcc tac gag     288
Val Thr Val Leu Glu Thr Asp Glu Glu Leu Trp Gln Thr Ala Tyr Glu
                85                  90                  95 acc atc gtg cac ccg ctg cat cgg atc tgc cgt gcg gtg ctc ccg cag     336
Thr Ile Val His Pro Leu His Arg Ile Cys Arg Ala Val Leu Pro Gln
            100                 105                 110 ttc tac gag cgg aac aag ggc aag atc gtt gtc tac gga agt gcc gca     384
Phe Tyr Glu Arg Asn Lys Gly Lys Ile Val Val Tyr Gly Ser Ala Ala
        115                 120                 125 gcg atg cgg tac cag gaa ggt gcg ctg gcc tac agc acg gcg cgt gcg     432
Ala Met Arg Tyr Gln Glu Gly Ala Leu Ala Tyr Ser Thr Ala Arg Ala
    130                 135                 140 gct cag cgc ggg tac gtc acc gcc ctc ggt ccc gag gca gcg agg cac     480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag     528
Asn Val Asn Val Asn Phe Ile Ala Gln His Trp Thr Gln Asn Lys Glu
                165                 170                 175 tac ttc tgg ccc gag cgc atc gcc acc gac gag ttc aag gag gat atg     576
Tyr Phe Trp Pro Glu Arg Ile Ala Thr Asp Glu Phe Lys Glu Asp Met
            180                 185                 190 gcg cgc cga gtt ccc ctg ggt cgg ctc gcg act gcc cga gag gac gcg     624
Ala Arg Arg Val Pro Leu Gly Arg Leu Ala Thr Ala Arg Glu Asp Ala
        195                 200                 205 ctg ctc gcg ttg ttc ctg gcc tcg gac gag agt gac ttc atc gtc ggc     672
Leu Leu Ala Leu Phe Leu Ala Ser Asp Glu Ser Asp Phe Ile Val Gly
    210                 215                 220 aag tcg atc gag ttc gac ggc ggc tgg gcc acc tga                     708
Lys Ser Ile Glu Phe Asp Gly Gly Trp Ala Thr
225                 230                 235
```

<210> SEQ ID NO 37
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 37

```
atg gct aac gga agg aaa agg gaa atg gct aac gga aga ctg gca ggc    48
Met Ala Asn Gly Arg Lys Arg Glu Met Ala Asn Gly Arg Leu Ala Gly
1               5                   10                  15 aag cgg gtc cta ctc acg aac gcc gat gcc tac atg ggt gag gcc acg    96
Lys Arg Val Leu Leu Thr Asn Ala Asp Ala Tyr Met Gly Glu Ala Thr
            20                  25                  30 gtc cag gtg ttc gag gag gag ggc gca gag gtc atc gct gac cac acc    144
Val Gln Val Phe Glu Glu Glu Gly Ala Glu Val Ile Ala Asp His Thr
        35                  40                  45 gac ttg acg aag gtc ggc gcg gcg gag gag gtc gtc gag agg gct ggg    192
Asp Leu Thr Lys Val Gly Ala Ala Glu Glu Val Val Glu Arg Ala Gly
    50                  55                  60 cac atc gat gtc ctg gtg gcc aac ttc gcg gtc gac gcc cac ttc ggg    240
His Ile Asp Val Leu Val Ala Asn Phe Ala Val Asp Ala His Phe Gly
65                  70                  75                  80 gtg acc gtg ctg gag acc gac gag gag ctg tgg cag acg gcc tac gag    288
Val Thr Val Leu Glu Thr Asp Glu Glu Leu Trp Gln Thr Ala Tyr Glu
                85                  90                  95 acc atc gtg cac ccg ctg cat cgg atc tgc cgt gcg gtg ctc ccg cag    336
Thr Ile Val His Pro Leu His Arg Ile Cys Arg Ala Val Leu Pro Gln
            100                 105                 110 ttc tac gag cgg aac aag ggc aag atc gtt gtc tac gga agt gcc gca    384
Phe Tyr Glu Arg Asn Lys Gly Lys Ile Val Val Tyr Gly Ser Ala Ala
        115                 120                 125 gcg atg cgg tac cag gaa ggt gcg ctg gcc tac agc acg gcg cgt tcc    432
Ala Met Arg Tyr Gln Glu Gly Ala Leu Ala Tyr Ser Thr Ala Arg Ser
    130                 135                 140 gct cag cgc ggg tac gtc acc gcc ctc ggt ccc gag gca gcg agg cac    480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag    528
Asn Val Asn Val Asn Phe Ile Ala Gln His Trp Thr Gln Asn Lys Glu
                165                 170                 175 tac ttc tgg ccc gag cgc atc gcc acc gac gag ttc aag gag gat atg    576
Tyr Phe Trp Pro Glu Arg Ile Ala Thr Asp Glu Phe Lys Glu Asp Met
            180                 185                 190 gcg cgc cga gtt ccc ctg ggt cgg ctc gcg act gcc cga gag gac gcg    624
Ala Arg Arg Val Pro Leu Gly Arg Leu Ala Thr Ala Arg Glu Asp Ala
        195                 200                 205 ctc ctc gcg ttg ttc ctg gcc tcg gac gag agt gac ttc atc gtc ggc    672
Leu Leu Ala Leu Phe Leu Ala Ser Asp Glu Ser Asp Phe Ile Val Gly
    210                 215                 220 aag tcg atc gag ttc gac ggc ggc tgg gcc acc tga                    708
Lys Ser Ile Glu Phe Asp Gly Gly Trp Ala Thr
225                 230                 235
```

<210> SEQ ID NO 38
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 38

```
atg gct aac gga agg aaa agg gaa atg gct aac gga aga ctg gca ggc    48
Met Ala Asn Gly Arg Lys Arg Glu Met Ala Asn Gly Arg Leu Ala Gly
1               5                   10                  15 aag cgg gtc cta ctc acg aac gcc gat gcc tac atg ggt gag gcc acg    96
Lys Arg Val Leu Leu Thr Asn Ala Asp Ala Tyr Met Gly Glu Ala Thr
```

```
Lys Arg Val Leu Leu Thr Asn Ala Asp Ala Tyr Met Gly Glu Ala Thr
             20                  25                  30 gtc cag gtg ttc gag gag gag ggc gca gag gtc atc gct gac cac acc       144
Val Gln Val Phe Glu Glu Glu Gly Ala Glu Val Ile Ala Asp His Thr
         35                  40                  45 gac ttg acg aag gtc ggc gcg gcg gag gag gtc gtc gag agg gct ggg       192
Asp Leu Thr Lys Val Gly Ala Ala Glu Glu Val Val Glu Arg Ala Gly
 50                  55                  60 cac atc gat gtc ctg gtg gcc aac ttc gcg gtc gac gcc cac ttc ggg       240
His Ile Asp Val Leu Val Ala Asn Phe Ala Val Asp Ala His Phe Gly
 65                  70                  75                  80 gtg acc gtg ctg gag acc gac gag gag ctg tgg cag acg gcc tac gag       288
Val Thr Val Leu Glu Thr Asp Glu Glu Leu Trp Gln Thr Ala Tyr Glu
             85                  90                  95 acc atc gtg cac ccg ctg cat cgg atc tgc cgt gcg gtg ctc ccg cag       336
Thr Ile Val His Pro Leu His Arg Ile Cys Arg Ala Val Leu Pro Gln
        100                 105                 110 ttc tac gag cgg aac aag ggc aag atc gtt gtc tac gga agt gcc gca       384
Phe Tyr Glu Arg Asn Lys Gly Lys Ile Val Val Tyr Gly Ser Ala Ala
            115                 120                 125 gcg atg cgg tac cag gaa ggt gcg ctg gcc tac agc acg gcg cgt ttc       432
Ala Met Arg Tyr Gln Glu Gly Ala Leu Ala Tyr Ser Thr Ala Arg Phe
130                 135                 140 gct cag cgc ggg tac gtc acc gcc ctc ggt ccc gag gca gcg agg cac       480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag       528
Asn Val Asn Val Asn Phe Ile Ala Gln His Trp Thr Gln Asn Lys Glu
            165                 170                 175 tac ttc tgg ccc gag cgc atc gcc acc gac gag ttc aag gag gat atg       576
Tyr Phe Trp Pro Glu Arg Ile Ala Thr Asp Glu Phe Lys Glu Asp Met
        180                 185                 190 gcg cgc cga gtt ccc ctg ggt cgg ctc gcg act gcc cga gag caa gcg       624
Ala Arg Arg Val Pro Leu Gly Arg Leu Ala Thr Ala Arg Glu Gln Ala
            195                 200                 205 ctg ctc gcg ttg ttc ctg gcc tcg gac gag agt gac ttc atc gtc ggc       672
Leu Leu Ala Leu Phe Leu Ala Ser Asp Glu Ser Asp Phe Ile Val Gly
210                 215                 220 aag tcg atc gag ttc gac ggc ggc tgg gcc acc tga                       708
Lys Ser Ile Glu Phe Asp Gly Gly Trp Ala Thr
225                 230                 235

<210> SEQ ID NO 39
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 39 atg gct aac gga agg aaa agg gaa atg gct aac gga aga ctg gca ggc        48
Met Ala Asn Gly Arg Lys Arg Glu Met Ala Asn Gly Arg Leu Ala Gly
  1               5                  10                  15 aag cgg gtc cta ctc acg aac gcc gat gcc tac atg ggt gag gcc acg        96
Lys Arg Val Leu Leu Thr Asn Ala Asp Ala Tyr Met Gly Glu Ala Thr
             20                  25                  30 gtc cag gtg ttc gag gag gag ggc gca gag gtc atc gct gac cac acc       144
Val Gln Val Phe Glu Glu Glu Gly Ala Glu Val Ile Ala Asp His Thr
         35                  40                  45
```

| | | |
|---|---|---|
| gac ttg acg aag gtc ggc gcg gcg gag gag gtc gtc gag agg gct ggg<br>Asp Leu Thr Lys Val Gly Ala Ala Glu Glu Val Val Glu Arg Ala Gly<br>50                           55                        60 | 192 |
| cac atc gat gtc ctg gtg gcc aac ttc gcg gtc gac gcc cac ttc ggg<br>His Ile Asp Val Leu Val Ala Asn Phe Ala Val Asp Ala His Phe Gly<br>65                      70                     75                     80 | 240 |
| gtg acc gtg ctg gag acc gac gag gag ctg tgg cag acg gcc tac gag<br>Val Thr Val Leu Glu Thr Asp Glu Glu Leu Trp Gln Thr Ala Tyr Glu<br>                       85                     90                     95 | 288 |
| acc atc gtg cac ccg ctg cat cgg atc tgc cgt gcg gtg ctc ccg cag<br>Thr Ile Val His Pro Leu His Arg Ile Cys Arg Ala Val Leu Pro Gln<br>               100                   105                   110 | 336 |
| ttc tac gag cgg aac aag ggc aag atc gtt gtc tac gga agt gcc gca<br>Phe Tyr Glu Arg Asn Lys Gly Lys Ile Val Val Tyr Gly Ser Ala Ala<br>         115                   120                   125 | 384 |
| gcg atg cgg tac cag gaa ggt gcg ctg gcc tac agc acg gcg cgt ttc<br>Ala Met Arg Tyr Gln Glu Gly Ala Leu Ala Tyr Ser Thr Ala Arg Phe<br>130                       135                   140 | 432 |
| gct cag cgc ggg tac gtc acc gcc ctc ggt ccc gag gca gcg agg cac<br>Ala Gln Arg Gly Tyr Val Thr Ala Leu Gly Pro Glu Ala Ala Arg His<br>145                       150                   155                   160 | 480 |
| aac gtc aac gtg aac ttc atc gcc cag cac tgg acc caa aac aag gag<br>Asn Val Asn Val Asn Phe Ile Ala Gln His Trp Thr Gln Asn Lys Glu<br>               165                   170                   175 | 528 |
| tac ttc tgg ccc gag cgc atc gcc acc gac gag ttc aag gag gat atg<br>Tyr Phe Trp Pro Glu Arg Ile Ala Thr Asp Glu Phe Lys Glu Asp Met<br>         180                   185                   190 | 576 |
| gcg cgc cga gtt ccc ctg ggt cgg ctc gcg act gcc cga gag gag gcg<br>Ala Arg Arg Val Pro Leu Gly Arg Leu Ala Thr Ala Arg Glu Glu Ala<br>195                       200                   205 | 624 |
| ctg ctc gcg ttg ttc ctg gcc tcg gac gag agt gac ttc atc gtc ggc<br>Leu Leu Ala Leu Phe Leu Ala Ser Asp Glu Ser Asp Phe Ile Val Gly<br>210                       215                   220 | 672 |
| aag tcg atc gag ttc gac ggc ggc tgg gcc acc tga<br>Lys Ser Ile Glu Phe Asp Gly Gly Trp Ala Thr<br>225                       230                   235 | 708 |

```
<210> SEQ ID NO 40
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)
```

<400> SEQUENCE: 40

| | | |
|---|---|---|
| atg gct aac gga agg aaa agg gaa atg gct aac gga aga ctg gca ggc<br>Met Ala Asn Gly Arg Lys Arg Glu Met Ala Asn Gly Arg Leu Ala Gly<br>1                     5                     10                     15 | 48 |
| aag cgg gtc cta ctc acg aac gcc gat gcc tac atg ggt gag gcc acg<br>Lys Arg Val Leu Leu Thr Asn Ala Asp Ala Tyr Met Gly Glu Ala Thr<br>               20                   25                   30 | 96 |
| gtc cag gtg ttc gag gag gag ggc gca gag gtc atc gct gac cac acc<br>Val Gln Val Phe Glu Glu Glu Gly Ala Glu Val Ile Ala Asp His Thr<br>         35                   40                   45 | 144 |
| gac ttg acg aag gtc ggc gcg gcg gag gag gtc gtc gag agg gct ggg<br>Asp Leu Thr Lys Val Gly Ala Ala Glu Glu Val Val Glu Arg Ala Gly<br>50                           55                        60 | 192 |
| cac atc gat gtc ctg gtg gcc aac ttc gcg gtc gac gcc cac ttc ggg<br>His Ile Asp Val Leu Val Ala Asn Phe Ala Val Asp Ala His Phe Gly<br>65                      70                     75                     80 | 240 |

```
gtg acc gtg ctg gag acc gac gag gag ctg tgg cag acg gcc tac gag      288
Val Thr Val Leu Glu Thr Asp Glu Glu Leu Trp Gln Thr Ala Tyr Glu
                85                  90                  95 acc atc gtg cac ccg ctg cat cgg atc tgc cgt gcg gtg ctc ccg cag      336
Thr Ile Val His Pro Leu His Arg Ile Cys Arg Ala Val Leu Pro Gln
            100                 105                 110 ttc tac gag cgg aac aag ggc aag atc gtt gtc tac gga agt gcc gca      384
Phe Tyr Glu Arg Asn Lys Gly Lys Ile Val Val Tyr Gly Ser Ala Ala
        115                 120                 125 gcg atg cgg tac cag gaa ggt gcg ctg gcc tac agc acg gcg cgt ttc      432
Ala Met Arg Tyr Gln Glu Gly Ala Leu Ala Tyr Ser Thr Ala Arg Phe
    130                 135                 140 gct cag cgc ggg tac gtc acc gcc ctc ggt ccc gag gca gcg agg cac      480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag      528
Asn Val Asn Val Asn Phe Ile Ala Gln His Trp Thr Gln Asn Lys Glu
                165                 170                 175 tac ttc tgg ccc gag cgc atc gcc acc gac gag ttc aag gag gat atg      576
Tyr Phe Trp Pro Glu Arg Ile Ala Thr Asp Glu Phe Lys Glu Asp Met
            180                 185                 190 gcg cgc cga gtt ccc ctg ggt cgg ctc gcg act gcc cga gag cac gcg      624
Ala Arg Arg Val Pro Leu Gly Arg Leu Ala Thr Ala Arg Glu His Ala
        195                 200                 205 ctg ctc gcg ttg ttc ctg gcc tcg gac gag agt gac ttc atc gtc ggc      672
Leu Leu Ala Leu Phe Leu Ala Ser Asp Glu Ser Asp Phe Ile Val Gly
    210                 215                 220 aag tcg atc gag ttc gac ggc ggc tgg gcc acc tga                      708
Lys Ser Ile Glu Phe Asp Gly Gly Trp Ala Thr
225                 230                 235

<210> SEQ ID NO 41
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 41 atg gct aac gga agg aaa agg gaa atg gct aac gga aga ctg gca ggc       48
Met Ala Asn Gly Arg Lys Arg Glu Met Ala Asn Gly Arg Leu Ala Gly
1               5                   10                  15 aag cgg gtc cta ctc acg aac gcc gat gcc tac atg ggt gag gcc acg       96
Lys Arg Val Leu Leu Thr Asn Ala Asp Ala Tyr Met Gly Glu Ala Thr
            20                  25                  30 gtc cag gtg ttc gag gag gag ggc gca gag gtc atc gct gac cac acc      144
Val Gln Val Phe Glu Glu Glu Gly Ala Glu Val Ile Ala Asp His Thr
        35                  40                  45 gac ttg acg aag gtc ggc gcg gcg gag gag gtc gtc gag agg gct ggg      192
Asp Leu Thr Lys Val Gly Ala Ala Glu Glu Val Val Glu Arg Ala Gly
    50                  55                  60 cac atc gat gtc ctg gtg gcc aac ttc gcg gtc gac gcc cac ttc ggg      240
His Ile Asp Val Leu Val Ala Asn Phe Ala Val Asp Ala His Phe Gly
65                  70                  75                  80 gtg acc gtg ctg gag acc gac gag gag ctg tgg cag acg gcc tac gag      288
Val Thr Val Leu Glu Thr Asp Glu Glu Leu Trp Gln Thr Ala Tyr Glu
                85                  90                  95 acc atc gtg cac ccg ctg cat cgg atc tgc cgt gcg gtg ctc ccg cag      336
Thr Ile Val His Pro Leu His Arg Ile Cys Arg Ala Val Leu Pro Gln
```

```
                    100                 105                 110
ttc tac gag cgg aac aag ggc aag atc gtt gtc tac gga agt gcc gca        384
Phe Tyr Glu Arg Asn Lys Gly Lys Ile Val Val Tyr Gly Ser Ala Ala
            115                 120                 125 gcg atg cgg tac cag gaa ggt gcg ctg gcc tac agc acg gcg cgt ttc        432
Ala Met Arg Tyr Gln Glu Gly Ala Leu Ala Tyr Ser Thr Ala Arg Phe
130                 135                 140 gct cag cgc ggg tac gtc acc gcc ctc ggt ccc gag gca gcg agg cac        480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag        528
Asn Val Asn Val Asn Phe Ile Ala Gln His Trp Thr Gln Asn Lys Glu
                165                 170                 175 tac ttc tgg ccc gag cgc atc gcc acc gac gag ttc aag gag gat atg        576
Tyr Phe Trp Pro Glu Arg Ile Ala Thr Asp Glu Phe Lys Glu Asp Met
            180                 185                 190 gcg cgc cga gtt ccc ctg ggt cgg ctc gcg act gcc cga gag tcc gcg        624
Ala Arg Arg Val Pro Leu Gly Arg Leu Ala Thr Ala Arg Glu Ser Ala
        195                 200                 205 ctg ctc gcg ttg ttc ctg gcc tcg gac gag agt gac ttc atc gtc ggc        672
Leu Leu Ala Leu Phe Leu Ala Ser Asp Glu Ser Asp Phe Ile Val Gly
    210                 215                 220 aag tcg atc gag ttc gac ggc ggc tgg gcc acc tga                        708
Lys Ser Ile Glu Phe Asp Gly Gly Trp Ala Thr
225                 230                 235

<210> SEQ ID NO 42
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 42 atg gct aac gga agg aaa agg gaa atg gct aac gga aga ctg gca ggc         48
Met Ala Asn Gly Arg Lys Arg Glu Met Ala Asn Gly Arg Leu Ala Gly
1               5                   10                  15 aag cgg gtc cta ctc acg aac gcc gat gcc tac atg ggt gag gcc acg         96
Lys Arg Val Leu Leu Thr Asn Ala Asp Ala Tyr Met Gly Glu Ala Thr
            20                  25                  30 gtc cag gtg ttc gag gag gag ggc gca gag gtc atc gct gac cac acc        144
Val Gln Val Phe Glu Glu Glu Gly Ala Glu Val Ile Ala Asp His Thr
        35                  40                  45 gac ttg acg aag gtc ggc gcg gcg gag gag gtc gtc gag agg gct ggg        192
Asp Leu Thr Lys Val Gly Ala Ala Glu Glu Val Val Glu Arg Ala Gly
    50                  55                  60 cac atc gat gtc ctg gtg gcc aac ttc gcg gtc gac gcc cac ttc ggg        240
His Ile Asp Val Leu Val Ala Asn Phe Ala Val Asp Ala His Phe Gly
65                  70                  75                  80 gtg acc gtg ctg gag acc gac gag gag ctg tgg cag acg gcc tac gag        288
Val Thr Val Leu Glu Thr Asp Glu Glu Leu Trp Gln Thr Ala Tyr Glu
                85                  90                  95 acc atc gtg cac ccg ctg cat cgg atc tgc cgt gcg gtg ctc ccg cag        336
Thr Ile Val His Pro Leu His Arg Ile Cys Arg Ala Val Leu Pro Gln
            100                 105                 110 ttc tac gag cgg aac aag ggc aag atc gtt gtc tac gga agt gcc gca        384
Phe Tyr Glu Arg Asn Lys Gly Lys Ile Val Val Tyr Gly Ser Ala Ala
        115                 120                 125 gcg atg cgg tac cag gaa ggt gcg ctg gcc tac agc acg gcg cgt ttc        432
```

```
Ala Met Arg Tyr Gln Glu Gly Ala Leu Ala Tyr Ser Thr Ala Arg Phe
    130                 135                 140 gct cag cgc ggg tac gtc acc gcc ctc ggt ccc gag gca gcg agg cac      480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag      528
Asn Val Asn Val Asn Phe Ile Ala Gln His Trp Thr Gln Asn Lys Glu
                165                 170                 175 tac ttc tgg ccc gag cgc atc gcc acc gac gag ttc aag gag gat atg      576
Tyr Phe Trp Pro Glu Arg Ile Ala Thr Asp Glu Phe Lys Glu Asp Met
            180                 185                 190 gcg cgc cga gtt ccc ctg ggt cgg ctc gcg act gcc cga gag act gcg      624
Ala Arg Arg Val Pro Leu Gly Arg Leu Ala Thr Ala Arg Glu Thr Ala
        195                 200                 205 ctg ctc gcg ttg ttc ctg gcc tcg gac gag agt gac ttc atc gtc ggc      672
Leu Leu Ala Leu Phe Leu Ala Ser Asp Glu Ser Asp Phe Ile Val Gly
    210                 215                 220 aag tcg atc gag ttc gac ggc ggc tgg gcc acc tga                      708
Lys Ser Ile Glu Phe Asp Gly Gly Trp Ala Thr
225                 230                 235

<210> SEQ ID NO 43
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 43 atg gct aac gga agg aaa agg gaa atg gct aac gga aga ctg gca ggc       48
Met Ala Asn Gly Arg Lys Arg Glu Met Ala Asn Gly Arg Leu Ala Gly
1               5                   10                  15 aag cgg gtc cta ctc acg aac gcc gat gcc tac atg ggt gag gcc acg       96
Lys Arg Val Leu Leu Thr Asn Ala Asp Ala Tyr Met Gly Glu Ala Thr
                20                  25                  30 gtc cag gtg ttc gag gag gag ggc gca gag gtc atc gct gac cac acc      144
Val Gln Val Phe Glu Glu Glu Gly Ala Glu Val Ile Ala Asp His Thr
            35                  40                  45 gac ttg acg aag gtc ggc gcg gcg gag gag gtc gtc gag agg gct ggg      192
Asp Leu Thr Lys Val Gly Ala Ala Glu Glu Val Val Glu Arg Ala Gly
        50                  55                  60 cac atc gat gtc ctg gtg gcc aac ttc gcg gtc gac gcc cac ttc ggg      240
His Ile Asp Val Leu Val Ala Asn Phe Ala Val Asp Ala His Phe Gly
65                  70                  75                  80 gtg acc gtg ctg gag acc gac gag gag ctg tgg cag acg gcc tac gag      288
Val Thr Val Leu Glu Thr Asp Glu Glu Leu Trp Gln Thr Ala Tyr Glu
                85                  90                  95 acc atc gtg cac ccg ctg cat cgg atc tgc cgt gcg gtg ctc ccg cag      336
Thr Ile Val His Pro Leu His Arg Ile Cys Arg Ala Val Leu Pro Gln
            100                 105                 110 ttc tac gag cgg aac aag ggc aag atc gtt gtc tac gga agt gcc gca      384
Phe Tyr Glu Arg Asn Lys Gly Lys Ile Val Val Tyr Gly Ser Ala Ala
        115                 120                 125 gcg atg cgg tac cag gaa ggt gcg ctg gcc tac agc acg gcc cgt ttc      432
Ala Met Arg Tyr Gln Glu Gly Ala Leu Ala Tyr Ser Thr Ala Arg Phe
    130                 135                 140 gct cag cgc ggg tac gtc acc gcc ctc ggt ccc gag gca gcg agg cac      480
Ala Gln Arg Gly Tyr Val Thr Ala Leu Gly Pro Glu Ala Ala Arg His
145                 150                 155                 160
```

```
aac gtc aac gtg aac ttc atc gcc cag cac tgg acc caa aac aag gag      528
Asn Val Asn Val Asn Phe Ile Ala Gln His Trp Thr Gln Asn Lys Glu
            165                 170                 175 tac ttc tgg ccc gag cgc atc gcc acc gac gag ttc aag gag gat atg      576
Tyr Phe Trp Pro Glu Arg Ile Ala Thr Asp Glu Phe Lys Glu Asp Met
        180                 185                 190 gcg cgc cga gtt ccc ctg ggt cgg ctc gcg act gcc cga gag tat gcg      624
Ala Arg Arg Val Pro Leu Gly Arg Leu Ala Thr Ala Arg Glu Tyr Ala
    195                 200                 205 ctg ctc gcg ttg ttc ctg gcc tcg gac gag agt gac ttc atc gtc ggc      672
Leu Leu Ala Leu Phe Leu Ala Ser Asp Glu Ser Asp Phe Ile Val Gly
210                 215                 220 aag tcg atc gag ttc gac ggc ggc tgg gcc acc tga                      708
Lys Ser Ile Glu Phe Asp Gly Gly Trp Ala Thr
225                 230                 235

<210> SEQ ID NO 44
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 44 atg aaa aac gga aga ctg gca ggc aag cgg gtc cta ctc acg aac gcc       48
Met Lys Asn Gly Arg Leu Ala Gly Lys Arg Val Leu Leu Thr Asn Ala
1               5                   10                  15 gat gcc tac atg ggt gag gcc acg gtc cag gtg ttc gag gag gag ggc       96
Asp Ala Tyr Met Gly Glu Ala Thr Val Gln Val Phe Glu Glu Glu Gly
            20                  25                  30 gca gag gtc atc gct gac cac acc gac ttg acg aag gtc ggc gcg gcg      144
Ala Glu Val Ile Ala Asp His Thr Asp Leu Thr Lys Val Gly Ala Ala
        35                  40                  45 gag gag gtc gtc gag agg gct ggg cac atc gat gtc ctg gtg gcc aac      192
Glu Glu Val Val Glu Arg Ala Gly His Ile Asp Val Leu Val Ala Asn
    50                  55                  60 ttc gcg gtc gac gcc cac ttc ggg gtg acc gtg ctg gag acc gac gag      240
Phe Ala Val Asp Ala His Phe Gly Val Thr Val Leu Glu Thr Asp Glu
65                  70                  75                  80 gag ctg tgg cag acg gcc tac gag acc atc gtg cac ccg ctg cat cgg      288
Glu Leu Trp Gln Thr Ala Tyr Glu Thr Ile Val His Pro Leu His Arg
                85                  90                  95 atc tgc cgt gcg gtg ctc ccg cag ttc tac gag cgg aac aag ggc aag      336
Ile Cys Arg Ala Val Leu Pro Gln Phe Tyr Glu Arg Asn Lys Gly Lys
            100                 105                 110 atc gtt gtc tac gga agt gcc gca gcg atg cgg tac cag gaa ggt gcg      384
Ile Val Val Tyr Gly Ser Ala Ala Ala Met Arg Tyr Gln Glu Gly Ala
        115                 120                 125 ctg gcc tac agc acg gcg cgt ttc gct cag cgc ggg tac gtc acc gcc      432
Leu Ala Tyr Ser Thr Ala Arg Phe Ala Gln Arg Gly Tyr Val Thr Ala
    130                 135                 140 ctc ggt ccc gag gca gcg agg cac aac gtc aac gtg aac ttc atc gcc      480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc      528
Gln His Trp Thr Gln Asn Lys Glu Tyr Phe Trp Pro Glu Arg Ile Ala
                165                 170                 175 acc gac gag ttc aag gag gat atg gcg cgc cga gtt ccc ctg ggt cgg      576
Thr Asp Glu Phe Lys Glu Asp Met Ala Arg Arg Val Pro Leu Gly Arg
            180                 185                 190
```

| | |
|---|---|
| ctc gcg act gcc cga gag gac gcg ctg ctc gcg ttg ttc ctg gcc tcg<br>Leu Ala Thr Ala Arg Glu Asp Ala Leu Leu Ala Leu Phe Leu Ala Ser<br>        195                        200                      205 | 624 |
| gac gag agt gac ttc atc gtc ggc aag tcg atc gag ttc gac ggc ggc<br>Asp Glu Ser Asp Phe Ile Val Gly Lys Ser Ile Glu Phe Asp Gly Gly<br>    210                        215                      220 | 672 |
| tgg gcc acc tga<br>Trp Ala Thr<br>225 | 684 |

<210> SEQ ID NO 45
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 45

| | |
|---|---|
| atg aac aac gga aga ctg gca ggc aag cgg gtc cta ctc acg aac gcc<br>Met Asn Asn Gly Arg Leu Ala Gly Lys Arg Val Leu Leu Thr Asn Ala<br>1                  5                        10                      15 | 48 |
| gat gcc tac atg ggt gag gcc acg gtc cag gtg ttc gag gag gag ggc<br>Asp Ala Tyr Met Gly Glu Ala Thr Val Gln Val Phe Glu Glu Glu Gly<br>            20                        25                      30 | 96 |
| gca gag gtc atc gct gac cac acc gac ttg acg aag gtc ggc gcg gcg<br>Ala Glu Val Ile Ala Asp His Thr Asp Leu Thr Lys Val Gly Ala Ala<br>        35                        40                      45 | 144 |
| gag gag gtc gtc gag agg gct ggg cac atc gat gtc ctg gtg gcc aac<br>Glu Glu Val Val Glu Arg Ala Gly His Ile Asp Val Leu Val Ala Asn<br>50                        55                      60 | 192 |
| ttc gcg gtc gac gcc cac ttc ggg gtg acc gtg ctg gag acc gac gag<br>Phe Ala Val Asp Ala His Phe Gly Val Thr Val Leu Glu Thr Asp Glu<br>65                        70                      75                  80 | 240 |
| gag ctg tgg cag acg gcc tac gag acc atc gtg cac ccg ctg cat cgg<br>Glu Leu Trp Gln Thr Ala Tyr Glu Thr Ile Val His Pro Leu His Arg<br>                85                        90                      95 | 288 |
| atc tgc cgt gcg gtg ctc ccg cag ttc tac gag cgg aac aag ggc aag<br>Ile Cys Arg Ala Val Leu Pro Gln Phe Tyr Glu Arg Asn Lys Gly Lys<br>            100                        105                      110 | 336 |
| atc gtt gtc tac gga agt gcc gca gcg atg cgg tac cag gaa ggt gcg<br>Ile Val Val Tyr Gly Ser Ala Ala Ala Met Arg Tyr Gln Glu Gly Ala<br>        115                        120                      125 | 384 |
| ctg gcc tac agc acg gcg cgt ttc gct cag cgc ggg tac gtc acc gcc<br>Leu Ala Tyr Ser Thr Ala Arg Phe Ala Gln Arg Gly Tyr Val Thr Ala<br>130                        135                      140 | 432 |
| ctc ggt ccc gag gca gcg agg cac aac gtc aac gtg aac ttc atc gcc<br>Leu Gly Pro Glu Ala Ala Arg His Asn Val Asn Val Asn Phe Ile Ala<br>145                      150                      155                      160 | 480 |
| cag cac tgg acc caa aac aag gag tac ttc tgg ccc gag cgc atc gcc<br>Gln His Trp Thr Gln Asn Lys Glu Tyr Phe Trp Pro Glu Arg Ile Ala<br>                165                        170                      175 | 528 |
| acc gac gag ttc aag gag gat atg gcg cgc cga gtt ccc ctg ggt cgg<br>Thr Asp Glu Phe Lys Glu Asp Met Ala Arg Arg Val Pro Leu Gly Arg<br>            180                        185                      190 | 576 |
| ctc gcg act gcc cga gag gac gcg ctg ctc gcg ttg ttc ctg gcc tcg<br>Leu Ala Thr Ala Arg Glu Asp Ala Leu Leu Ala Leu Phe Leu Ala Ser<br>        195                        200                      205 | 624 |
| gac gag agt gac ttc atc gtc ggc aag tcg atc gag ttc gac ggc ggc<br>Asp Glu Ser Asp Phe Ile Val Gly Lys Ser Ile Glu Phe Asp Gly Gly | 672 |

```
                   210                 215                 220
tgg gcc acc tga                                                          684
Trp Ala Thr
225

<210> SEQ ID NO 46
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 46 atg gct aac gga aga ctg gca ggc aag cgg gtc cta ctc acg aac gcc           48
Met Ala Asn Gly Arg Leu Ala Gly Lys Arg Val Leu Leu Thr Asn Ala
1               5                  10                  15 gat gcc tac atg ggt gag gcc acg gtc cag gtg ttc gag gag gag ggc           96
Asp Ala Tyr Met Gly Glu Ala Thr Val Gln Val Phe Glu Glu Glu Gly
                20                  25                  30 gca gag gtc atc gct gac cac acc gac ttg acg aag gtc ggc gcg gcg          144
Ala Glu Val Ile Ala Asp His Thr Asp Leu Thr Lys Val Gly Ala Ala
            35                  40                  45 gag gag gtc gtc gag agg gct ggg cac atc gat gtc ctg gtg gcc aac          192
Glu Glu Val Val Glu Arg Ala Gly His Ile Asp Val Leu Val Ala Asn
        50                  55                  60 ttc gcg gtc gac gcc cac ttc ggg gtg acc gtg ctg gag acc gac gag          240
Phe Ala Val Asp Ala His Phe Gly Val Thr Val Leu Glu Thr Asp Glu
65                  70                  75                  80 gag ctg tgg cag acg gcc tac gag acc atc gtg cac ccg ctg cat cgg          288
Glu Leu Trp Gln Thr Ala Tyr Glu Thr Ile Val His Pro Leu His Arg
                85                  90                  95 atc tgc cgt gcg gtg ctc ccg cag ttc tac gag cgg aac aag ggc aag          336
Ile Cys Arg Ala Val Leu Pro Gln Phe Tyr Glu Arg Asn Lys Gly Lys
            100                 105                 110 atc gtt gtc tac gga agt gcc gca gcg atg cgg tac cag gaa ggt gcg          384
Ile Val Val Tyr Gly Ser Ala Ala Ala Met Arg Tyr Gln Glu Gly Ala
        115                 120                 125 ctg gcc tac agc gcg gcg cgt ttc gct cag cgc ggg tac gtc acc gcc          432
Leu Ala Tyr Ser Ala Ala Arg Phe Ala Gln Arg Gly Tyr Val Thr Ala
    130                 135                 140 ctc ggt ccc gag gca gcg agg cac aac gtc aac gtg aac ttc atc gcc          480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc          528
Gln His Trp Thr Gln Asn Lys Glu Tyr Phe Trp Pro Glu Arg Ile Ala
                165                 170                 175 acc gac gag ttc aag gag gat atg gcg cgc cga gtt ccc ctg ggt cgg          576
Thr Asp Glu Phe Lys Glu Asp Met Ala Arg Arg Val Pro Leu Gly Arg
            180                 185                 190 ctc gcg act gcc cga gag gac gcg ctc ctc gcg ttg ttc ctg gcc tcg          624
Leu Ala Thr Ala Arg Glu Asp Ala Leu Leu Ala Leu Phe Leu Ala Ser
        195                 200                 205 gac gag agt gac ttc atc gtc ggc aag tcg atc gag ttc gac ggc ggc          672
Asp Glu Ser Asp Phe Ile Val Gly Lys Ser Ile Glu Phe Asp Gly Gly
    210                 215                 220 tgg gcc acc tga                                                          684
Trp Ala Thr
225
```

<210> SEQ ID NO 47
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 47

```
atg gct aac gga aga ctg gca ggc aag cgg gtc cta ctc acg aac gcc      48
Met Ala Asn Gly Arg Leu Ala Gly Lys Arg Val Leu Leu Thr Asn Ala
1               5                   10                  15 gat gcc tac atg ggt gag gcc acg gtc cag gtg ttc gag gag gag ggc      96
Asp Ala Tyr Met Gly Glu Ala Thr Val Gln Val Phe Glu Glu Glu Gly
            20                  25                  30 gca gag gtc atc gct gac cac acc gac ttg acg aag gtc ggc gcg gcg     144
Ala Glu Val Ile Ala Asp His Thr Asp Leu Thr Lys Val Gly Ala Ala
        35                  40                  45 gag gag gtc gtc gag agg gct ggg cac atc gat gtc ctg gtg gcc aac     192
Glu Glu Val Val Glu Arg Ala Gly His Ile Asp Val Leu Val Ala Asn
    50                  55                  60 ttc gcg gtc gac gcc cac ttc ggg gtg acc gtg ctg gag acc gac gag     240
Phe Ala Val Asp Ala His Phe Gly Val Thr Val Leu Glu Thr Asp Glu
65                  70                  75                  80 gag ctg tgg cag acg gcc tac gag acc atc gtg cac ccg ctg cat cgg     288
Glu Leu Trp Gln Thr Ala Tyr Glu Thr Ile Val His Pro Leu His Arg
                85                  90                  95 atc tgc cgt gcg gtg ctc ccg cag ttc tac gag cgg aac aag ggc aag     336
Ile Cys Arg Ala Val Leu Pro Gln Phe Tyr Glu Arg Asn Lys Gly Lys
            100                 105                 110 atc gtt gtc tac gga agt gcc gca gcg atg cgg tac cag gaa ggt gcg     384
Ile Val Val Tyr Gly Ser Ala Ala Ala Met Arg Tyr Gln Glu Gly Ala
        115                 120                 125 ctg gcc tac agc tgt gcg cgt ttc gct cag cgc ggg tac gtc acc gcc     432
Leu Ala Tyr Ser Cys Ala Arg Phe Ala Gln Arg Gly Tyr Val Thr Ala
    130                 135                 140 ctc ggt ccc gag gca gcg agg cac aac gtc aac gtg aac ttc atc gcc     480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc     528
Gln His Trp Thr Gln Asn Lys Glu Tyr Phe Trp Pro Glu Arg Ile Ala
                165                 170                 175 acc gac gag ttc aag gag gat atg gcg cgc cga gtt ccc ctg ggt cgg     576
Thr Asp Glu Phe Lys Glu Asp Met Ala Arg Arg Val Pro Leu Gly Arg
            180                 185                 190 ctc gcg act gcc cga gag gac gcg ctc ctc gcg ttg ttc ctg gcc tcg     624
Leu Ala Thr Ala Arg Glu Asp Ala Leu Leu Ala Leu Phe Leu Ala Ser
        195                 200                 205 gac gag agt gac ttc atc gtc ggc aag tcg atc gag ttc gac ggc ggc     672
Asp Glu Ser Asp Phe Ile Val Gly Lys Ser Ile Glu Phe Asp Gly Gly
    210                 215                 220 tgg gcc acc tga                                                      684
Trp Ala Thr
225
```

<210> SEQ ID NO 48
<211> LENGTH: 684
<212> TYPE: DNA
<213> ORGANISM: Artificial Sequence
<220> FEATURE:
<223> OTHER INFORMATION: Variant DNA
<220> FEATURE:

```
<221> NAME/KEY: CDS
<222> LOCATION: (1)..(684)

<400> SEQUENCE: 48 atg gct aac gga aga ctg gca ggc aag cgg gtc cta ctc acg aac gcc      48
Met Ala Asn Gly Arg Leu Ala Gly Lys Arg Val Leu Leu Thr Asn Ala
1               5                   10                  15 gat gcc tac atg ggt gag gcc acg gtc cag gtg ttc gag gag gag ggc      96
Asp Ala Tyr Met Gly Glu Ala Thr Val Gln Val Phe Glu Glu Glu Gly
            20                  25                  30 gca gag gtc atc gct gac cac acc gac ttg acg aag gtc ggc gcg gcg     144
Ala Glu Val Ile Ala Asp His Thr Asp Leu Thr Lys Val Gly Ala Ala
        35                  40                  45 gag gag gtc gtc gag agg gct ggg cac atc gat gtc ctg gtg gcc aac     192
Glu Glu Val Val Glu Arg Ala Gly His Ile Asp Val Leu Val Ala Asn
50                  55                  60 ttc gcg gtc gac gcc cac ttc ggg gtg acc gtg ctg gag acc gac gag     240
Phe Ala Val Asp Ala His Phe Gly Val Thr Val Leu Glu Thr Asp Glu
65                  70                  75                  80 gag ctg tgg cag acg gcc tac gag acc atc gtg cac ccg ctg cat cgg     288
Glu Leu Trp Gln Thr Ala Tyr Glu Thr Ile Val His Pro Leu His Arg
                85                  90                  95 atc tgc cgt gcg gtg ctc ccg cag ttc tac gag cgg aac aag ggc aag     336
Ile Cys Arg Ala Val Leu Pro Gln Phe Tyr Glu Arg Asn Lys Gly Lys
            100                 105                 110 atc gtt gtc tac gga agt gcc gca gcg atg cgg tac cag gaa ggt gcg     384
Ile Val Val Tyr Gly Ser Ala Ala Ala Met Arg Tyr Gln Glu Gly Ala
        115                 120                 125 ctg gcc tac agc tct gcg cgt ttc gct cag cgc ggg tac gtc acc gcc     432
Leu Ala Tyr Ser Ser Ala Arg Phe Ala Gln Arg Gly Tyr Val Thr Ala
130                 135                 140 ctc ggt ccc gag gca gcg agg cac aac gtc aac gtg aac ttc atc gcc     480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc     528
Gln His Trp Thr Gln Asn Lys Glu Tyr Phe Trp Pro Glu Arg Ile Ala
                165                 170                 175 acc gac gag ttc aag gag gat atg gcg cgc cga gtt ccc ctg ggt cgg     576
Thr Asp Glu Phe Lys Glu Asp Met Ala Arg Arg Val Pro Leu Gly Arg
            180                 185                 190 ctc gcg act gcc cga gag gac gcg ctg ctc gcg ttg ttc ctg gcc tcg     624
Leu Ala Thr Ala Arg Glu Asp Ala Leu Leu Ala Leu Phe Leu Ala Ser
        195                 200                 205 gac gag agt gac ttc atc gtc ggc aag tcg atc gag ttc gac ggc ggc     672
Asp Glu Ser Asp Phe Ile Val Gly Lys Ser Ile Glu Phe Asp Gly Gly
210                 215                 220 tgg gcc acc tga                                                      684
Trp Ala Thr
225

<210> SEQ ID NO 49
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 49 atg gct aac gga aga ctg gca ggc aag cgg gtc cta ctc acg aac gcc      48
Met Ala Asn Gly Arg Leu Ala Gly Lys Arg Val Leu Leu Thr Asn Ala
```

```
gat gcc tac atg ggt gag gcc acg gtc cag gtg ttc gag gag gag ggc      96
Asp Ala Tyr Met Gly Glu Ala Thr Val Gln Val Phe Glu Glu Glu Gly
             20                  25                  30 gca gag gtc atc gct gac cac acc gac ttg acg aag gtc ggc gcg gcg     144
Ala Glu Val Ile Ala Asp His Thr Asp Leu Thr Lys Val Gly Ala Ala
         35                  40                  45 gag gag gtc gtc gag agg gct ggg cac atc gat gtc ctg gtg gcc aac     192
Glu Glu Val Val Glu Arg Ala Gly His Ile Asp Val Leu Val Ala Asn
     50                  55                  60 ttc gcg gtc gac gcc cac ttc ggg gtg acc gtg ctg gag acc gac gag     240
Phe Ala Val Asp Ala His Phe Gly Val Thr Val Leu Glu Thr Asp Glu
 65                  70                  75                  80 gag ctg tgg cag acg gcc tac gag acc atc gtg cac ccg ctg cat cgg     288
Glu Leu Trp Gln Thr Ala Tyr Glu Thr Ile Val His Pro Leu His Arg
                 85                  90                  95 atc tgc cgt gcg gtg ctc ccg cag ttc tac gag cgg aac aag ggc aag     336
Ile Cys Arg Ala Val Leu Pro Gln Phe Tyr Glu Arg Asn Lys Gly Lys
             100                 105                 110 atc gtt gtc tac gga agt gcc gca gcg atg cgg tac cag gaa ggt gcg     384
Ile Val Val Tyr Gly Ser Ala Ala Ala Met Arg Tyr Gln Glu Gly Ala
         115                 120                 125 ctg gcc tac agc acg gcg cgt gcg gct cag cgc ggg tac gtc acc gcc     432
Leu Ala Tyr Ser Thr Ala Arg Ala Ala Gln Arg Gly Tyr Val Thr Ala
     130                 135                 140 ctc ggt ccc gag gca gcg agg cac aac gtc aac gtg aac ttc atc gcc     480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc     528
Gln His Trp Thr Gln Asn Lys Glu Tyr Phe Trp Pro Glu Arg Ile Ala
                 165                 170                 175 acc gac gag ttc aag gag gat atg gcg cgc cga gtt ccc ctg ggt cgg     576
Thr Asp Glu Phe Lys Glu Asp Met Ala Arg Arg Val Pro Leu Gly Arg
             180                 185                 190 ctc gcg act gcc cga gag gac gcg ctc ctc gcg ttg ttc ctg gcc tcg     624
Leu Ala Thr Ala Arg Glu Asp Ala Leu Leu Ala Leu Phe Leu Ala Ser
         195                 200                 205 gac gag agt gac ttc atc gtc ggc aag tcg atc gag ttc gac ggc ggc     672
Asp Glu Ser Asp Phe Ile Val Gly Lys Ser Ile Glu Phe Asp Gly Gly
     210                 215                 220 tgg gcc acc tga                                                     684
Trp Ala Thr
225

<210> SEQ ID NO 50
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 50 atg gct aac gga aga ctg gca ggc aag cgg gtc cta ctc acg aac gcc      48
Met Ala Asn Gly Arg Leu Ala Gly Lys Arg Val Leu Leu Thr Asn Ala
1               5                   10                  15 gat gcc tac atg ggt gag gcc acg gtc cag gtg ttc gag gag gag ggc      96
Asp Ala Tyr Met Gly Glu Ala Thr Val Gln Val Phe Glu Glu Glu Gly
             20                  25                  30 gca gag gtc atc gct gac cac acc gac ttg acg aag gtc ggc gcg gcg     144
```

```

Ala Glu Val Ile Ala Asp His Thr Asp Leu Thr Lys Val Gly Ala Ala
         35                  40                  45 gag gag gtc gtc gag agg gct ggg cac atc gat gtc ctg gtg gcc aac    192
Glu Glu Val Val Glu Arg Ala Gly His Ile Asp Val Leu Val Ala Asn
 50                  55                  60 ttc gcg gtc gac gcc cac ttc ggg gtg acc gtg ctg gag acc gac gag    240
Phe Ala Val Asp Ala His Phe Gly Val Thr Val Leu Glu Thr Asp Glu
 65                  70                  75                  80 gag ctg tgg cag acg gcc tac gag acc atc gtg cac ccg ctg cat cgg    288
Glu Leu Trp Gln Thr Ala Tyr Glu Thr Ile Val His Pro Leu His Arg
                 85                  90                  95 atc tgc cgt gcg gtg ctc ccg cag ttc tac gag cgg aac aag ggc aag    336
Ile Cys Arg Ala Val Leu Pro Gln Phe Tyr Glu Arg Asn Lys Gly Lys
            100                 105                 110 atc gtt gtc tac gga agt gcc gca gcg atg cgg tac cag gaa ggt gcg    384
Ile Val Val Tyr Gly Ser Ala Ala Ala Met Arg Tyr Gln Glu Gly Ala
        115                 120                 125 ctg gcc tac agc acg gcg cgt tcc gct cag cgc ggg tac gtc acc gcc    432
Leu Ala Tyr Ser Thr Ala Arg Ser Ala Gln Arg Gly Tyr Val Thr Ala
    130                 135                 140 ctc ggt ccc gag gca gcg agg cac aac gtc aac gtg aac ttc atc gcc    480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc    528
Gln His Trp Thr Gln Asn Lys Glu Tyr Phe Trp Pro Glu Arg Ile Ala
                165                 170                 175 acc gac gag ttc aag gag gat atg gcg cgc cga gtt ccc ctg ggt cgg    576
Thr Asp Glu Phe Lys Glu Asp Met Ala Arg Arg Val Pro Leu Gly Arg
            180                 185                 190 ctc gcg act gcc cga gag gac gcg ctc ctc gcg ttg ttc ctg gcc tcg    624
Leu Ala Thr Ala Arg Glu Asp Ala Leu Leu Ala Leu Phe Leu Ala Ser
        195                 200                 205 gac gag agt gac ttc atc gtc ggc aag tcg atc gag ttc gac ggc ggc    672
Asp Glu Ser Asp Phe Ile Val Gly Lys Ser Ile Glu Phe Asp Gly Gly
    210                 215                 220 tgg gcc acc tga                                                    684
Trp Ala Thr
225

<210> SEQ ID NO 51
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 51 atg gct aac gga aga ctg gca ggc aag cgg gtc cta ctc acg aac gcc     48
Met Ala Asn Gly Arg Leu Ala Gly Lys Arg Val Leu Leu Thr Asn Ala
  1               5                  10                  15 gat gcc tac atg ggt gag gcc acg gtc cag gtg ttc gag gag gag ggc     96
Asp Ala Tyr Met Gly Glu Ala Thr Val Gln Val Phe Glu Glu Glu Gly
                 20                  25                  30 gca gag gtc atc gct gac cac acc gac ttg acg aag gtc ggc gcg gcg    144
Ala Glu Val Ile Ala Asp His Thr Asp Leu Thr Lys Val Gly Ala Ala
             35                  40                  45 gag gag gtc gtc gag agg gct ggg cac atc gat gtc ctg gtg gcc aac    192
Glu Glu Val Val Glu Arg Ala Gly His Ile Asp Val Leu Val Ala Asn
 50                  55                  60
```

```
ttc gcg gtc gac gcc cac ttc ggg gtg acc gtg ctg gag acc gac gag      240
Phe Ala Val Asp Ala His Phe Gly Val Thr Val Leu Glu Thr Asp Glu
 65                  70                  75                  80 gag ctg tgg cag acg gcc tac gag acc atc gtg cac ccg ctg cat cgg      288
Glu Leu Trp Gln Thr Ala Tyr Glu Thr Ile Val His Pro Leu His Arg
                 85                  90                  95 atc tgc cgt gcg gtg ctc ccg cag ttc tac gag cgg aac aag ggc aag      336
Ile Cys Arg Ala Val Leu Pro Gln Phe Tyr Glu Arg Asn Lys Gly Lys
            100                 105                 110 atc gtt gtc tac gga agt gcc gca gcg atg cgg tac cag gaa ggt gcg      384
Ile Val Val Tyr Gly Ser Ala Ala Ala Met Arg Tyr Gln Glu Gly Ala
        115                 120                 125 ctg gcc tac agc acg gcg cgt ttc gct cag cgc ggg tac gtc acc gcc      432
Leu Ala Tyr Ser Thr Ala Arg Phe Ala Gln Arg Gly Tyr Val Thr Ala
    130                 135                 140 ctc ggt ccc gag gca gcg agg cac aac gtc aac gtg aac ttc atc gcc      480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc      528
Gln His Trp Thr Gln Asn Lys Glu Tyr Phe Trp Pro Glu Arg Ile Ala
                165                 170                 175 acc gac gag ttc aag gag gat atg gcg cgc cga gtt ccc ctg ggt cgg      576
Thr Asp Glu Phe Lys Glu Asp Met Ala Arg Arg Val Pro Leu Gly Arg
            180                 185                 190 ctc gcg act gcc cga gag caa gcg ctc ctc gcg ttg ttc ctg gcc tcg      624
Leu Ala Thr Ala Arg Glu Gln Ala Leu Leu Ala Leu Phe Leu Ala Ser
        195                 200                 205 gac gag agt gac ttc atc gtc ggc aag tcg atc gag ttc gac ggc ggc      672
Asp Glu Ser Asp Phe Ile Val Gly Lys Ser Ile Glu Phe Asp Gly Gly
    210                 215                 220 tgg gcc acc tga                                                      684
Trp Ala Thr
225

<210> SEQ ID NO 52
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 52 atg gct aac gga aga ctg gca ggc aag cgg gtc cta ctc acg aac gcc       48
Met Ala Asn Gly Arg Leu Ala Gly Lys Arg Val Leu Leu Thr Asn Ala
 1               5                  10                  15 gat gcc tac atg ggt gag gcc acg gtc cag gtg ttc gag gag gag ggc       96
Asp Ala Tyr Met Gly Glu Ala Thr Val Gln Val Phe Glu Glu Glu Gly
                20                  25                  30 gca gag gtc atc gct gac cac acc gac ttg acg aag gtc ggc gcg gcg      144
Ala Glu Val Ile Ala Asp His Thr Asp Leu Thr Lys Val Gly Ala Ala
            35                  40                  45 gag gag gtc gtc gag agg gct ggg cac atc gat gtc ctg gtg gcc aac      192
Glu Glu Val Val Glu Arg Ala Gly His Ile Asp Val Leu Val Ala Asn
        50                  55                  60 ttc gcg gtc gac gcc cac ttc ggg gtg acc gtg ctg gag acc gac gag      240
Phe Ala Val Asp Ala His Phe Gly Val Thr Val Leu Glu Thr Asp Glu
 65                  70                  75                  80 gag ctg tgg cag acg gcc tac gag acc atc gtg cac ccg ctg cat cgg      288
Glu Leu Trp Gln Thr Ala Tyr Glu Thr Ile Val His Pro Leu His Arg
                 85                  90                  95
```

```
atc tgc cgt gcg gtg ctc ccg cag ttc tac gag cgg aac aag ggc aag      336
Ile Cys Arg Ala Val Leu Pro Gln Phe Tyr Glu Arg Asn Lys Gly Lys
            100                 105                 110 atc gtt gtc tac gga agt gcc gca gcg atg cgg tac cag gaa ggt gcg      384
Ile Val Val Tyr Gly Ser Ala Ala Ala Met Arg Tyr Gln Glu Gly Ala
        115                 120                 125 ctg gcc tac agc acg gcg cgt ttc gct cag cgc ggg tac gtc acc gcc      432
Leu Ala Tyr Ser Thr Ala Arg Phe Ala Gln Arg Gly Tyr Val Thr Ala
    130                 135                 140 ctc ggt ccc gag gca gcg agg cac aac gtc aac gtg aac ttc atc gcc      480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc      528
Gln His Trp Thr Gln Asn Lys Glu Tyr Phe Trp Pro Glu Arg Ile Ala
                165                 170                 175 acc gac gag ttc aag gag gat atg gcg cgc cga gtt ccc ctg ggt cgg      576
Thr Asp Glu Phe Lys Glu Asp Met Ala Arg Arg Val Pro Leu Gly Arg
            180                 185                 190 ctc gcg act gcc cga gag gag gcg ctc ctc gcg ttg ttc ctg gcc tcg      624
Leu Ala Thr Ala Arg Glu Glu Ala Leu Leu Ala Leu Phe Leu Ala Ser
        195                 200                 205 gac gag agt gac ttc atc gtc ggc aag tcg atc gag ttc gac ggc ggc      672
Asp Glu Ser Asp Phe Ile Val Gly Lys Ser Ile Glu Phe Asp Gly Gly
    210                 215                 220 tgg gcc acc tga                                                      684
Trp Ala Thr
225

<210> SEQ ID NO 53
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 53 atg gct aac gga aga ctg gca ggc aag cgg gtc cta ctc acg aac gcc       48
Met Ala Asn Gly Arg Leu Ala Gly Lys Arg Val Leu Leu Thr Asn Ala
1               5                  10                  15 gat gcc tac atg ggt gag gcc acg gtc cag gtg ttc gag gag gag ggc       96
Asp Ala Tyr Met Gly Glu Ala Thr Val Gln Val Phe Glu Glu Glu Gly
            20                  25                  30 gca gag gtc atc gct gac cac acc gac ttg acg aag gtc ggc gcg gcg      144
Ala Glu Val Ile Ala Asp His Thr Asp Leu Thr Lys Val Gly Ala Ala
        35                  40                  45 gag gag gtc gtc gag agg gct ggg cac atc gat gtc ctg gtg gcc aac      192
Glu Glu Val Val Glu Arg Ala Gly His Ile Asp Val Leu Val Ala Asn
    50                  55                  60 ttc gcg gtc gac gcc cac ttc ggg gtg acc gtg ctg gag acc gac gag      240
Phe Ala Val Asp Ala His Phe Gly Val Thr Val Leu Glu Thr Asp Glu
65                  70                  75                  80 gag ctg tgg cag acg gcc tac gag acc atc gtg cac ccg ctg cat cgg      288
Glu Leu Trp Gln Thr Ala Tyr Glu Thr Ile Val His Pro Leu His Arg
                85                  90                  95 atc tgc cgt gcg gtg ctc ccg cag ttc tac gag cgg aac aag ggc aag      336
Ile Cys Arg Ala Val Leu Pro Gln Phe Tyr Glu Arg Asn Lys Gly Lys
            100                 105                 110 atc gtt gtc tac gga agt gcc gca gcg atg cgg tac cag gaa ggt gcg      384
Ile Val Val Tyr Gly Ser Ala Ala Ala Met Arg Tyr Gln Glu Gly Ala
```

```
ctg gcc tac agc acg gcg cgt ttc gct cag cgc ggg tac gtc acc gcc        432
Leu Ala Tyr Ser Thr Ala Arg Phe Ala Gln Arg Gly Tyr Val Thr Ala
    130                 135                 140 ctc ggt ccc gag gca gcg agg cac aac gtc aac gtg aac ttc atc gcc        480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc        528
Gln His Trp Thr Gln Asn Lys Glu Tyr Phe Trp Pro Glu Arg Ile Ala
                165                 170                 175 acc gac gag ttc aag gag gat atg gcg cgc cga gtt ccc ctg ggt cgg        576
Thr Asp Glu Phe Lys Glu Asp Met Ala Arg Arg Val Pro Leu Gly Arg
            180                 185                 190 ctc gcg act gcc cga gag cac gcg ctc ctc gcg ttg ttc ctg gcc tcg        624
Leu Ala Thr Ala Arg Glu His Ala Leu Leu Ala Leu Phe Leu Ala Ser
        195                 200                 205 gac gag agt gac ttc atc gtc ggc aag tcg atc gag ttc gac ggc ggc        672
Asp Glu Ser Asp Phe Ile Val Gly Lys Ser Ile Glu Phe Asp Gly Gly
210                 215                 220 tgg gcc acc tga                                                         684
Trp Ala Thr
225

<210> SEQ ID NO 54
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 54 atg gct aac gga aga ctg gca ggc aag cgg gtc cta ctc acg aac gcc         48
Met Ala Asn Gly Arg Leu Ala Gly Lys Arg Val Leu Leu Thr Asn Ala
1               5                   10                  15 gat gcc tac atg ggt gag gcc acg gtc cag gtg ttc gag gag gag ggc         96
Asp Ala Tyr Met Gly Glu Ala Thr Val Gln Val Phe Glu Glu Glu Gly
                20                  25                  30 gca gag gtc atc gct gac cac acc gac ttg acg aag gtc ggc gcg gcg        144
Ala Glu Val Ile Ala Asp His Thr Asp Leu Thr Lys Val Gly Ala Ala
            35                  40                  45 gag gag gtc gtc gag agg gct ggg cac atc gat gtc ctg gtg gcc aac        192
Glu Glu Val Val Glu Arg Ala Gly His Ile Asp Val Leu Val Ala Asn
        50                  55                  60 ttc gcg gtc gac gcc cac ttc ggg gtg acc gtg ctg gag acc gac gag        240
Phe Ala Val Asp Ala His Phe Gly Val Thr Val Leu Glu Thr Asp Glu
65                  70                  75                  80 gag ctg tgg cag acg gcc tac gag acc atc gtg cac ccg ctg cat cgg        288
Glu Leu Trp Gln Thr Ala Tyr Glu Thr Ile Val His Pro Leu His Arg
                85                  90                  95 atc tgc cgt gcg gtg ctc ccg cag ttc tac gag cgg aac aag ggc aag        336
Ile Cys Arg Ala Val Leu Pro Gln Phe Tyr Glu Arg Asn Lys Gly Lys
            100                 105                 110 atc gtt gtc tac gga agt gcc gca gcg atg cgg tac cag gaa ggt gcg        384
Ile Val Val Tyr Gly Ser Ala Ala Ala Met Arg Tyr Gln Glu Gly Ala
        115                 120                 125 ctg gcc tac agc acg gcg cgt ttc gct cag cgc ggg tac gtc acc gcc        432
Leu Ala Tyr Ser Thr Ala Arg Phe Ala Gln Arg Gly Tyr Val Thr Ala
    130                 135                 140 ctc ggt ccc gag gca gcg agg cac aac gtc aac gtg aac ttc atc gcc        480
```

```
                    Leu Gly Pro Glu Ala Ala Arg His Asn Val Asn Val Asn Phe Ile Ala
                    145                 150                 155                 160 cag cac tgg acc caa aac aag gag tac ttc tgg ccc gag cgc atc gcc         528
Gln His Trp Thr Gln Asn Lys Glu Tyr Phe Trp Pro Glu Arg Ile Ala
                165                 170                 175 acc gac gag ttc aag gag gat atg gcg cgc cga gtt ccc ctg ggt cgg         576
Thr Asp Glu Phe Lys Glu Asp Met Ala Arg Arg Val Pro Leu Gly Arg
            180                 185                 190 ctc gcg act gcc cga gag tcc gcg ctc gcg ttg ttc ctg gcc tcg             624
Leu Ala Thr Ala Arg Glu Ser Ala Leu Leu Ala Leu Phe Leu Ala Ser
        195                 200                 205 gac gag agt gac ttc atc gtc ggc aag tcg atc gag ttc gac ggc ggc         672
Asp Glu Ser Asp Phe Ile Val Gly Lys Ser Ile Glu Phe Asp Gly Gly
    210                 215                 220 tgg gcc acc tga                                                         684
Trp Ala Thr
225

<210> SEQ ID NO 55
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 55 atg gct aac gga aga ctg gca ggc aag cgg gtc cta ctc acg aac gcc         48
Met Ala Asn Gly Arg Leu Ala Gly Lys Arg Val Leu Leu Thr Asn Ala
1               5                   10                  15 gat gcc tac atg ggt gag gcc acg gtc cag gtg ttc gag gag gag ggc         96
Asp Ala Tyr Met Gly Glu Ala Thr Val Gln Val Phe Glu Glu Glu Gly
            20                  25                  30 gca gag gtc atc gct gac cac acc gac ttg acg aag gtc ggc gcg gcg         144
Ala Glu Val Ile Ala Asp His Thr Asp Leu Thr Lys Val Gly Ala Ala
        35                  40                  45 gag gag gtc gtc gag agg gct ggg cac atc gat gtc ctg gtg gcc aac         192
Glu Glu Val Val Glu Arg Ala Gly His Ile Asp Val Leu Val Ala Asn
    50                  55                  60 ttc gcg gtc gac gcc cac ttc ggg gtg acc gtg ctg gag acc gac gag         240
Phe Ala Val Asp Ala His Phe Gly Val Thr Val Leu Glu Thr Asp Glu
65                  70                  75                  80 gag ctg tgg cag acg gcc tac gag acc atc gtg cac ccg ctg cat cgg         288
Glu Leu Trp Gln Thr Ala Tyr Glu Thr Ile Val His Pro Leu His Arg
                85                  90                  95 atc tgc cgt gcg gtg ctc ccg cag ttc tac gag cgg aac aag ggc aag         336
Ile Cys Arg Ala Val Leu Pro Gln Phe Tyr Glu Arg Asn Lys Gly Lys
            100                 105                 110 atc gtt gtc tac gga agt gcc gca gcg atg cgg tac cag gaa ggt gcg         384
Ile Val Val Tyr Gly Ser Ala Ala Ala Met Arg Tyr Gln Glu Gly Ala
        115                 120                 125 ctg gcc tac agc acg gcg cgt ttc gct cag cgc ggg tac gtc acc gcc         432
Leu Ala Tyr Ser Thr Ala Arg Phe Ala Gln Arg Gly Tyr Val Thr Ala
    130                 135                 140 ctc ggt ccc gag gca gcg agg cac aac gtc aac gtg aac ttc atc gcc         480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc         528
Gln His Trp Thr Gln Asn Lys Glu Tyr Phe Trp Pro Glu Arg Ile Ala
                165                 170                 175
```

```
acc gac gag ttc aag gag gat atg gcg cgc cga gtt ccc ctg ggt cgg      576
Thr Asp Glu Phe Lys Glu Asp Met Ala Arg Arg Val Pro Leu Gly Arg
            180                 185                 190 ctc gcg act gcc cga gag act gcg ctg ctc gcg ttg ttc ctg gcc tcg      624
Leu Ala Thr Ala Arg Glu Thr Ala Leu Leu Ala Leu Phe Leu Ala Ser
        195                 200                 205 gac gag agt gac ttc atc gtc ggc aag tcg atc gag ttc gac ggc ggc      672
Asp Glu Ser Asp Phe Ile Val Gly Lys Ser Ile Glu Phe Asp Gly Gly
    210                 215                 220 tgg gcc acc tga                                                      684
Trp Ala Thr
225

<210> SEQ ID NO 56
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 56 atg gct aac gga aga ctg gca ggc aag cgg gtc cta ctc acg aac gcc       48
Met Ala Asn Gly Arg Leu Ala Gly Lys Arg Val Leu Leu Thr Asn Ala
1               5                   10                  15 gat gcc tac atg ggt gag gcc acg gtc cag gtg ttc gag gag gag ggc       96
Asp Ala Tyr Met Gly Glu Ala Thr Val Gln Val Phe Glu Glu Glu Gly
            20                  25                  30 gca gag gtc atc gct gac cac acc gac ttg acg aag gtc ggc gcg gcg      144
Ala Glu Val Ile Ala Asp His Thr Asp Leu Thr Lys Val Gly Ala Ala
        35                  40                  45 gag gag gtc gtc gag agg gct ggg cac atc gat gtc ctg gtg gcc aac      192
Glu Glu Val Val Glu Arg Ala Gly His Ile Asp Val Leu Val Ala Asn
    50                  55                  60 ttc gcg gtc gac gcc cac ttc ggg gtg acc gtg ctg gag acc gac gag      240
Phe Ala Val Asp Ala His Phe Gly Val Thr Val Leu Glu Thr Asp Glu
65                  70                  75                  80 gag ctg tgg cag acg gcc tac gag acc atc gtg cac ccg ctg cat cgg      288
Glu Leu Trp Gln Thr Ala Tyr Glu Thr Ile Val His Pro Leu His Arg
                85                  90                  95 atc tgc cgt gcg gtg ctc ccg cag ttc tac gag cgg aac aag ggc aag      336
Ile Cys Arg Ala Val Leu Pro Gln Phe Tyr Glu Arg Asn Lys Gly Lys
            100                 105                 110 atc gtt gtc tac gga agt gcc gca gcg atg cgg tac cag gaa ggt gcg      384
Ile Val Val Tyr Gly Ser Ala Ala Ala Met Arg Tyr Gln Glu Gly Ala
        115                 120                 125 ctg gcc tac agc acg gcg cgt ttc gct cag cgc ggg tac gtc acc gcc      432
Leu Ala Tyr Ser Thr Ala Arg Phe Ala Gln Arg Gly Tyr Val Thr Ala
    130                 135                 140 ctc ggt ccc gag gca gcg agg cac aac gtc aac gtg aac ttc atc gcc      480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc      528
Gln His Trp Thr Gln Asn Lys Glu Tyr Phe Trp Pro Glu Arg Ile Ala
                165                 170                 175 acc gac gag ttc aag gag gat atg gcg cgc cga gtt ccc ctg ggt cgg      576
Thr Asp Glu Phe Lys Glu Asp Met Ala Arg Arg Val Pro Leu Gly Arg
            180                 185                 190 ctc gcg act gcc cga gag tat gcg ctg ctc gcg ttg ttc ctg gcc tcg      624
Leu Ala Thr Ala Arg Glu Tyr Ala Leu Leu Ala Leu Phe Leu Ala Ser
        195                 200                 205
```

```
gac gag agt gac ttc atc gtc ggc aag tcg atc gag ttc gac ggc ggc      672
Asp Glu Ser Asp Phe Ile Val Gly Lys Ser Ile Glu Phe Asp Gly Gly
    210                 215                 220 tgg gcc acc tga                                                      684
Trp Ala Thr
225

<210> SEQ ID NO 57
<211> LENGTH: 28
<212> TYPE: DNA
<213> ORGANISM: Artificial Sequence
<220> FEATURE:
<223> OTHER INFORMATION: Synthetic DNA

<400> SEQUENCE: 57
ggccatggct aacggaagac tggcaggc                                       28

<210> SEQ ID NO 58
<211> LENGTH: 33
<212> TYPE: DNA
<213> ORGANISM: Artificial Sequence
<220> FEATURE:
<223> OTHER INFORMATION: Synthetic DNA

<400> SEQUENCE: 58
gatcatgaaa aacggaagac tggcaggcaa gcg                                 33

<210> SEQ ID NO 59
<211> LENGTH: 33
<212> TYPE: DNA
<213> ORGANISM: Artificial Sequence
<220> FEATURE:
<223> OTHER INFORMATION: Synthetic DNA

<400> SEQUENCE: 59
gatcatgaac aacggaagac tggcaggcaa gcg                                 33

<210> SEQ ID NO 60
<211> LENGTH: 32
<212> TYPE: DNA
<213> ORGANISM: Artificial Sequence
<220> FEATURE:
<223> OTHER INFORMATION: Synthetic DNA

<400> SEQUENCE: 60
cgcctgcagg ctacaacgac gacgagcgcc tg                                  32

<210> SEQ ID NO 61
<211> LENGTH: 25
<212> TYPE: DNA
<213> ORGANISM: Artificial Sequence
<220> FEATURE:
<223> OTHER INFORMATION: Synthetic DNA

<400> SEQUENCE: 61
ggctgaaaat cttctctcat ccgcc                                          25

<210> SEQ ID NO 62
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (15)..(17)
<223> OTHER INFORMATION: n is a, c, g, or t
```

```
<400> SEQUENCE: 62
cgctggccta cagcnnngcg cgtttcgct                                              29

<210> SEQ ID NO 63
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (13)..(15)
<223> OTHER INFORMATION: n is a, c, g, or t

<400> SEQUENCE: 63
agcgaaacgc gcnnngctgt aggccagcg                                              29

<210> SEQ ID NO 64
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (14)..(16)
<223> OTHER INFORMATION: n is a, c, g, or t

<400> SEQUENCE: 64
cagcacggcg cgtnnngctc agcgcgggt                                              29

<210> SEQ ID NO 65
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (14)..(16)
<223> OTHER INFORMATION: n is a, c, g, or t

<400> SEQUENCE: 65
acccgcgctg agcnnnacgc gccgtgctg                                              29

<210> SEQ ID NO 66
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (15)..(17)
<223> OTHER INFORMATION: n is a, c, g, or t

<400> SEQUENCE: 66
cgactgcccg agagnnngcg ctgctcgcg                                              29

<210> SEQ ID NO 67
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (13)..(15)
<223> OTHER INFORMATION: n is a, c, g, or t
```

```
<400> SEQUENCE: 67
cgcgagcagc gcnnnctctc gggcagtcg                                              29

<210> SEQ ID NO 68
<211> LENGTH: 29
<212> TYPE: DNA
<213> ORGANISM: Artificial Sequence
<220> FEATURE:
<223> OTHER INFORMATION: Synthetic DNA

<400> SEQUENCE: 68
cgctggccta cagcgcggcg cgtttcgct                                              29

<210> SEQ ID NO 69
<211> LENGTH: 29
<212> TYPE: DNA
<213> ORGANISM: Artificial Sequence
<220> FEATURE:
<223> OTHER INFORMATION: Synthetic DNA

<400> SEQUENCE: 69
agcgaaacgc gccgcgctgt aggccagcg                                              29

<210> SEQ ID NO 70
<211> LENGTH: 29
<212> TYPE: DNA
<213> ORGANISM: Artificial Sequence
<220> FEATURE:
<223> OTHER INFORMATION: Synthetic DNA

<400> SEQUENCE: 70
cagcacggcg cgttccgctc agcgcgggt                                              29

<210> SEQ ID NO 71
<211> LENGTH: 29
<212> TYPE: DNA
<213> ORGANISM: Artificial Sequence
<220> FEATURE:
<223> OTHER INFORMATION: Synthetic DNA

<400> SEQUENCE: 71
acccgcgctg agcggaacgc gccgtgctg                                              29

<210> SEQ ID NO 72
<211> LENGTH: 29
<212> TYPE: DNA
<213> ORGANISM: Artificial Sequence
<220> FEATURE:
<223> OTHER INFORMATION: Synthetic DNA

<400> SEQUENCE: 72
cgactgcccg agagcacgcg ctgctcgcg                                              29

<210> SEQ ID NO 73
<211> LENGTH: 29
<212> TYPE: DNA
<213> ORGANISM: Artificial Sequence
<220> FEATURE:
<223> OTHER INFORMATION: Synthetic DNA

<400> SEQUENCE: 73
cgcgagcagc gcgtgctctc gggcagtcg                                              29

<210> SEQ ID NO 74
<211> LENGTH: 19
```

```
<212> TYPE: PRT
<213> ORGANISM: Corynebacterium sp.
<220> FEATURE:
<221> NAME/KEY: misc_feature
<222> LOCATION: (2)..(13)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 74

Ser Xaa Xaa Xaa Xaa Xaa Xaa Xaa Xaa Xaa Xaa Xaa Tyr Xaa Xaa
1               5                   10                  15

Ala Arg Xaa

<210> SEQ ID NO 75
<211> LENGTH: 10
<212> TYPE: PRT
<213> ORGANISM: Corynebacterium sp.
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 75

Leu Xaa Arg Leu Xaa Xaa Xaa Xaa Glu Xaa
1               5                   10

<210> SEQ ID NO 76
<211> LENGTH: 235
<212> TYPE: PRT
<213> ORGANISM: Artificial Sequence
<220> FEATURE:
<223> OTHER INFORMATION: Variant peptide

<400> SEQUENCE: 76

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Glu Gly Ala Glu Val Ile Ala Asp His Thr
        35                  40                  45

Asp Leu Thr Lys Val Gly Ala Ala Glu Glu Val Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
            100                 105                 110

Phe Tyr Glu Arg Asn Lys Gly Lys Ile Val Val Tyr Gly Ser Ala Ala
        115                 120                 125

Ala Met Arg Tyr Gln Glu Gly Ala Leu Ala Tyr Ser Thr Ala Arg Trp
```

```
                130             135             140
Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
                180                 185                 190

Ala Arg Arg Val Pro Leu Gly Arg Leu Ala Thr Ala Arg Glu Asp Ala
                195                 200                 205

Leu Leu Ala Leu Phe Leu Ala Ser Asp Glu Ser Asp Phe Ile Val Gly
                210                 215                 220

Lys Ser Ile Glu Phe Asp Gly Gly Trp Ala Thr
225                 230                 235

<210> SEQ ID NO 77
<211> LENGTH: 235
<212> TYPE: PRT
<213> ORGANISM: Artificial Sequence
<220> FEATURE:
<223> OTHER INFORMATION: Variant peptide

<400> SEQUENCE: 77

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
                20                  25                  30

Val Gln Val Phe Glu Glu Glu Gly Ala Glu Val Ile Ala Asp His Thr
                35                  40                  45

Asp Leu Thr Lys Val Gly Ala Ala Glu Glu Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
                100                 105                 110

Phe Tyr Glu Arg Asn Lys Gly Lys Ile Val Val Tyr Gly Ser Ala Ala
                115                 120                 125

Ala Met Arg Tyr Gln Glu Gly Ala Leu Ala Tyr Ser Thr Ala Arg Phe
                130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
                180                 185                 190

Ala Arg Arg Val Pro Leu Gly Arg Leu Ala Thr Ala Arg Glu Leu Ala
                195                 200                 205

Leu Leu Ala Leu Phe Leu Ala Ser Asp Glu Ser Asp Phe Ile Val Gly
                210                 215                 220

Lys Ser Ile Glu Phe Asp Gly Gly Trp Ala Thr
225                 230                 235

<210> SEQ ID NO 78
<211> LENGTH: 235
<212> TYPE: PRT
<213> ORGANISM: Artificial Sequence
```

-continued

```
<220> FEATURE:
<223> OTHER INFORMATION: Variant peptide

<400> SEQUENCE: 78

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Glu Gly Ala Glu Val Ile Ala Asp His Thr
        35                  40                  45

Asp Leu Thr Lys Val Gly Ala Ala Glu Glu Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
            100                 105                 110

Phe Tyr Glu Arg Asn Lys Gly Lys Ile Val Val Tyr Gly Ser Ala Ala
        115                 120                 125

Ala Met Arg Tyr Gln Glu Gly Ala Leu Ala Tyr Ser Thr Ala Arg Phe
    130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
            180                 185                 190

Ala Arg Arg Val Pro Leu Gly Arg Leu Ala Thr Ala Arg Glu Met Ala
        195                 200                 205

Leu Leu Ala Leu Phe Leu Ala Ser Asp Glu Ser Asp Phe Ile Val Gly
    210                 215                 220

Lys Ser Ile Glu Phe Asp Gly Gly Trp Ala Thr
225                 230                 235

<210> SEQ ID NO 79
<211> LENGTH: 235
<212> TYPE: PRT
<213> ORGANISM: Artificial Sequence
<220> FEATURE:
<223> OTHER INFORMATION: Variant peptide

<400> SEQUENCE: 79

Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Glu Gly Ala Glu Val Ile Ala Asp His Thr
        35                  40                  45

Asp Leu Thr Lys Val Gly Ala Ala Glu Glu Val Glu Arg Ala Gly
    50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
            100                 105                 110
```

```
Phe Tyr Glu Arg Asn Lys Gly Lys Ile Val Val Tyr Gly Ser Ala Ala
            115                 120                 125

Ala Met Arg Tyr Gln Glu Gly Ala Leu Ala Tyr Ser Thr Ala Arg Phe
    130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
            180                 185                 190

Ala Arg Arg Val Pro Leu Gly Arg Leu Ala Thr Ala Arg Glu Ile Ala
        195                 200                 205

Leu Leu Ala Leu Phe Leu Ala Ser Asp Glu Ser Asp Phe Ile Val Gly
    210                 215                 220

Lys Ser Ile Glu Phe Asp Gly Gly Trp Ala Thr
225                 230                 235

<210> SEQ ID NO 80
<211> LENGTH: 227
<212> TYPE: PRT
<213> ORGANISM: Artificial Sequence
<220> FEATURE:
<223> OTHER INFORMATION: Variant peptide

<400> SEQUENCE: 80

Met Ala Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Glu Gly
            20                  25                  30

Ala Glu Val Ile Ala Asp His Thr Asp Leu Thr Lys Val Gly Ala Ala
        35                  40                  45

Glu Glu Val Val Glu Arg Ala Gly His Ile Asp Val Leu Val Ala Asn
    50                  55                  60

Phe Ala Val Asp Ala His Phe Gly Val Thr Val Leu Glu Thr Asp Glu
65                  70                  75                  80

Glu Leu Trp Gln Thr Ala Tyr Glu Thr Ile Val His Pro Leu His Arg
                85                  90                  95

Ile Cys Arg Ala Val Leu Pro Gln Phe Tyr Glu Arg Asn Lys Gly Lys
            100                 105                 110

Ile Val Val Tyr Gly Ser Ala Ala Ala Met Arg Tyr Gln Glu Gly Ala
        115                 120                 125

Leu Ala Tyr Ser Thr Ala Arg Trp Ala Gln Arg Gly Tyr Val Thr Ala
    130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
            180                 185                 190

Leu Ala Thr Ala Arg Glu Asp Ala Leu Leu Ala Leu Phe Leu Ala Ser
        195                 200                 205

Asp Glu Ser Asp Phe Ile Val Gly Lys Ser Ile Glu Phe Asp Gly Gly
    210                 215                 220

Trp Ala Thr
225
```

-continued

```
<210> SEQ ID NO 81
<211> LENGTH: 227
<212> TYPE: PRT
<213> ORGANISM: Artificial Sequence
<220> FEATURE:
<223> OTHER INFORMATION: Variant peptide

<400> SEQUENCE: 81

Met Ala Asn Gly Arg Leu Ala Gly Lys Arg Val Leu Leu Thr Asn Ala
 1               5                  10                  15

Asp Ala Tyr Met Gly Glu Ala Thr Val Gln Val Phe Glu Glu Glu Gly
                20                  25                  30

Ala Glu Val Ile Ala Asp His Thr Asp Leu Thr Lys Val Gly Ala Ala
            35                  40                  45

Glu Glu Val Val Glu Arg Ala Gly His Ile Asp Val Leu Val Ala Asn
        50                  55                  60

Phe Ala Val Asp Ala His Phe Gly Val Thr Val Leu Glu Thr Asp Glu
65                  70                  75                  80

Glu Leu Trp Gln Thr Ala Tyr Glu Thr Ile Val His Pro Leu His Arg
                85                  90                  95

Ile Cys Arg Ala Val Leu Pro Gln Phe Tyr Glu Arg Asn Lys Gly Lys
            100                 105                 110

Ile Val Val Tyr Gly Ser Ala Ala Ala Met Arg Tyr Gln Glu Gly Ala
        115                 120                 125

Leu Ala Tyr Ser Thr Ala Arg Phe Ala Gln Arg Gly Tyr Val Thr Ala
    130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
            180                 185                 190

Leu Ala Thr Ala Arg Glu Leu Ala Leu Leu Ala Leu Phe Leu Ala Ser
        195                 200                 205

Asp Glu Ser Asp Phe Ile Val Gly Lys Ser Ile Glu Phe Asp Gly Gly
    210                 215                 220

Trp Ala Thr
225

<210> SEQ ID NO 82
<211> LENGTH: 227
<212> TYPE: PRT
<213> ORGANISM: Artificial Sequence
<220> FEATURE:
<223> OTHER INFORMATION: Variant peptide

<400> SEQUENCE: 82

Met Ala Asn Gly Arg Leu Ala Gly Lys Arg Val Leu Leu Thr Asn Ala
 1               5                  10                  15

Asp Ala Tyr Met Gly Glu Ala Thr Val Gln Val Phe Glu Glu Glu Gly
                20                  25                  30

Ala Glu Val Ile Ala Asp His Thr Asp Leu Thr Lys Val Gly Ala Ala
            35                  40                  45

Glu Glu Val Val Glu Arg Ala Gly His Ile Asp Val Leu Val Ala Asn
        50                  55                  60

Phe Ala Val Asp Ala His Phe Gly Val Thr Val Leu Glu Thr Asp Glu
65                  70                  75                  80
```

Glu Leu Trp Gln Thr Ala Tyr Glu Thr Ile Val His Pro Leu His Arg
            85                  90                  95

Ile Cys Arg Ala Val Leu Pro Gln Phe Tyr Glu Arg Asn Lys Gly Lys
                100                 105                 110

Ile Val Val Tyr Gly Ser Ala Ala Ala Met Arg Tyr Gln Glu Gly Ala
            115                 120                 125

Leu Ala Tyr Ser Thr Ala Arg Phe Ala Gln Arg Gly Tyr Val Thr Ala
        130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
            180                 185                 190

Leu Ala Thr Ala Arg Glu Met Ala Leu Leu Ala Leu Phe Leu Ala Ser
            195                 200                 205

Asp Glu Ser Asp Phe Ile Val Gly Lys Ser Ile Glu Phe Asp Gly Gly
        210                 215                 220

Trp Ala Thr
225

<210> SEQ ID NO 83
<211> LENGTH: 227
<212> TYPE: PRT
<213> ORGANISM: Artificial Sequence
<220> FEATURE:
<223> OTHER INFORMATION: Variant peptide

<400> SEQUENCE: 83

Met Ala Asn Gly Arg Leu Ala Gly Lys Arg Val Leu Leu Thr Asn Ala
1               5                   10                  15

Asp Ala Tyr Met Gly Glu Ala Thr Val Gln Val Phe Glu Glu Glu Gly
            20                  25                  30

Ala Glu Val Ile Ala Asp His Thr Asp Leu Thr Lys Val Gly Ala Ala
        35                  40                  45

Glu Glu Val Val Glu Arg Ala Gly His Ile Asp Val Leu Val Ala Asn
    50                  55                  60

Phe Ala Val Asp Ala His Phe Gly Val Thr Val Leu Glu Thr Asp Glu
65                  70                  75                  80

Glu Leu Trp Gln Thr Ala Tyr Glu Thr Ile Val His Pro Leu His Arg
            85                  90                  95

Ile Cys Arg Ala Val Leu Pro Gln Phe Tyr Glu Arg Asn Lys Gly Lys
                100                 105                 110

Ile Val Val Tyr Gly Ser Ala Ala Ala Met Arg Tyr Gln Glu Gly Ala
            115                 120                 125

Leu Ala Tyr Ser Thr Ala Arg Phe Ala Gln Arg Gly Tyr Val Thr Ala
        130                 135                 140

Leu Gly Pro Glu Ala Ala Arg His Asn Val Asn Val Asn Phe Ile Ala
145                 150                 155                 160

Gln His Trp Thr Gln Asn Lys Glu Tyr Phe Trp Pro Glu Arg Ile Ala
                165                 170                 175

Thr Asp Glu Phe Lys Glu Asp Met Ala Arg Arg Val Pro Leu Gly Arg
            180                 185                 190

Leu Ala Thr Ala Arg Glu Ile Ala Leu Leu Ala Leu Phe Leu Ala Ser
            195                 200                 205

Asp Glu Ser Asp Phe Ile Val Gly Lys Ser Ile Glu Phe Asp Gly Gly

Trp Ala Thr
225

<210> SEQ ID NO 84
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 84

```
atg gct aac gga agg aaa agg gaa atg gct aac gga aga ctg gca ggc      48
Met Ala Asn Gly Arg Lys Arg Glu Met Ala Asn Gly Arg Leu Ala Gly
1               5                   10                  15 aag cgg gtc cta ctc acg aac gcc gat gcc tac atg ggt gag gcc acg      96
Lys Arg Val Leu Leu Thr Asn Ala Asp Ala Tyr Met Gly Glu Ala Thr
            20                  25                  30 gtc cag gtg ttc gag gag gag ggc gca gag gtc atc gct gac cac acc     144
Val Gln Val Phe Glu Glu Glu Gly Ala Glu Val Ile Ala Asp His Thr
        35                  40                  45 gac ttg acg aag gtc ggc gcg gcg gag gag gtc gtc gag agg gct ggg     192
Asp Leu Thr Lys Val Gly Ala Ala Glu Glu Val Val Glu Arg Ala Gly
    50                  55                  60 cac atc gat gtc ctg gtg gcc aac ttc gcg gtc gac gcc cac ttc ggg     240
His Ile Asp Val Leu Val Ala Asn Phe Ala Val Asp Ala His Phe Gly
65                  70                  75                  80 gtg acc gtg ctg gag acc gac gag gag ctg tgg cag acg gcc tac gag     288
Val Thr Val Leu Glu Thr Asp Glu Glu Leu Trp Gln Thr Ala Tyr Glu
                85                  90                  95 acc atc gtg cac ccg ctg cat cgg atc tgc cgt gcg gtg ctc ccg cag     336
Thr Ile Val His Pro Leu His Arg Ile Cys Arg Ala Val Leu Pro Gln
            100                 105                 110 ttc tac gag cgg aac aag ggc aag atc gtt gtc tac gga agt gcc gca     384
Phe Tyr Glu Arg Asn Lys Gly Lys Ile Val Val Tyr Gly Ser Ala Ala
        115                 120                 125 gcg atg cgg tac cag gaa ggt gcg ctg gcc tac agc acg gcg cgt tgg     432
Ala Met Arg Tyr Gln Glu Gly Ala Leu Ala Tyr Ser Thr Ala Arg Trp
    130                 135                 140 gct cag cgc ggg tac gtc acc gcc ctc ggt ccc gag gca gcg agg cac     480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag     528
Asn Val Asn Val Asn Phe Ile Ala Gln His Trp Thr Gln Asn Lys Glu
                165                 170                 175 tac ttc tgg ccc gag cgc atc gcc acc gac gag ttc aag gag gat atg     576
Tyr Phe Trp Pro Glu Arg Ile Ala Thr Asp Glu Phe Lys Glu Asp Met
            180                 185                 190 gcg cgc cga gtt ccc ctg ggt cgg ctc gcg act gcc cga gag gac gcg     624
Ala Arg Arg Val Pro Leu Gly Arg Leu Ala Thr Ala Arg Glu Asp Ala
        195                 200                 205 ctg ctc gcg ttg ttc ctg gcc tcg gac gag agt gac ttc atc gtc ggc     672
Leu Leu Ala Leu Phe Leu Ala Ser Asp Glu Ser Asp Phe Ile Val Gly
    210                 215                 220 aag tcg atc gag ttc gac ggc ggc tgg gcc acc tga                     708
Lys Ser Ile Glu Phe Asp Gly Gly Trp Ala Thr
225                 230                 235
```

<210> SEQ ID NO 85

<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 85

```
atg gct aac gga agg aaa agg gaa atg gct aac gga aga ctg gca ggc      48
Met Ala Asn Gly Arg Lys Arg Glu Met Ala Asn Gly Arg Leu Ala Gly
1               5                   10                  15 aag cgg gtc cta ctc acg aac gcc gat gcc tac atg ggt gag gcc acg      96
Lys Arg Val Leu Leu Thr Asn Ala Asp Ala Tyr Met Gly Glu Ala Thr
            20                  25                  30 gtc cag gtg ttc gag gag gag ggc gca gag gtc atc gct gac cac acc     144
Val Gln Val Phe Glu Glu Glu Gly Ala Glu Val Ile Ala Asp His Thr
        35                  40                  45 gac ttg acg aag gtc ggc gcg gcg gag gag gtc gtc gag agg gct ggg     192
Asp Leu Thr Lys Val Gly Ala Ala Glu Glu Val Val Glu Arg Ala Gly
    50                  55                  60 cac atc gat gtc ctg gtg gcc aac ttc gcg gtc gac gcc cac ttc ggg     240
His Ile Asp Val Leu Val Ala Asn Phe Ala Val Asp Ala His Phe Gly
65                  70                  75                  80 gtg acc gtg ctg gag acc gac gag gag ctg tgg cag acg gcc tac gag     288
Val Thr Val Leu Glu Thr Asp Glu Glu Leu Trp Gln Thr Ala Tyr Glu
                85                  90                  95 acc atc gtg cac ccg ctg cat cgg atc tgc cgt gcg gtg ctc ccg cag     336
Thr Ile Val His Pro Leu His Arg Ile Cys Arg Ala Val Leu Pro Gln
            100                 105                 110 ttc tac gag cgg aac aag ggc aag atc gtt gtc tac gga agt gcc gca     384
Phe Tyr Glu Arg Asn Lys Gly Lys Ile Val Val Tyr Gly Ser Ala Ala
        115                 120                 125 gcg atg cgg tac cag gaa ggt gcg ctg gcc tac agc acg gcg cgt ttc     432
Ala Met Arg Tyr Gln Glu Gly Ala Leu Ala Tyr Ser Thr Ala Arg Phe
    130                 135                 140 gct cag cgc ggg tac gtc acc gcc ctc ggt ccc gag gca gcg agg cac     480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag     528
Asn Val Asn Val Asn Phe Ile Ala Gln His Trp Thr Gln Asn Lys Glu
                165                 170                 175 tac ttc tgg ccc gag cgc atc gcc acc gac gag ttc aag gag gat atg     576
Tyr Phe Trp Pro Glu Arg Ile Ala Thr Asp Glu Phe Lys Glu Asp Met
            180                 185                 190 gcg cgc cga gtt ccc ctg ggt cgg ctc gcg act gcc cga gag ctg gcg     624
Ala Arg Arg Val Pro Leu Gly Arg Leu Ala Thr Ala Arg Glu Leu Ala
        195                 200                 205 ctg ctc gcg ttg ttc ctg gcc tcg gac gag agt gac ttc atc gtc ggc     672
Leu Leu Ala Leu Phe Leu Ala Ser Asp Glu Ser Asp Phe Ile Val Gly
    210                 215                 220 aag tcg atc gag ttc gac ggc ggc tgg gcc acc tga                     708
Lys Ser Ile Glu Phe Asp Gly Gly Trp Ala Thr
225                 230                 235
```

<210> SEQ ID NO 86
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS

<222> LOCATION: (1)..(708)

<400> SEQUENCE: 86

```
atg gct aac gga agg aaa agg gaa atg gct aac gga aga ctg gca ggc      48
Met Ala Asn Gly Arg Lys Arg Glu Met Ala Asn Gly Arg Leu Ala Gly
1               5                   10                  15 aag cgg gtc cta ctc acg aac gcc gat gcc tac atg ggt gag gcc acg      96
Lys Arg Val Leu Leu Thr Asn Ala Asp Ala Tyr Met Gly Glu Ala Thr
            20                  25                  30 gtc cag gtg ttc gag gag gag ggc gca gag gtc atc gct gac cac acc     144
Val Gln Val Phe Glu Glu Glu Gly Ala Glu Val Ile Ala Asp His Thr
        35                  40                  45 gac ttg acg aag gtc ggc gcg gcg gag gag gtc gtc gag agg gct ggg     192
Asp Leu Thr Lys Val Gly Ala Ala Glu Glu Val Val Glu Arg Ala Gly
    50                  55                  60 cac atc gat gtc ctg gtg gcc aac ttc gcg gtc gac gcc cac ttc ggg     240
His Ile Asp Val Leu Val Ala Asn Phe Ala Val Asp Ala His Phe Gly
65                  70                  75                  80 gtg acc gtg ctg gag acc gac gag gag ctg tgg cag acg gcc tac gag     288
Val Thr Val Leu Glu Thr Asp Glu Glu Leu Trp Gln Thr Ala Tyr Glu
                85                  90                  95 acc atc gtg cac ccg ctg cat cgg atc tgc cgt gcg gtg ctc ccg cag     336
Thr Ile Val His Pro Leu His Arg Ile Cys Arg Ala Val Leu Pro Gln
            100                 105                 110 ttc tac gag cgg aac aag ggc aag atc gtt gtc tac gga agt gcc gca     384
Phe Tyr Glu Arg Asn Lys Gly Lys Ile Val Val Tyr Gly Ser Ala Ala
        115                 120                 125 gcg atg cgg tac cag gaa ggt gcg ctg gcc tac agc acg gcg cgt ttc     432
Ala Met Arg Tyr Gln Glu Gly Ala Leu Ala Tyr Ser Thr Ala Arg Phe
    130                 135                 140 gct cag cgc ggg tac gtc acc gcc ctc ggt ccc gag gca gcg agg cac     480
Ala Gln Arg Gly Tyr Val Thr Ala Leu Gly Pro Glu Ala Ala Arg His
145                 150                 155                 160 aac gtc aac gtg aac ttc atc gcc cag cac tgg acc caa aac aag gag     528
Asn Val Asn Val Asn Phe Ile Ala Gln His Trp Thr Gln Asn Lys Glu
                165                 170                 175 tac ttc tgg ccc gag cgc atc gcc acc gac gag ttc aag gag gat atg     576
Tyr Phe Trp Pro Glu Arg Ile Ala Thr Asp Glu Phe Lys Glu Asp Met
            180                 185                 190 gcg cgc cga gtt ccc ctg ggt cgg ctc gcg act gcc cga gag atg gcg     624
Ala Arg Arg Val Pro Leu Gly Arg Leu Ala Thr Ala Arg Glu Met Ala
        195                 200                 205 ctg ctc gcg ttg ttc ctg gcc tcg gac gag agt gac ttc atc gtc ggc     672
Leu Leu Ala Leu Phe Leu Ala Ser Asp Glu Ser Asp Phe Ile Val Gly
    210                 215                 220 aag tcg atc gag ttc gac ggc ggc tgg gcc acc tga                     708
Lys Ser Ile Glu Phe Asp Gly Gly Trp Ala Thr
225                 230                 235
```

<210> SEQ ID NO 87
<211> LENGTH: 708
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(708)

<400> SEQUENCE: 87

```
atg gct aac gga agg aaa agg gaa atg gct aac gga aga ctg gca ggc      48
Met Ala Asn Gly Arg Lys Arg Glu Met Ala Asn Gly Arg Leu Ala Gly
1               5                   10                  15
```

| | | |
|---|---|---|
| aag cgg gtc cta ctc acg aac gcc gat gcc tac atg ggt gag gcc acg<br>Lys Arg Val Leu Leu Thr Asn Ala Asp Ala Tyr Met Gly Glu Ala Thr<br>20 25 30 | | 96 |
| gtc cag gtg ttc gag gag gag ggc gca gag gtc atc gct gac cac acc<br>Val Gln Val Phe Glu Glu Glu Gly Ala Glu Val Ile Ala Asp His Thr<br>35 40 45 | | 144 |
| gac ttg acg aag gtc ggc gcg gcg gag gag gtc gtc gag agg gct ggg<br>Asp Leu Thr Lys Val Gly Ala Ala Glu Glu Val Val Glu Arg Ala Gly<br>50 55 60 | | 192 |
| cac atc gat gtc ctg gtg gcc aac ttc gcg gtc gac gcc cac ttc ggg<br>His Ile Asp Val Leu Val Ala Asn Phe Ala Val Asp Ala His Phe Gly<br>65 70 75 80 | | 240 |
| gtg acc gtg ctg gag acc gac gag gag ctg tgg cag acg gcc tac gag<br>Val Thr Val Leu Glu Thr Asp Glu Glu Leu Trp Gln Thr Ala Tyr Glu<br>85 90 95 | | 288 |
| acc atc gtg cac ccg ctg cat cgg atc tgc cgt gcg gtg ctc ccg cag<br>Thr Ile Val His Pro Leu His Arg Ile Cys Arg Ala Val Leu Pro Gln<br>100 105 110 | | 336 |
| ttc tac gag cgg aac aag ggc aag atc gtt gtc tac gga agt gcc gca<br>Phe Tyr Glu Arg Asn Lys Gly Lys Ile Val Val Tyr Gly Ser Ala Ala<br>115 120 125 | | 384 |
| gcg atg cgg tac cag gaa ggt gcg ctg gcc tac agc acg gcg cgt ttc<br>Ala Met Arg Tyr Gln Glu Gly Ala Leu Ala Tyr Ser Thr Ala Arg Phe<br>130 135 140 | | 432 |
| gct cag cgc ggg tac gtc acc gcc ctc ggt ccc gag gca gcg agg cac<br>Ala Gln Arg Gly Tyr Val Thr Ala Leu Gly Pro Glu Ala Ala Arg His<br>145 150 155 160 | | 480 |
| aac gtc aac gtg aac ttc atc gcc cag cac tgg acc caa aac aag gag<br>Asn Val Asn Val Asn Phe Ile Ala Gln His Trp Thr Gln Asn Lys Glu<br>165 170 175 | | 528 |
| tac ttc tgg ccc gag cgc atc gcc acc gac gag ttc aag gag gat atg<br>Tyr Phe Trp Pro Glu Arg Ile Ala Thr Asp Glu Phe Lys Glu Asp Met<br>180 185 190 | | 576 |
| gcg cgc cga gtt ccc ctg ggt cgg ctc gcg act gcc cga gag atc gcg<br>Ala Arg Arg Val Pro Leu Gly Arg Leu Ala Thr Ala Arg Glu Ile Ala<br>195 200 205 | | 624 |
| ctg ctc gcg ttg ttc ctg gcc tcg gac gag agt gac ttc atc gtc ggc<br>Leu Leu Ala Leu Phe Leu Ala Ser Asp Glu Ser Asp Phe Ile Val Gly<br>210 215 220 | | 672 |
| aag tcg atc gag ttc gac ggc ggc tgg gcc acc tga<br>Lys Ser Ile Glu Phe Asp Gly Gly Trp Ala Thr<br>225 230 235 | | 708 |

```
<210> SEQ ID NO 88
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 88
```

| | | |
|---|---|---|
| atg gct aac gga aga ctg gca ggc aag cgg gtc cta ctc acg aac gcc<br>Met Ala Asn Gly Arg Leu Ala Gly Lys Arg Val Leu Leu Thr Asn Ala<br>1 5 10 15 | | 48 |
| gat gcc tac atg ggt gag gcc acg gtc cag gtg ttc gag gag gag ggc<br>Asp Ala Tyr Met Gly Glu Ala Thr Val Gln Val Phe Glu Glu Glu Gly<br>20 25 30 | | 96 |
| gca gag gtc atc gct gac cac acc gac ttg acg aag gtc ggc gcg gcg<br>Ala Glu Val Ile Ala Asp His Thr Asp Leu Thr Lys Val Gly Ala Ala | | 144 |

```
                35                  40                  45
gag gag gtc gtc gag agg gct ggg cac atc gat gtc ctg gtg gcc aac        192
Glu Glu Val Val Glu Arg Ala Gly His Ile Asp Val Leu Val Ala Asn
         50                  55                  60 ttc gcg gtc gac gcc cac ttc ggg gtg acc gtg ctg gag acc gac gag        240
Phe Ala Val Asp Ala His Phe Gly Val Thr Val Leu Glu Thr Asp Glu
65                  70                  75                  80 gag ctg tgg cag acg gcc tac gag acc atc gtg cac ccg ctg cat cgg        288
Glu Leu Trp Gln Thr Ala Tyr Glu Thr Ile Val His Pro Leu His Arg
                 85                  90                  95 atc tgc cgt gcg gtg ctc ccg cag ttc tac gag cgg aac aag ggc aag        336
Ile Cys Arg Ala Val Leu Pro Gln Phe Tyr Glu Arg Asn Lys Gly Lys
            100                 105                 110 atc gtt gtc tac gga agt gcc gca gcg atg cgg tac cag gaa ggt gcg        384
Ile Val Val Tyr Gly Ser Ala Ala Ala Met Arg Tyr Gln Glu Gly Ala
        115                 120                 125 ctg gcc tac agc acg gcg cgt tgg gct cag cgc ggg tac gtc acc gcc        432
Leu Ala Tyr Ser Thr Ala Arg Trp Ala Gln Arg Gly Tyr Val Thr Ala
130                 135                 140 ctc ggt ccc gag gca gcg agg cac aac gtc aac gtg aac ttc atc gcc        480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc        528
Gln His Trp Thr Gln Asn Lys Glu Tyr Phe Trp Pro Glu Arg Ile Ala
                165                 170                 175 acc gac gag ttc aag gag gat atg gcg cgc cga gtt ccc ctg ggt cgg        576
Thr Asp Glu Phe Lys Glu Asp Met Ala Arg Arg Val Pro Leu Gly Arg
            180                 185                 190 ctc gcg act gcc cga gag gac gcg ctc ctc gcg ttg ttc ctg gcc tcg        624
Leu Ala Thr Ala Arg Glu Asp Ala Leu Leu Ala Leu Phe Leu Ala Ser
        195                 200                 205 gac gag agt gac ttc atc gtc ggc aag tcg atc gag ttc gac ggc ggc        672
Asp Glu Ser Asp Phe Ile Val Gly Lys Ser Ile Glu Phe Asp Gly Gly
210                 215                 220 tgg gcc acc tga                                                        684
Trp Ala Thr
225

<210> SEQ ID NO 89
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 89 atg gct aac gga aga ctg gca ggc aag cgg gtc cta ctc acg aac gcc        48
Met Ala Asn Gly Arg Leu Ala Gly Lys Arg Val Leu Leu Thr Asn Ala
1               5                   10                  15 gat gcc tac atg ggt gag gcc acg gtc cag gtg ttc gag gag gag ggc        96
Asp Ala Tyr Met Gly Glu Ala Thr Val Gln Val Phe Glu Glu Glu Gly
                20                  25                  30 gca gag gtc atc gct gac cac acc gac ttg acg aag gtc ggc gcg gcg        144
Ala Glu Val Ile Ala Asp His Thr Asp Leu Thr Lys Val Gly Ala Ala
            35                  40                  45 gag gag gtc gtc gag agg gct ggg cac atc gat gtc ctg gtg gcc aac        192
Glu Glu Val Val Glu Arg Ala Gly His Ile Asp Val Leu Val Ala Asn
        50                  55                  60 ttc gcg gtc gac gcc cac ttc ggg gtg acc gtg ctg gag acc gac gag        240
```

-continued

| | | |
|---|---|---|
| Phe Ala Val Asp Ala His Phe Gly Val Thr Val Leu Glu Thr Asp Glu<br>65                              70                        75                       80 | | |
| gag ctg tgg cag acg gcc tac gag acc atc gtg cac ccg ctg cat cgg<br>Glu Leu Trp Gln Thr Ala Tyr Glu Thr Ile Val His Pro Leu His Arg<br>                        85                        90                       95 | 288 | |
| atc tgc cgt gcg gtg ctc ccg cag ttc tac gag cgg aac aag ggc aag<br>Ile Cys Arg Ala Val Leu Pro Gln Phe Tyr Glu Arg Asn Lys Gly Lys<br>                        100                     105                     110 | 336 | |
| atc gtt gtc tac gga agt gcc gca gcg atg cgg tac cag gaa ggt gcg<br>Ile Val Val Tyr Gly Ser Ala Ala Ala Met Arg Tyr Gln Glu Gly Ala<br>             115                     120                     125 | 384 | |
| ctg gcc tac agc acg gcg cgt ttc gct cag cgc ggg tac gtc acc gcc<br>Leu Ala Tyr Ser Thr Ala Arg Phe Ala Gln Arg Gly Tyr Val Thr Ala<br>130                           135                     140 | 432 | |
| ctc ggt ccc gag gca gcg agg cac aac gtc aac gtg aac ttc atc gcc<br>Leu Gly Pro Glu Ala Ala Arg His Asn Val Asn Val Asn Phe Ile Ala<br>145                           150                     155                     160 | 480 | |
| cag cac tgg acc caa aac aag gag tac ttc tgg ccc gag cgc atc gcc<br>Gln His Trp Thr Gln Asn Lys Glu Tyr Phe Trp Pro Glu Arg Ile Ala<br>                        165                     170                     175 | 528 | |
| acc gac gag ttc aag gag gat atg gcg cgc cga gtt ccc ctg ggt cgg<br>Thr Asp Glu Phe Lys Glu Asp Met Ala Arg Arg Val Pro Leu Gly Arg<br>             180                     185                     190 | 576 | |
| ctc gcg act gcc cga gag ctg gcg ctc ctc gcg ttg ttc ctg gcc tcg<br>Leu Ala Thr Ala Arg Glu Leu Ala Leu Leu Ala Leu Phe Leu Ala Ser<br>195                         200                     205 | 624 | |
| gac gag agt gac ttc atc gtc ggc aag tcg atc gag ttc gac ggc ggc<br>Asp Glu Ser Asp Phe Ile Val Gly Lys Ser Ile Glu Phe Asp Gly Gly<br>210                         215                     220 | 672 | |
| tgg gcc acc tga<br>Trp Ala Thr<br>225 | 684 | |

<210> SEQ ID NO 90
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 90

| | | |
|---|---|---|
| atg gct aac gga aga ctg gca ggc aag cgg gtc cta ctc acg aac gcc<br>Met Ala Asn Gly Arg Leu Ala Gly Lys Arg Val Leu Leu Thr Asn Ala<br>1                       5                        10                       15 | 48 | |
| gat gcc tac atg ggt gag gcc acg gtc cag gtg ttc gag gag gag ggc<br>Asp Ala Tyr Met Gly Glu Ala Thr Val Gln Val Phe Glu Glu Glu Gly<br>                     20                       25                     30 | 96 | |
| gca gag gtc atc gct gac cac acc gac ttg acg aag gtc ggc gcg gcg<br>Ala Glu Val Ile Ala Asp His Thr Asp Leu Thr Lys Val Gly Ala Ala<br>          35                     40                     45 | 144 | |
| gag gag gtc gtc gag agg gct ggg cac atc gat gtc ctg gtg gcc aac<br>Glu Glu Val Val Glu Arg Ala Gly His Ile Asp Val Leu Val Ala Asn<br>50                           55                     60 | 192 | |
| ttc gcg gtc gac gcc cac ttc ggg gtg acc gtg ctg gag acc gac gag<br>Phe Ala Val Asp Ala His Phe Gly Val Thr Val Leu Glu Thr Asp Glu<br>65                             70                       75                     80 | 240 | |
| gag ctg tgg cag acg gcc tac gag acc atc gtg cac ccg ctg cat cgg<br>Glu Leu Trp Gln Thr Ala Tyr Glu Thr Ile Val His Pro Leu His Arg<br>                        85                        90                       95 | 288 | |

```
atc tgc cgt gcg gtg ctc ccg cag ttc tac gag cgg aac aag ggc aag      336
Ile Cys Arg Ala Val Leu Pro Gln Phe Tyr Glu Arg Asn Lys Gly Lys
        100                 105                 110 atc gtt gtc tac gga agt gcc gca gcg atg cgg tac cag gaa ggt gcg      384
Ile Val Val Tyr Gly Ser Ala Ala Ala Met Arg Tyr Gln Glu Gly Ala
            115                 120                 125 ctg gcc tac agc acg gcg cgt ttc gct cag cgc ggg tac gtc acc gcc      432
Leu Ala Tyr Ser Thr Ala Arg Phe Ala Gln Arg Gly Tyr Val Thr Ala
130                 135                 140 ctc ggt ccc gag gca gcg agg cac aac gtc aac gtg aac ttc atc gcc      480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc      528
Gln His Trp Thr Gln Asn Lys Glu Tyr Phe Trp Pro Glu Arg Ile Ala
                165                 170                 175 acc gac gag ttc aag gag gat atg gcg cgc cga gtt ccc ctg ggt cgg      576
Thr Asp Glu Phe Lys Glu Asp Met Ala Arg Arg Val Pro Leu Gly Arg
            180                 185                 190 ctc gcg act gcc cga gag atg gcg ctc ctc gcg ttg ttc ctg gcc tcg      624
Leu Ala Thr Ala Arg Glu Met Ala Leu Leu Ala Leu Phe Leu Ala Ser
        195                 200                 205 gac gag agt gac ttc atc gtc ggc aag tcg atc gag ttc gac ggc ggc      672
Asp Glu Ser Asp Phe Ile Val Gly Lys Ser Ile Glu Phe Asp Gly Gly
    210                 215                 220 tgg gcc acc tga                                                      684
Trp Ala Thr
225

<210> SEQ ID NO 91
<211> LENGTH: 684
<212> TYPE: DNA
<213> ORGANISM: Artificial Sequence
<220> FEATURE:
<223> OTHER INFORMATION: Variant DNA
<220> FEATURE:
<221> NAME/KEY: CDS
<222> LOCATION: (1)..(684)

<400> SEQUENCE: 91 atg gct aac gga aga ctg gca ggc aag cgg gtc cta ctc acg aac gcc       48
Met Ala Asn Gly Arg Leu Ala Gly Lys Arg Val Leu Leu Thr Asn Ala
1               5                   10                  15 gat gcc tac atg ggt gag gcc acg gtc cag gtg ttc gag gag gag ggc       96
Asp Ala Tyr Met Gly Glu Ala Thr Val Gln Val Phe Glu Glu Glu Gly
            20                  25                  30 gca gag gtc atc gct gac cac acc gac ttg acg aag gtc ggc gcg gcg      144
Ala Glu Val Ile Ala Asp His Thr Asp Leu Thr Lys Val Gly Ala Ala
        35                  40                  45 gag gag gtc gtc gag agg gct ggg cac atc gat gtc ctg gtg gcc aac      192
Glu Glu Val Val Glu Arg Ala Gly His Ile Asp Val Leu Val Ala Asn
    50                  55                  60 ttc gcg gtc gac gcc cac ttc ggg gtg acc gtg ctg gag acc gac gag      240
Phe Ala Val Asp Ala His Phe Gly Val Thr Val Leu Glu Thr Asp Glu
65                  70                  75                  80 gag ctg tgg cag acg gcc tac gag acc atc gtg cac ccg ctg cat cgg      288
Glu Leu Trp Gln Thr Ala Tyr Glu Thr Ile Val His Pro Leu His Arg
                85                  90                  95 atc tgc cgt gcg gtg ctc ccg cag ttc tac gag cgg aac aag ggc aag      336
Ile Cys Arg Ala Val Leu Pro Gln Phe Tyr Glu Arg Asn Lys Gly Lys
        100                 105                 110 atc gtt gtc tac gga agt gcc gca gcg atg cgg tac cag gaa ggt gcg      384
Ile Val Val Tyr Gly Ser Ala Ala Ala Met Arg Tyr Gln Glu Gly Ala
            115                 120                 125
```

```
ctg gcc tac agc acg gcg cgt ttc gct cag cgc ggg tac gtc acc gcc    432
Leu Ala Tyr Ser Thr Ala Arg Phe Ala Gln Arg Gly Tyr Val Thr Ala
    130                 135                 140 ctc ggt ccc gag gca gcg agg cac aac gtc aac gtg aac ttc atc gcc    480
Leu Gly Pro Glu Ala Ala Arg His Asn Val Asn Val Asn Phe Ile Ala
145                 150                 155                 160 cag cac tgg acc caa aac aag gag tac ttc tgg ccc gag cgc atc gcc    528
Gln His Trp Thr Gln Asn Lys Glu Tyr Phe Trp Pro Glu Arg Ile Ala
                165                 170                 175 acc gac gag ttc aag gag gat atg gcg cgc cga gtt ccc ctg ggt cgg    576
Thr Asp Glu Phe Lys Glu Asp Met Ala Arg Arg Val Pro Leu Gly Arg
                180                 185                 190 ctc gcg act gcc cga gag atc gcg ctg ctc gcg ttg ttc ctg gcc tcg    624
Leu Ala Thr Ala Arg Glu Ile Ala Leu Leu Ala Leu Phe Leu Ala Ser
        195                 200                 205 gac gag agt gac ttc atc gtc ggc aag tcg atc gag ttc gac ggc ggc    672
Asp Glu Ser Asp Phe Ile Val Gly Lys Ser Ile Glu Phe Asp Gly Gly
    210                 215                 220 tgg gcc acc tga                                                    684
Trp Ala Thr
225
```